US012219201B2

(12) United States Patent
Brammer et al.

(10) Patent No.: US 12,219,201 B2
(45) Date of Patent: Feb. 4, 2025

(54) SYNCHRONIZING VIDEO WORKOUT PROGRAMS ACROSS MULTIPLE DEVICES

(71) Applicant: iFIT Inc., Logan, UT (US)

(72) Inventors: Chase Brammer, Providence, UT (US); Thomas H. Williams, Tucson, AZ (US); Dawson Toth, Elkton, MD (US)

(*) Notice: Subject to any disclaimer, the term of this patent is extended or adjusted under 35 U.S.C. 154(b) by 69 days.

(21) Appl. No.: 17/880,337

(22) Filed: Aug. 3, 2022

(65) Prior Publication Data
US 2023/0039903 A1 Feb. 9, 2023

Related U.S. Application Data

(60) Provisional application No. 63/229,794, filed on Aug. 5, 2021.

(51) Int. Cl.
| | |
|---|---|
| *A61B 5/00* | (2006.01) |
| *A61B 5/0205* | (2006.01) |
| *A61B 5/024* | (2006.01) |
| *A61B 5/22* | (2006.01) |
| *A63B 22/00* | (2006.01) |
| *A63B 22/02* | (2006.01) |
| *A63B 24/00* | (2006.01) |
| *A63B 71/06* | (2006.01) |
| *H04N 21/43* | (2011.01) |

(52) U.S. Cl.
CPC ....... H04N 21/43078 (2020.08); A61B 5/024 (2013.01); A63B 24/0087 (2013.01); A63B 71/0622 (2013.01)

(58) Field of Classification Search
CPC .................................................. A63B 20/00
See application file for complete search history.

(56) References Cited

U.S. PATENT DOCUMENTS

| | | | |
|---|---|---|---|
| 3,123,646 | A | 3/1964 | Easton |
| 3,579,339 | A | 5/1971 | Chang et al. |
| 4,023,795 | A | 5/1977 | Pauls |
| 4,300,760 | A | 11/1981 | Bobroff |
| D286,311 | S | 10/1986 | Martinell et al. |

(Continued)

OTHER PUBLICATIONS

U.S. Appl. No. 63/316,890, filed Mar. 4, 2022.

(Continued)

*Primary Examiner* — Hsiungfei Peng
(74) *Attorney, Agent, or Firm* — Holland & Hart LLP

(57) ABSTRACT

In one aspect of the disclosure, a method that involves keeping state of a video workout program may include communicatively coupling a server in a cloud network to an exercise machine through a first network connection, communicatively coupling the server to a network device through a second network connection, the server providing a video workout program to the exercise machine for execution at the exercise machine to enable a user to perform at least a portion of a workout of the video workout program on the exercise machine, the server keeping state of the video workout program during execution of the video workout program based on inputs from the exercise machine and the network device, and taking an action based on the state. The action may include synchronizing multiple displays, adaptively scaling the video workout program, and/or generating and providing an exercise machine control command to the exercise machine.

19 Claims, 18 Drawing Sheets

(56) References Cited

U.S. PATENT DOCUMENTS

| | | |
|---|---|---|
| 4,681,318 A | 7/1987 | Lay |
| 4,684,126 A | 8/1987 | Dalebout et al. |
| 4,728,102 A | 3/1988 | Pauls |
| 4,750,736 A | 6/1988 | Watterson |
| 4,796,881 A | 1/1989 | Watterson |
| 4,813,667 A | 3/1989 | Watterson |
| 4,830,371 A | 5/1989 | Lay |
| 4,844,451 A | 7/1989 | Bersonnet et al. |
| 4,850,585 A | 7/1989 | Dalebout |
| D304,849 S | 11/1989 | Watterson |
| 4,880,225 A | 11/1989 | Lucas et al. |
| 4,883,272 A | 11/1989 | Lay |
| D306,468 S | 3/1990 | Watterson |
| D306,891 S | 3/1990 | Watterson |
| 4,913,396 A | 4/1990 | Dalebout et al. |
| D307,614 S | 5/1990 | Bingham et al. |
| D307,615 S | 5/1990 | Bingham et al. |
| 4,921,242 A | 5/1990 | Watterson |
| 4,932,650 A | 6/1990 | Bingham et al. |
| D309,167 S | 7/1990 | Griffin |
| D309,485 S | 7/1990 | Bingham et al. |
| 4,938,478 A | 7/1990 | Lay |
| D310,253 S | 8/1990 | Bersonnet et al. |
| 4,955,599 A | 9/1990 | Bersonnet et al. |
| 4,971,316 A | 11/1990 | Dalebout et al. |
| D313,055 S | 12/1990 | Watterson |
| 4,974,832 A | 12/1990 | Dalebout |
| 4,979,737 A | 12/1990 | Kock |
| 4,981,294 A | 1/1991 | Dalebout et al. |
| D315,765 S | 3/1991 | Measom et al. |
| 4,998,725 A | 3/1991 | Watterson et al. |
| 5,000,442 A | 3/1991 | Dalebout et al. |
| 5,000,443 A | 3/1991 | Dalebout et al. |
| 5,000,444 A | 3/1991 | Dalebout et al. |
| D316,124 S | 4/1991 | Dalebout et al. |
| 5,013,033 A | 5/1991 | Watterson et al. |
| 5,014,980 A | 5/1991 | Bersonnet et al. |
| 5,016,871 A | 5/1991 | Dalebout et al. |
| D318,085 S | 7/1991 | Jacobson et al. |
| D318,086 S | 7/1991 | Bingham et al. |
| D318,699 S | 7/1991 | Jacobson et al. |
| 5,029,801 A | 7/1991 | Dalebout et al. |
| 5,034,576 A | 7/1991 | Dalebout et al. |
| 5,058,881 A | 10/1991 | Measom |
| 5,058,882 A | 10/1991 | Dalebout et al. |
| D321,388 S | 11/1991 | Dalebout |
| 5,062,626 A | 11/1991 | Dalebout et al. |
| 5,062,627 A | 11/1991 | Bingham |
| 5,062,632 A | 11/1991 | Dalebout et al. |
| 5,062,633 A | 11/1991 | Engel et al. |
| 5,067,710 A | 11/1991 | Watterson et al. |
| 5,072,929 A | 12/1991 | Peterson et al. |
| D323,009 S | 1/1992 | Dalebout et al. |
| D323,198 S | 1/1992 | Dalebout et al. |
| D323,199 S | 1/1992 | Dalebout et al. |
| D323,863 S | 2/1992 | Watterson |
| 5,088,729 A | 2/1992 | Dalebout |
| 5,090,694 A | 2/1992 | Pauls et al. |
| 5,102,380 A | 4/1992 | Jacobson et al. |
| 5,104,120 A | 4/1992 | Watterson et al. |
| 5,108,093 A | 4/1992 | Watterson |
| D326,491 S | 5/1992 | Dalebout |
| 5,122,105 A | 6/1992 | Engel et al. |
| 5,135,216 A | 8/1992 | Bingham et al. |
| 5,147,265 A | 9/1992 | Pauls et al. |
| 5,149,084 A | 9/1992 | Dalebout et al. |
| 5,149,312 A | 9/1992 | Croft et al. |
| 5,171,196 A | 12/1992 | Lynch |
| D332,347 S | 1/1993 | Raadt et al. |
| 5,190,505 A | 3/1993 | Dalebout et al. |
| 5,192,255 A | 3/1993 | Dalebout et al. |
| 5,195,937 A | 3/1993 | Engel et al. |
| 5,203,826 A | 4/1993 | Dalebout |
| D335,511 S | 5/1993 | Engel et al. |
| D335,905 S | 5/1993 | Cutter et al. |
| D336,498 S | 6/1993 | Engel et al. |
| 5,217,487 A | 6/1993 | Engel et al. |
| D337,361 S | 7/1993 | Engel et al. |
| D337,666 S | 7/1993 | Peterson et al. |
| D337,799 S | 7/1993 | Cutter et al. |
| 5,226,866 A | 7/1993 | Engel et al. |
| 5,244,446 A | 9/1993 | Engel et al. |
| 5,247,853 A | 9/1993 | Dalebout |
| 5,259,611 A | 11/1993 | Dalebout et al. |
| D342,106 S | 12/1993 | Campbell et al. |
| 5,279,528 A | 1/1994 | Dalebout et al. |
| D344,112 S | 2/1994 | Smith |
| D344,557 S | 2/1994 | Ashby |
| 5,282,776 A | 2/1994 | Dalebout |
| 5,295,931 A | 3/1994 | Dreibelbis et al. |
| 5,302,161 A | 4/1994 | Loubert et al. |
| D347,251 S | 5/1994 | Dreibelbis et al. |
| 5,316,534 A | 5/1994 | Dalebout et al. |
| D348,493 S | 7/1994 | Ashby |
| D348,494 S | 7/1994 | Ashby |
| 5,328,164 A | 7/1994 | Soga |
| D349,931 S | 8/1994 | Bostic et al. |
| 5,336,142 A | 8/1994 | Dalebout et al. |
| 5,344,376 A | 9/1994 | Bostic et al. |
| D351,202 S | 10/1994 | Bingham |
| D351,435 S | 10/1994 | Peterson et al. |
| D351,633 S | 10/1994 | Bingham |
| D352,534 S | 11/1994 | Dreibelbis et al. |
| D353,422 S | 12/1994 | Bostic et al. |
| 5,372,559 A | 12/1994 | Dalebout et al. |
| 5,374,228 A | 12/1994 | Buisman et al. |
| 5,382,221 A | 1/1995 | Hsu et al. |
| 5,387,168 A | 2/1995 | Bostic |
| 5,393,690 A | 2/1995 | Fu et al. |
| D356,128 S | 3/1995 | Smith et al. |
| 5,409,435 A | 4/1995 | Daniels |
| 5,429,563 A | 7/1995 | Engel et al. |
| 5,431,612 A | 7/1995 | Holden |
| D360,915 S | 8/1995 | Bostic et al. |
| 5,468,205 A | 11/1995 | McFall et al. |
| 5,489,249 A | 2/1996 | Brewer et al. |
| 5,492,517 A | 2/1996 | Bostic et al. |
| D367,689 S | 3/1996 | Wilkinson et al. |
| 5,511,740 A | 4/1996 | Loubert et al. |
| 5,512,025 A | 4/1996 | Dalebout et al. |
| D370,949 S | 6/1996 | Furner |
| D371,176 S | 6/1996 | Furner |
| 5,527,245 A | 6/1996 | Dalebout et al. |
| 5,529,553 A | 6/1996 | Finlayson |
| 5,540,429 A | 7/1996 | Dalebout et al. |
| 5,549,533 A | 8/1996 | Olson et al. |
| 5,554,085 A | 9/1996 | Dalebout |
| 5,569,128 A | 10/1996 | Dalebout |
| 5,591,105 A | 1/1997 | Dalebout et al. |
| 5,591,106 A | 1/1997 | Dalebout et al. |
| 5,595,556 A | 1/1997 | Dalebout et al. |
| 5,607,375 A | 3/1997 | Dalebout et al. |
| 5,611,539 A | 3/1997 | Watterson et al. |
| 5,622,527 A | 4/1997 | Watterson et al. |
| 5,626,538 A | 5/1997 | Dalebout et al. |
| 5,626,542 A | 5/1997 | Dalebout et al. |
| D380,024 S | 6/1997 | Novak et al. |
| 5,637,059 A | 6/1997 | Dalebout |
| D380,509 S | 7/1997 | Wilkinson et al. |
| 5,643,153 A | 7/1997 | Nylen et al. |
| 5,645,509 A | 7/1997 | Brewer et al. |
| D384,118 S | 9/1997 | Deblauw |
| 5,662,557 A | 9/1997 | Watterson et al. |
| 5,669,857 A | 9/1997 | Watterson et al. |
| 5,672,140 A | 9/1997 | Watterson et al. |
| 5,674,156 A | 10/1997 | Watterson et al. |
| 5,674,453 A | 10/1997 | Watterson et al. |
| 5,676,624 A | 10/1997 | Watterson et al. |
| 5,683,331 A | 11/1997 | Dalebout |
| 5,683,332 A | 11/1997 | Watterson et al. |
| D387,825 S | 12/1997 | Fleck et al. |
| 5,695,433 A | 12/1997 | Buisman |
| 5,695,434 A | 12/1997 | Dalebout et al. |
| 5,695,435 A | 12/1997 | Dalebout et al. |

(56) References Cited

U.S. PATENT DOCUMENTS

| | | | |
|---|---|---|---|
| 5,702,325 A | 12/1997 | Watterson et al. |
| 5,704,879 A | 1/1998 | Watterson et al. |
| 5,718,657 A | 2/1998 | Dalebout et al. |
| 5,720,200 A | 2/1998 | Anderson et al. |
| 5,720,698 A | 2/1998 | Dalebout et al. |
| D392,006 S | 3/1998 | Dalebout et al. |
| 5,722,922 A | 3/1998 | Watterson et al. |
| 5,733,229 A | 3/1998 | Dalebout et al. |
| 5,743,833 A | 4/1998 | Watterson et al. |
| 5,762,584 A | 6/1998 | Daniels |
| 5,762,587 A | 6/1998 | Dalebout et al. |
| 5,772,560 A | 6/1998 | Watterson et al. |
| 5,810,698 A | 9/1998 | Hullett et al. |
| 5,827,155 A | 10/1998 | Jensen et al. |
| 5,830,114 A | 11/1998 | Halfen et al. |
| 5,860,893 A | 1/1999 | Watterson et al. |
| 5,860,894 A | 1/1999 | Dalebout et al. |
| 5,899,834 A | 5/1999 | Dalebout et al. |
| D412,953 S | 8/1999 | Armstrong |
| D413,948 S | 9/1999 | Dalebout |
| 5,951,441 A | 9/1999 | Dalebout et al. |
| 5,951,448 A | 9/1999 | Bolland |
| D416,596 S | 11/1999 | Armstrong |
| 6,003,166 A | 12/1999 | Hald et al. |
| 6,019,710 A | 2/2000 | Dalebout et al. |
| 6,027,429 A | 2/2000 | Daniels |
| 6,033,347 A | 3/2000 | Dalebout et al. |
| D425,940 S | 5/2000 | Halfen et al. |
| 6,059,692 A | 5/2000 | Hickman |
| D428,949 S | 8/2000 | Simonson |
| 6,123,646 A | 9/2000 | Colassi |
| 6,171,217 B1 | 1/2001 | Cutler |
| 6,171,219 B1 | 1/2001 | Simonson |
| 6,174,267 B1 | 1/2001 | Dalebout et al. |
| 6,193,631 B1 | 2/2001 | Hickman |
| 6,228,003 B1 | 5/2001 | Hald et al. |
| 6,238,323 B1 | 5/2001 | Simonson |
| 6,251,052 B1 | 6/2001 | Simonson |
| 6,261,022 B1 | 7/2001 | Dalebout et al. |
| 6,280,362 B1 | 8/2001 | Dalebout et al. |
| 6,296,594 B1 | 10/2001 | Simonson |
| D450,872 S | 11/2001 | Dalebout et al. |
| 6,312,363 B1 | 11/2001 | Watterson et al. |
| D452,338 S | 12/2001 | Dalebout et al. |
| D453,543 S | 2/2002 | Cutler |
| D453,948 S | 2/2002 | Cutler |
| 6,350,218 B1 | 2/2002 | Dalebout et al. |
| 6,387,020 B1 | 5/2002 | Simonson |
| 6,413,191 B1 | 7/2002 | Harris et al. |
| 6,422,980 B1 | 7/2002 | Simonson |
| 6,447,424 B1 | 9/2002 | Ashby et al. |
| 6,458,060 B1 | 10/2002 | Watterson et al. |
| 6,458,061 B2 | 10/2002 | Simonson |
| 6,471,622 B1 | 10/2002 | Hammer et al. |
| 6,563,225 B2 | 5/2003 | Soga et al. |
| 6,601,016 B1 | 7/2003 | Brown et al. |
| 6,623,140 B2 | 9/2003 | Watterson et al. |
| 6,626,799 B2 | 9/2003 | Watterson |
| 6,652,424 B2 | 11/2003 | Dalebout |
| 6,685,607 B1 | 2/2004 | Olson |
| 6,695,581 B2 | 2/2004 | Wasson et al. |
| 6,701,271 B2 | 3/2004 | Willner et al. |
| 6,702,719 B1 | 3/2004 | Brown et al. |
| 6,712,740 B2 | 3/2004 | Simonson |
| 6,730,002 B2 | 5/2004 | Hald et al. |
| 6,743,153 B2 | 6/2004 | Watterson et al. |
| 6,746,371 B1 | 6/2004 | Brown et al. |
| 6,749,537 B1 | 6/2004 | Hickman |
| 6,761,667 B1 | 7/2004 | Cutler et al. |
| 6,770,015 B2 | 8/2004 | Simonson |
| 6,786,852 B2 | 9/2004 | Watterson et al. |
| 6,808,472 B1 | 10/2004 | Hickman |
| 6,821,230 B2 | 11/2004 | Dalebout et al. |
| 6,830,540 B2 | 12/2004 | Watterson et al. |
| 6,863,641 B1 | 3/2005 | Brown et al. |
| 6,866,613 B1 | 3/2005 | Brown et al. |
| 6,875,160 B2 | 4/2005 | Watterson et al. |
| D507,311 S | 7/2005 | Butler et al. |
| 6,918,858 B2 | 7/2005 | Watterson |
| 6,921,351 B1 | 7/2005 | Hickman et al. |
| 6,974,404 B1 | 12/2005 | Watterson et al. |
| 6,997,852 B2 | 2/2006 | Watterson et al. |
| 7,025,713 B2 | 4/2006 | Dalebout et al. |
| D520,085 S | 5/2006 | Willardson et al. |
| 7,044,897 B2 | 5/2006 | Myers et al. |
| 7,052,442 B2 | 5/2006 | Watterson et al. |
| 7,060,006 B1 | 6/2006 | Watterson et al. |
| 7,060,008 B2 | 6/2006 | Watterson et al. |
| 7,070,539 B2 | 7/2006 | Brown et al. |
| 7,097,588 B2 | 8/2006 | Watterson et al. |
| D527,776 S | 9/2006 | Willardson et al. |
| 7,112,168 B2 | 9/2006 | Dalebout et al. |
| 7,128,693 B2 | 10/2006 | Brown et al. |
| 7,166,062 B1 | 1/2007 | Watterson et al. |
| 7,166,064 B2 | 1/2007 | Watterson et al. |
| 7,169,087 B2 | 1/2007 | Ercanbrack et al. |
| 7,169,093 B2 | 1/2007 | Simonson et al. |
| 7,192,388 B2 | 3/2007 | Dalebout et al. |
| 7,250,022 B2 | 7/2007 | Dalebout et al. |
| 7,282,016 B2 | 10/2007 | Simonson |
| 7,285,075 B2 | 10/2007 | Cutler et al. |
| 7,344,481 B2 | 3/2008 | Watterson et al. |
| 7,377,882 B2 | 5/2008 | Watterson et al. |
| 7,425,188 B2 | 9/2008 | Ercanbrack et al. |
| 7,429,236 B2 | 9/2008 | Dalebout et al. |
| 7,455,622 B2 | 11/2008 | Watterson et al. |
| 7,482,050 B2 | 1/2009 | Olson |
| D588,655 S | 3/2009 | Utykanski |
| 7,510,509 B2 | 3/2009 | Hickman |
| 7,537,546 B2 | 5/2009 | Watterson et al. |
| 7,537,549 B2 | 5/2009 | Nelson et al. |
| 7,537,552 B2 | 5/2009 | Dalebout et al. |
| 7,540,828 B2 | 6/2009 | Watterson et al. |
| 7,549,947 B2 | 6/2009 | Hickman et al. |
| 7,556,590 B2 | 7/2009 | Watterson et al. |
| 7,563,203 B2 | 7/2009 | Dalebout et al. |
| 7,575,536 B1 | 8/2009 | Hickman |
| 7,601,105 B1 | 10/2009 | Gipson et al. |
| 7,604,573 B2 | 10/2009 | Dalebout et al. |
| D604,373 S | 11/2009 | Dalebout et al. |
| 7,618,350 B2 | 11/2009 | Dalebout et al. |
| 7,618,357 B2 | 11/2009 | Dalebout et al. |
| 7,625,315 B2 | 12/2009 | Hickman |
| 7,625,321 B2 | 12/2009 | Simonson et al. |
| 7,628,730 B1 * | 12/2009 | Watterson ......... A63B 71/0622 482/4 |
| 7,628,737 B2 | 12/2009 | Kowallis et al. |
| 7,637,847 B1 | 12/2009 | Hickman |
| 7,645,212 B2 | 1/2010 | Ashby et al. |
| 7,645,213 B2 | 1/2010 | Watterson et al. |
| 7,658,698 B2 | 2/2010 | Pacheco et al. |
| 7,674,205 B2 | 3/2010 | Dalebout et al. |
| 7,713,171 B2 | 5/2010 | Hickman |
| 7,713,172 B2 | 5/2010 | Watterson et al. |
| 7,713,180 B2 | 5/2010 | Wickens et al. |
| 7,717,828 B2 | 5/2010 | Simonson et al. |
| 7,736,279 B2 | 6/2010 | Dalebout et al. |
| 7,740,563 B2 | 6/2010 | Dalebout et al. |
| 7,749,144 B2 | 7/2010 | Hammer |
| 7,766,797 B2 | 8/2010 | Dalebout et al. |
| 7,771,329 B2 | 8/2010 | Dalebout |
| 7,775,940 B2 | 8/2010 | Dalebout et al. |
| 7,789,800 B1 | 9/2010 | Watterson et al. |
| 7,798,946 B2 | 9/2010 | Dalebout et al. |
| 7,815,550 B2 | 10/2010 | Watterson et al. |
| 7,857,731 B2 | 12/2010 | Hickman et al. |
| 7,862,475 B2 | 1/2011 | Watterson et al. |
| 7,862,478 B2 | 1/2011 | Watterson et al. |
| 7,862,483 B2 | 1/2011 | Hendrickson et al. |
| D635,207 S | 3/2011 | Dalebout et al. |
| 7,901,330 B2 | 3/2011 | Dalebout et al. |
| 7,909,740 B2 | 3/2011 | Dalebout et al. |
| 7,980,996 B2 | 7/2011 | Hickman |
| 7,981,000 B2 | 7/2011 | Watterson et al. |

(56) References Cited

U.S. PATENT DOCUMENTS

| | | |
|---|---|---|
| 7,985,164 B2 | 7/2011 | Ashby |
| 8,029,415 B2 | 10/2011 | Ashby et al. |
| 8,033,960 B1 | 10/2011 | Dalebout et al. |
| D650,451 S | 12/2011 | Olson et al. |
| D652,877 S | 1/2012 | Dalebout et al. |
| 8,152,702 B2 | 4/2012 | Pacheco |
| D659,775 S | 5/2012 | Olson et al. |
| D659,777 S | 5/2012 | Watterson et al. |
| D660,383 S | 5/2012 | Watterson et al. |
| D664,613 S | 7/2012 | Dalebout et al. |
| 8,251,874 B2 | 8/2012 | Ashby et al. |
| 8,298,123 B2 | 10/2012 | Hickman |
| 8,298,125 B2 | 10/2012 | Colledge et al. |
| D671,177 S | 11/2012 | Sip |
| D671,178 S | 11/2012 | Sip |
| D673,626 S | 1/2013 | Olson et al. |
| 8,690,735 B2 | 4/2014 | Watterson et al. |
| D707,763 S | 6/2014 | Cutler |
| 8,740,753 B2 | 6/2014 | Olson et al. |
| 8,758,201 B2 | 6/2014 | Ashby et al. |
| 8,771,153 B2 | 7/2014 | Dalebout et al. |
| 8,784,270 B2 | 7/2014 | Ashby et al. |
| 8,808,148 B2 | 8/2014 | Watterson et al. |
| 8,814,762 B2 | 8/2014 | Butler et al. |
| D712,493 S | 9/2014 | Ercanbrack et al. |
| 8,840,075 B2 | 9/2014 | Dalebout et al. |
| 8,845,493 B2 | 9/2014 | Watterson et al. |
| 8,870,726 B2 | 10/2014 | Watterson et al. |
| 8,876,668 B2 | 11/2014 | Hendrickson et al. |
| 8,894,549 B2 | 11/2014 | Colledge |
| 8,894,555 B2 | 11/2014 | Colledge et al. |
| 8,911,330 B2 | 12/2014 | Watterson et al. |
| 8,920,288 B2 | 12/2014 | Dalebout et al. |
| 8,986,165 B2 | 3/2015 | Ashby |
| 8,992,364 B2 | 3/2015 | Law et al. |
| 8,992,387 B2 | 3/2015 | Watterson et al. |
| D726,476 S | 4/2015 | Ercanbrack |
| 9,028,368 B2 | 5/2015 | Ashby et al. |
| 9,028,370 B2 | 5/2015 | Watterson et al. |
| 9,039,578 B2 | 5/2015 | Dalebout |
| D731,011 S | 6/2015 | Buchanan |
| 9,072,930 B2 | 7/2015 | Ashby et al. |
| 9,119,983 B2 | 9/2015 | Rhea |
| 9,123,317 B2 | 9/2015 | Watterson et al. |
| 9,126,071 B2 | 9/2015 | Smith |
| 9,126,072 B2 | 9/2015 | Watterson |
| 9,138,615 B2 | 9/2015 | Olson et al. |
| 9,142,139 B2 | 9/2015 | Watterson et al. |
| 9,144,703 B2 | 9/2015 | Dalebout et al. |
| 9,149,683 B2 | 10/2015 | Watterson et al. |
| 9,186,535 B2 | 11/2015 | Ercanbrack |
| 9,186,549 B2 | 11/2015 | Watterson et al. |
| 9,254,409 B2 | 2/2016 | Dalebout et al. |
| 9,254,416 B2 | 2/2016 | Ashby |
| 9,278,248 B2 | 3/2016 | Tyger et al. |
| 9,278,249 B2 | 3/2016 | Watterson |
| 9,278,250 B2 | 3/2016 | Buchanan |
| 9,289,648 B2 | 3/2016 | Watterson |
| 9,339,691 B2 | 5/2016 | Brammer |
| 9,352,185 B2 | 5/2016 | Hendrickson et al. |
| 9,352,186 B2 | 5/2016 | Watterson |
| 9,375,605 B2 | 6/2016 | Tyger et al. |
| 9,381,394 B2 | 7/2016 | Mortensen et al. |
| 9,387,387 B2 | 7/2016 | Dalebout |
| 9,393,453 B2 | 7/2016 | Watterson |
| 9,403,047 B2 | 8/2016 | Olson et al. |
| 9,403,051 B2 | 8/2016 | Cutler |
| 9,421,416 B2 | 8/2016 | Mortensen et al. |
| 9,457,219 B2 | 10/2016 | Smith |
| 9,457,220 B2 | 10/2016 | Olson |
| 9,457,222 B2 | 10/2016 | Dalebout |
| 9,460,632 B2 | 10/2016 | Watterson |
| 9,463,356 B2 | 10/2016 | Rhea |
| 9,468,794 B2 | 10/2016 | Barton |
| 9,468,798 B2 | 10/2016 | Dalebout |
| 9,480,874 B2 | 11/2016 | Cutler |
| 9,492,704 B2 | 11/2016 | Mortensen et al. |
| 9,498,668 B2 | 11/2016 | Smith |
| 9,517,378 B2 | 12/2016 | Ashby et al. |
| 9,521,901 B2 | 12/2016 | Dalebout |
| 9,533,187 B2 | 1/2017 | Dalebout |
| 9,539,461 B2 | 1/2017 | Ercanbrack |
| 9,579,544 B2 | 2/2017 | Watterson |
| 9,586,086 B2 | 3/2017 | Dalebout et al. |
| 9,586,090 B2 | 3/2017 | Watterson et al. |
| 9,604,099 B2 | 3/2017 | Taylor |
| 9,616,276 B2 | 4/2017 | Dalebout et al. |
| 9,616,278 B2 | 4/2017 | Olson |
| 9,623,281 B2 | 4/2017 | Hendrickson et al. |
| 9,636,567 B2 | 5/2017 | Brammer et al. |
| 9,675,839 B2 | 6/2017 | Dalebout et al. |
| 9,682,307 B2 | 6/2017 | Dalebout |
| 9,694,234 B2 | 7/2017 | Dalebout et al. |
| 9,694,242 B2 | 7/2017 | Ashby et al. |
| 9,737,755 B2 | 8/2017 | Dalebout |
| 9,757,605 B2 | 9/2017 | Olson et al. |
| 9,764,186 B2 | 9/2017 | Dalebout et al. |
| 9,767,785 B2 | 9/2017 | Ashby et al. |
| 9,795,822 B2 | 10/2017 | Smith et al. |
| 9,808,672 B2 | 11/2017 | Dalebout |
| 9,849,326 B2 | 12/2017 | Smith |
| 9,878,210 B2 | 1/2018 | Watterson |
| 9,889,334 B2 | 2/2018 | Ashby et al. |
| 9,889,339 B2 | 2/2018 | Douglass |
| 9,937,376 B2 | 4/2018 | McInelly et al. |
| 9,937,377 B2 | 4/2018 | McInelly et al. |
| 9,937,378 B2 | 4/2018 | Dalebout et al. |
| 9,937,379 B2 | 4/2018 | Mortensen et al. |
| 9,943,719 B2 | 4/2018 | Smith et al. |
| 9,943,722 B2 | 4/2018 | Dalebout |
| 9,948,037 B2 | 4/2018 | Ashby |
| 9,968,816 B2 | 5/2018 | Olson et al. |
| 9,968,821 B2 | 5/2018 | Finlayson et al. |
| 9,968,823 B2 | 5/2018 | Cutler |
| 10,010,755 B2 | 7/2018 | Watterson |
| 10,010,756 B2 | 7/2018 | Watterson |
| 10,029,145 B2 | 7/2018 | Douglass |
| D826,350 S | 8/2018 | Hochstrasser |
| 10,046,196 B2 | 8/2018 | Ercanbrack et al. |
| D827,733 S | 9/2018 | Hochstrasser |
| 10,065,064 B2 | 9/2018 | Smith et al. |
| 10,071,285 B2 | 9/2018 | Smith et al. |
| 10,085,586 B2 | 10/2018 | Smith et al. |
| 10,086,254 B2 | 10/2018 | Watterson |
| 10,136,842 B2 | 11/2018 | Ashby |
| 10,186,161 B2 | 1/2019 | Watterson |
| 10,188,890 B2 | 1/2019 | Olson et al. |
| 10,207,143 B2 | 2/2019 | Dalebout et al. |
| 10,207,145 B2 | 2/2019 | Tyger et al. |
| 10,207,147 B2 | 2/2019 | Ercanbrack et al. |
| 10,207,148 B2 | 2/2019 | Powell et al. |
| 10,212,994 B2 | 2/2019 | Watterson et al. |
| 10,220,259 B2 | 3/2019 | Brammer |
| 10,226,396 B2 | 3/2019 | Ashby |
| 10,226,664 B2 | 3/2019 | Dalebout et al. |
| 10,252,109 B2 | 4/2019 | Watterson |
| 10,258,828 B2 | 4/2019 | Dalebout et al. |
| 10,272,317 B2 | 4/2019 | Watterson |
| 10,279,212 B2 | 5/2019 | Dalebout et al. |
| 10,293,211 B2 | 5/2019 | Watterson et al. |
| D852,292 S | 6/2019 | Cutler |
| 10,343,017 B2 | 7/2019 | Jackson |
| 10,376,736 B2 | 8/2019 | Powell et al. |
| 10,388,183 B2 | 8/2019 | Watterson |
| 10,391,361 B2 | 8/2019 | Watterson |
| D864,320 S | 10/2019 | Weston |
| D864,321 S | 10/2019 | Weston |
| 10,426,989 B2 | 10/2019 | Dalebout |
| 10,433,612 B2 | 10/2019 | Ashby et al. |
| 10,441,840 B2 | 10/2019 | Dalebout |
| 10,441,844 B2 | 10/2019 | Powell |
| 10,449,416 B2 | 10/2019 | Dalebout et al. |
| 10,471,299 B2 | 11/2019 | Powell |
| D868,909 S | 12/2019 | Cutler et al. |

(56) References Cited

U.S. PATENT DOCUMENTS

| | | |
|---|---|---|
| 10,492,519 B2 | 12/2019 | Capell et al. |
| 10,493,349 B2 | 12/2019 | Watterson |
| 10,500,473 B2 | 12/2019 | Watterson |
| 10,537,764 B2 | 1/2020 | Smith et al. |
| 10,543,395 B2 | 1/2020 | Powell et al. |
| 10,561,877 B2 | 2/2020 | Workman |
| 10,561,893 B2 | 2/2020 | Chatterton et al. |
| 10,561,894 B2 | 2/2020 | Dalebout et al. |
| 10,569,121 B2 | 2/2020 | Watterson |
| 10,569,123 B2 | 2/2020 | Hochstrasser et al. |
| 10,625,114 B2 | 4/2020 | Ercanbrack |
| 10,625,137 B2 | 4/2020 | Dalebout et al. |
| 10,661,114 B2 | 5/2020 | Watterson et al. |
| 10,668,320 B2 | 6/2020 | Watterson |
| 10,671,705 B2 | 6/2020 | Capell et al. |
| 10,688,346 B2 | 6/2020 | Brammer |
| 10,702,736 B2 | 7/2020 | Weston et al. |
| 10,709,925 B2 | 7/2020 | Dalebout et al. |
| 10,726,730 B2 | 7/2020 | Watterson |
| 10,729,965 B2 | 8/2020 | Powell |
| 10,758,767 B2 | 9/2020 | Olson et al. |
| 10,786,706 B2 | 9/2020 | Smith |
| 10,864,407 B2 | 12/2020 | Watterson et al. |
| 10,918,905 B2 | 2/2021 | Powell et al. |
| 10,932,517 B2 | 3/2021 | Ashby et al. |
| 10,940,360 B2 | 3/2021 | Dalebout et al. |
| 10,953,268 B1 | 3/2021 | Dalebout et al. |
| 10,953,305 B2 | 3/2021 | Dalebout et al. |
| 10,967,214 B1 | 4/2021 | Olson et al. |
| 10,994,173 B2 | 5/2021 | Watterson |
| 11,000,730 B2 | 5/2021 | Dalebout et al. |
| 11,013,960 B2 | 5/2021 | Watterson et al. |
| 11,033,777 B1 | 6/2021 | Watterson et al. |
| 11,058,913 B2 | 7/2021 | Dalebout et al. |
| 11,058,914 B2 | 7/2021 | Powell |
| 11,058,918 B1 | 7/2021 | Watterson et al. |
| 11,187,285 B2 | 11/2021 | Wrobel |
| 11,298,577 B2 | 4/2022 | Watterson |
| 11,326,673 B2 | 5/2022 | Buchanan |
| 11,338,169 B2 | 5/2022 | Dalebout et al. |
| 11,338,175 B2 | 5/2022 | Watterson et al. |
| 11,426,633 B2 | 8/2022 | Watterson et al. |
| 11,451,108 B2 | 9/2022 | Tinney |
| 11,452,903 B2 | 9/2022 | Watterson |
| 11,511,152 B2 | 11/2022 | Powell et al. |
| 11,534,651 B2 | 12/2022 | Ercanbrack et al. |
| 11,534,654 B2 | 12/2022 | Silcock et al. |
| 11,534,655 B2 | 12/2022 | Dalebout et al. |
| 11,565,148 B2 | 1/2023 | Dalebout et al. |
| 11,596,830 B2 | 3/2023 | Dalebout et al. |
| 11,642,564 B2 | 5/2023 | Watterson |
| 11,673,036 B2 | 6/2023 | Dalebout et al. |
| 11,680,611 B2 | 6/2023 | Wrobel |
| 11,700,905 B2 | 7/2023 | Ashby et al. |
| 11,708,874 B2 | 7/2023 | Wrobel |
| 2008/0051256 A1 | 2/2008 | Ashby et al. |
| 2015/0251055 A1 | 9/2015 | Ashby |
| 2016/0058335 A1 | 3/2016 | Ashby |
| 2016/0346595 A1 | 12/2016 | Dalebout et al. |
| 2017/0124912 A1 | 5/2017 | Ashby et al. |
| 2017/0193578 A1 | 7/2017 | Watterson |
| 2017/0266489 A1 | 9/2017 | Douglass et al. |
| 2017/0270820 A1 | 9/2017 | Ashby et al. |
| 2018/0085630 A1 | 3/2018 | Capell et al. |
| 2018/0099116 A1 | 4/2018 | Ashby |
| 2018/0099180 A1 | 4/2018 | Wilkinson |
| 2018/0111034 A1 | 4/2018 | Watterson |
| 2019/0223612 A1 | 7/2019 | Watterson et al. |
| 2019/0269971 A1 | 9/2019 | Capell et al. |
| 2020/0009417 A1 | 1/2020 | Dalebout |
| 2020/0368575 A1 | 11/2020 | Hays et al. |
| 2020/0391069 A1 | 12/2020 | Olson et al. |
| 2021/0001177 A1 | 1/2021 | Smith |
| 2021/0046353 A1 | 2/2021 | Dalebout et al. |
| 2021/0106899 A1 | 4/2021 | Willardson et al. |
| 2021/0110910 A1 | 4/2021 | Ostler et al. |
| 2021/0146221 A1 | 5/2021 | Dalebout et al. |
| 2021/0213331 A1 | 7/2021 | Watterson |
| 2021/0268336 A1 | 9/2021 | Watterson et al. |
| 2021/0291013 A1 | 9/2021 | Nascimento |
| 2021/0299518 A1 | 9/2021 | Brammer et al. |
| 2021/0299542 A1 | 9/2021 | Brammer et al. |
| 2021/0339079 A1 | 11/2021 | Dalebout et al. |
| 2022/0062685 A1 | 3/2022 | Ashby et al. |
| 2022/0104992 A1 | 4/2022 | Ashby |
| 2022/0212052 A1 | 7/2022 | Ercanbrack et al. |
| 2022/0241649 A1 | 8/2022 | Ashby |
| 2022/0241665 A1 | 8/2022 | Dalebout et al. |
| 2022/0241668 A1 | 8/2022 | Willardson et al. |
| 2022/0249912 A1 | 8/2022 | Watterson et al. |
| 2022/0257994 A1 | 8/2022 | Smith |
| 2022/0258007 A1 | 8/2022 | Watterson et al. |
| 2022/0258008 A1 | 8/2022 | Watterson et al. |
| 2022/0266085 A1 | 8/2022 | Dalebout et al. |
| 2022/0280857 A1* | 9/2022 | Watterson ............ H04N 5/2228 |
| 2022/0309042 A1 | 9/2022 | Archer |
| 2022/0314078 A1 | 10/2022 | Watterson et al. |
| 2022/0323827 A1 | 10/2022 | Watterson et al. |
| 2022/0339493 A1 | 10/2022 | Larsen |
| 2022/0339520 A1 | 10/2022 | Toth |
| 2022/0342969 A1 | 10/2022 | Watterson et al. |
| 2022/0347516 A1 | 11/2022 | Taylor |
| 2022/0347548 A1 | 11/2022 | Watterson |
| 2022/0362613 A1 | 11/2022 | Watterson et al. |
| 2022/0362624 A1 | 11/2022 | Dalebout |
| 2022/0395729 A1 | 12/2022 | Toth |
| 2023/0039903 A1 | 2/2023 | Brammer et al. |
| 2023/0054845 A1 | 2/2023 | Smith |
| 2023/0122235 A1 | 4/2023 | Ashby et al. |
| 2023/0128721 A1 | 4/2023 | Plummer |
| 2023/0158358 A1 | 5/2023 | Ercanbrack et al. |
| 2023/0181993 A1 | 6/2023 | Taylor et al. |
| 2023/0191189 A1 | 6/2023 | Taylor et al. |
| 2023/0191197 A1 | 6/2023 | Ashby |
| 2023/0218975 A1 | 7/2023 | Toles et al. |
| 2023/0226401 A1 | 7/2023 | Watterson |

OTHER PUBLICATIONS

U.S. Appl. No. 17/066,485, filed Oct. 9, 2020, Weston et al.
U.S. Appl. No. 17/739,819, filed May 9, 2022, Buchanan.
U.S. Appl. No. 17/841,313, filed Jun. 15, 2022, Weston et al.
U.S. Appl. No. 17/963,822, filed Oct. 11, 2022, Powell.
U.S. Appl. No. 18/091,004, filed Dec. 29, 2022, Cox.
U.S. Appl. No. 18/103,221, filed Jan. 30, 2023, Dalebout et al.
U.S. Appl. No. 18/114,758, filed Feb. 27, 2023, Cutler et al.
U.S. Appl. No. 18/117,263, filed Mar. 3, 2023, Smith et al.
U.S. Appl. No. 18/123,026, filed Mar. 17, 2023, Silcock et al.
U.S. Appl. No. 18/132,277, filed Apr. 7, 2023, Vasquez et al.
U.S. Appl. No. 18/136,535, filed Apr. 19, 2023, Ashby et al.
U.S. Appl. No. 18/141,872, filed May 1, 2023, Ashby et al.
U.S. Appl. No. 18/205,299, filed Jun. 2, 2023, Wrobel.
U.S. Appl. No. 18/207,512, filed Jun. 8, 2023, Chuang.
U.S. Appl. No. 18/210,505, filed Jun. 15, 2023, Nielsen et al.
U.S. Appl. No. 29/702,127, filed Sep. 16, 2019, Cutler et al.
U.S. Appl. No. 62/273,852, filed Dec. 31, 2015, Watterson.
U.S. Appl. No. 63/073,081, filed Sep. 1, 2021, Ashby et al.
U.S. Appl. No. 63/079,697, filed Sep. 7, 2020, Willardson et al.
U.S. Appl. No. 63/086,793, filed Oct. 20, 2020, Ashby.
U.S. Appl. No. 63/134,036, filed Jan. 5, 2021, Ercanbrack et al.
U.S. Appl. No. 63/150,066, filed Feb. 16, 2021, Smith.
U.S. Appl. No. 63/156,801, filed Mar. 4, 2021, Watterson.
U.S. Appl. No. 63/165,498, filed Mar. 24, 2021, Archer.
U.S. Appl. No. 63/179,094, filed Apr. 23, 2021, Watterson et al.
U.S. Appl. No. 63/180,521, filed Apr. 27, 2021, Watterson et al.
U.S. Appl. No. 63/187,348, filed May 11, 2021, Dalebout et al.
U.S. Appl. No. 63/188,431, filed May 13, 2021, Plummer.
U.S. Appl. No. 63/200,903, filed Apr. 2, 2021, Watterson et al.
U.S. Appl. No. 63/211,870, filed Jun. 17, 2021, Watterson et al.
U.S. Appl. No. 63/216,313, filed Jun. 29, 2021, Watterson et al.
U.S. Appl. No. 63/229,794, filed Aug. 12, 2021, Brammer.

(56) References Cited

OTHER PUBLICATIONS

U.S. Appl. No. 63/235,002, filed Aug. 19, 2021, Smith.
U.S. Appl. No. 63/254,470, filed Oct. 11, 2021, Powell.
U.S. Appl. No. 63/278,714, filed Nov. 12, 2021, Taylor.
U.S. Appl. No. 63/289,997, filed Dec. 15, 2021, Taylor et al.
U.S. Appl. No. 63/290,455, filed Dec. 16, 2021, Taylor et al.
U.S. Appl. No. 63/290,557, filed Dec. 16, 2021, Ashby.
U.S. Appl. No. 63/298,170, filed Jan. 10, 2022, Ercanbrack et al.
U.S. Appl. No. 63/299,357, filed Jan. 13, 2022, Toles et al.
U.S. Appl. No. 63/305,976, filed Feb. 2, 2022, Watterson.
U.S. Appl. No. 63/329,270, filed Apr. 8, 2022, Vasquez et al.
U.S. Appl. No. 63/332,581, filed Apr. 25, 2022, Ashby et al.
U.S. Appl. No. 63/338,265, filed May 4, 2022, Ashby et al.
U.S. Appl. No. 63/350,072, filed Jun. 8, 2022, Chuang.
U.S. Appl. No. 63/352,539, filed Jun. 15, 2022, Nielsen et al.
U.S. Appl. No. 63/471,680, filed Jun. 7, 2023, Powell et al.

* cited by examiner

First Data:

| Seconds Since Start | 605 |
|---|---|
| Speed (mph) | 6 |
| Incline % | 0.5 |
| HR Zone | 3 |
| Current HR | 150 |
| Workout State* | In Workout |

First CSV Encoding:

| Seconds Since Start | 605 |
|---|---|
| Speed (mph) | 6 |
| Incline % | 0.5 |
| Resistence | N/A |
| Target RPM | N/A |
| Target Watts | N/A |
| Target HR Zone | 3 |
| Target HR | 150 |
| Workout State* | In Workout |
| CSV Encoding | 605,6,0.5,0,0,0,3,150,1 |

* Workout State (0=Warmup, 1=In Workout, 2=Cool Down)

Second Data:

| Seconds Since Start | 606 |
|---|---|
| Speed (mph) | 6 |
| Incline % | 0.5 |
| HR Zone | 3 |
| Current HR | 152 |
| Workout State* | In Workout |

Second CSV Encoding:

| Seconds Since Start | 606 |
|---|---|
| Speed (mph) | 6 |
| Incline % | 0.5 |
| Resistance | N/A |
| Target RPM | N/A |
| Target Watts | N/A |
| Target HR Zone | 3 |
| Target HR | 152 |
| Workout State* | In Workout |
| CSV Encoding | 605,6,0.5,0,0,0,3,152,1 |

* Workout State (0=Warmup, 1=In Workout, 2=Cool Down)

Third Data:

| Seconds Since Start | 607 |
|---|---|
| Speed (mph) | 5 |
| Incline % | 4.5 |
| HR Zone | 3 |
| Current HR | 156 |
| Workout State* | In Workout |

Third CSV Encoding:

| Seconds Since Start | 607 |
|---|---|
| Speed (mph) | 5 |
| Incline % | 4.5 |
| Resistance | N/A |
| Target RPM | N/A |
| Target Watts | N/A |
| Target HR Zone | 3 |
| Target HR | 156 |
| Workout State* | In Workout |
| CSV Encoding | 607,5,4.5,0,0,0,3,156,1 |

* Workout State (0=Warmup, 1=In Workout, 2=Cool Down)

Fourth Data:

| Seconds Since Start | 608 |
|---|---|
| Speed (mph) | 5 |
| Incline % | 4.5 |
| HR Zone | 3 |
| Current HR | 160 |
| Workout State* | In Workout |

Fourth CSV Encoding:

| Seconds Since Start | 608 |
|---|---|
| Speed (mph) | 5 |
| Incline % | 4.5 |
| Resistance | N/A |
| Target RPM | N/A |
| Target Watts | N/A |
| Target HR Zone | 3 |
| Target HR | 160 |
| Workout State* | In Workout |
| CSV Encoding | 608,5,4.5,0,0,0,3,160,1 |

* Workout State (0=Warmup, 1=In Workout, 2=Cool Down)

My Heart Rate Zones

Your heart rate zones are calculated from your resting and max heart rate. Use these zones to help you gauge your workout intensity and improve your training.

| Zone 5: Beast Mode | 173-192 BPM |
| Zone 4: Performance | 154-172 BPM |
| Zone 3: Cardio | 135-153 BPM |
| Zone 2: Endurance | 115-134 BPM |
| Zone 1: Recovery | 96-114 BPM |
| Resting HR | EST. 65 BPM > |
| Max HR | EST. 185 BPM > |

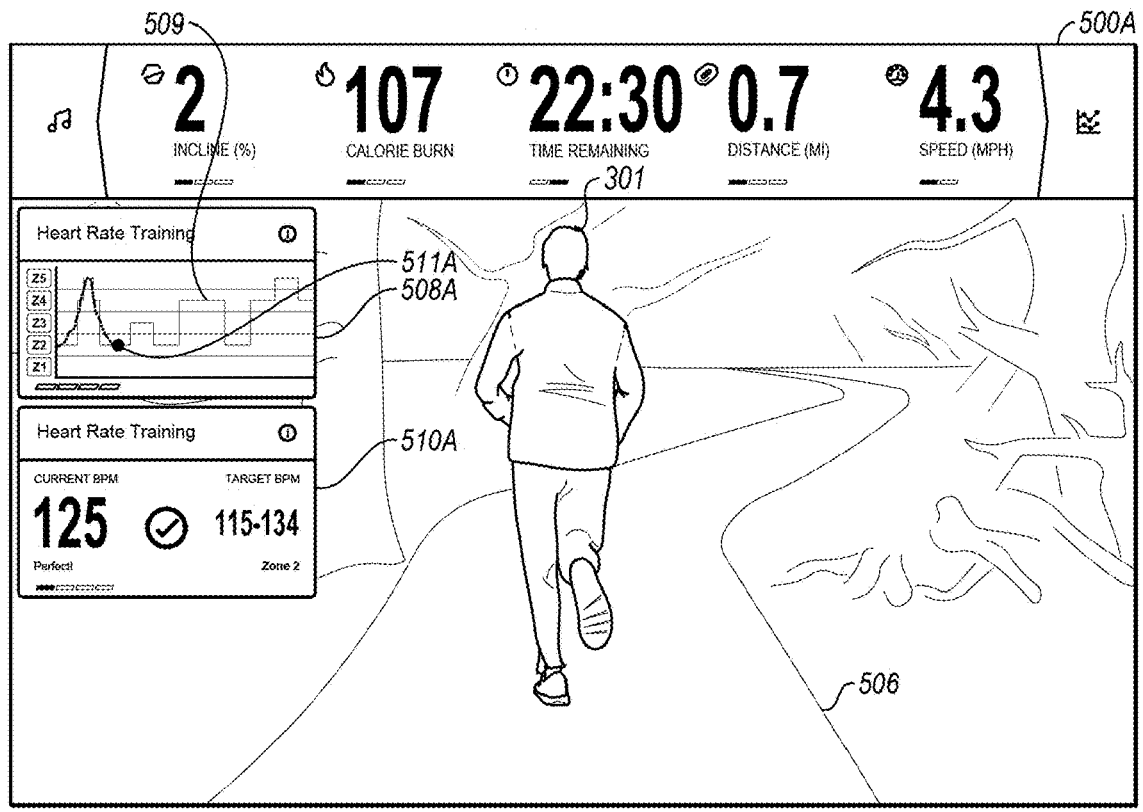

| Current Programmed Heart Rate Zone | Zone 2 |
|---|---|
| Current Programmed Heart Rate Zone Range | 115-134 BPM |
| Previous Programmed Heart Rate Zone | Zone 4 |
| Time Since Workout Began | 450 Seconds |
| Time Since Zone Change | 70 Seconds |
| Time Remaining in Current Programmed Heart Rate Zone | 50 Seconds |
| Time Remaining in Workout | 1350 Seconds |
| Heart Rate Monitoring Rate | Once Per Second |
| Threshold Heart Rate Trend Rate | -5 Seconds |
| Warmup-Time Threshold | 180 Seconds |
| User's Last Ten Actual Heart Rates (BPM) | 122,122,123,123,124,124,125,124,125,125 |
| Baseline Difficulty Level | $B_0$ |
| Baseline Speed | 4 MPH |
| Current Difficulty Level | $B_2$ |
| Current Speed | 4.3 MPH |
| User's Actual Heart Rate | 125 BPM |
| User's Actual Heart Rate Zone | Zone 2 |
| User's Actual Heart Rate Zone Range | 115-134 BPM |

*FIG. 5A*

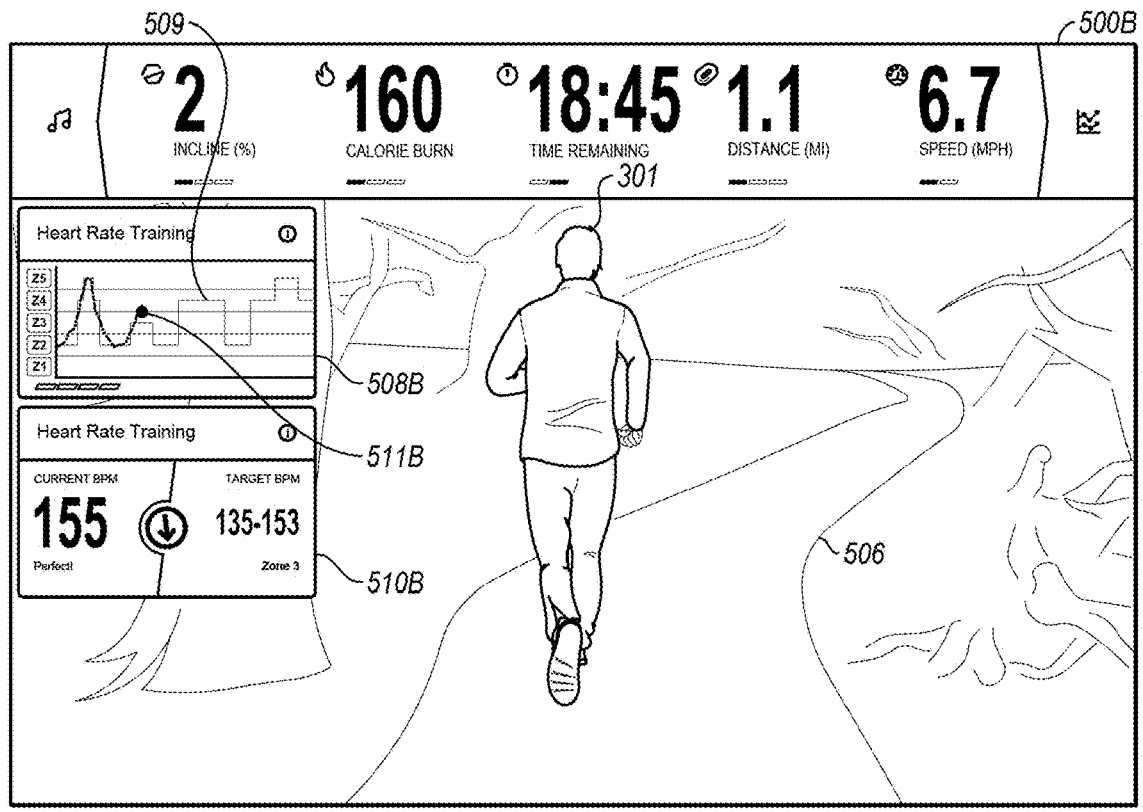

| | |
|---|---|
| Current Programmed Heart Rate Zone | Zone 3 |
| Current Programmed Heart Rate Zone Range | 135-153 BPM |
| Previous Programmed Heart Rate Zone | Zone 2 |
| Time Since Workout Began | 675 Seconds |
| Time Since Zone Change | 60 Seconds |
| Time Remaining in Current Programmed Heart Rate Zone | 60 Seconds |
| Time Remaining in Workout | 1125 Seconds |
| Heart Rate Monitoring Rate | Once Per Second |
| Threshold Heart Rate Trend Rate | +4 Seconds |
| Warmup-Time Threshold | 180 Seconds |
| User's Last Ten Actual Heart Rates (BPM) | 152,152,153,153,154,154,155,155,155,155 |
| Baseline Difficulty Level | $B_0$ |
| Baseline Speed | 6 MPH |
| Current Difficulty Level | $B_2$ |
| Current Speed | 6.7 MPH |
| User's Actual Heart Rate | 155 BPM |
| User's Actual Heart Rate Zone | Zone 4 |
| User's Actual Heart Rate Zone Range | 154-172 BPM |

FIG. 5B

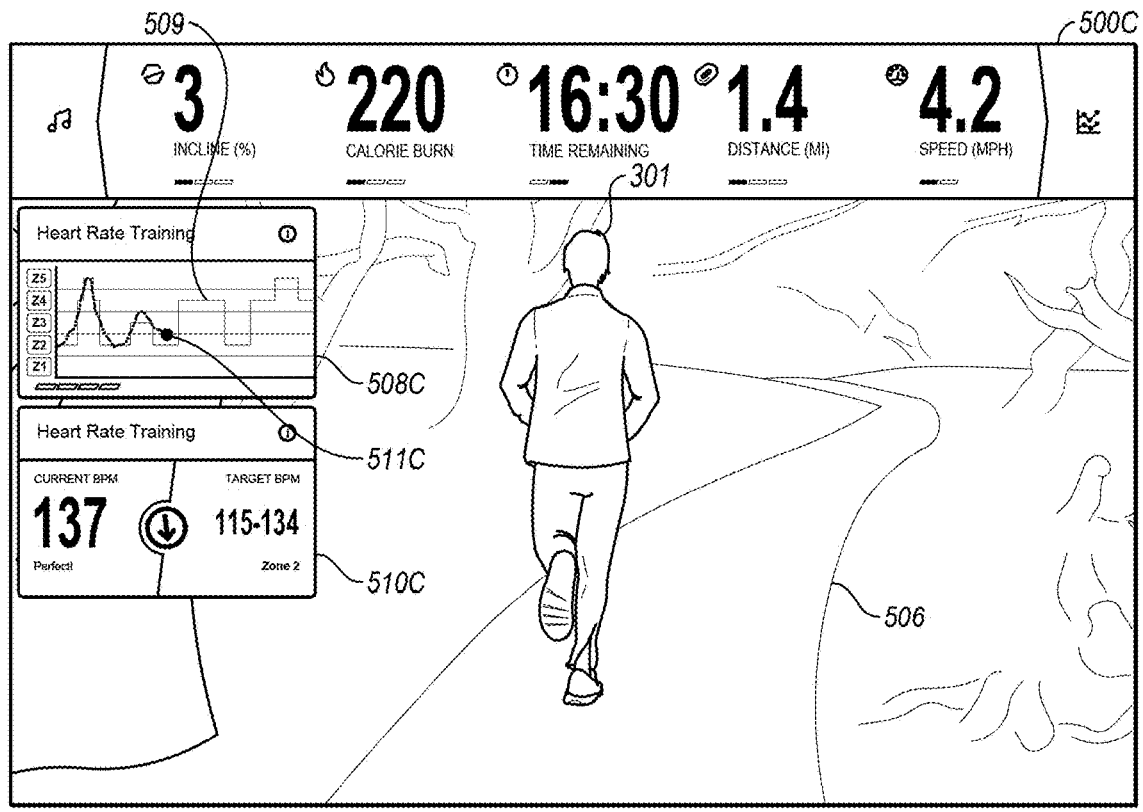

| | |
|---|---|
| Current Programmed Heart Rate Zone | Zone 2 |
| Current Programmed Heart Rate Zone Range | 115-134 BPM |
| Previous Programmed Heart Rate Zone | Zone 3 |
| Time Since Workout Began | 810 Seconds |
| Time Since Zone Change | 50 Seconds |
| Time Remaining in Current Programmed Heart Rate Zone | 70 Seconds |
| Time Remaining in Workout | 990 Seconds |
| Heart Rate Monitoring Rate | Once Per Second |
| Threshold Heart Rate Trend Rate | -4 Seconds |
| Warmup-Time Threshold | 180 Seconds |
| User's Last Ten Actual Heart Rates (BPM) | 131,131,132,133,133,134,135,136,136,137 |
| Baseline Difficulty Level | $B_0$ |
| Baseline Speed | 4 MPH |
| Current Difficulty Level | $B_1$ |
| Current Speed | 4.2 MPH |
| User's Actual Heart Rate | 137 BPM |
| User's Actual Heart Rate Zone | Zone 3 |
| User's Actual Heart Rate Zone Range | 135-153 BPM |

FIG. 5C

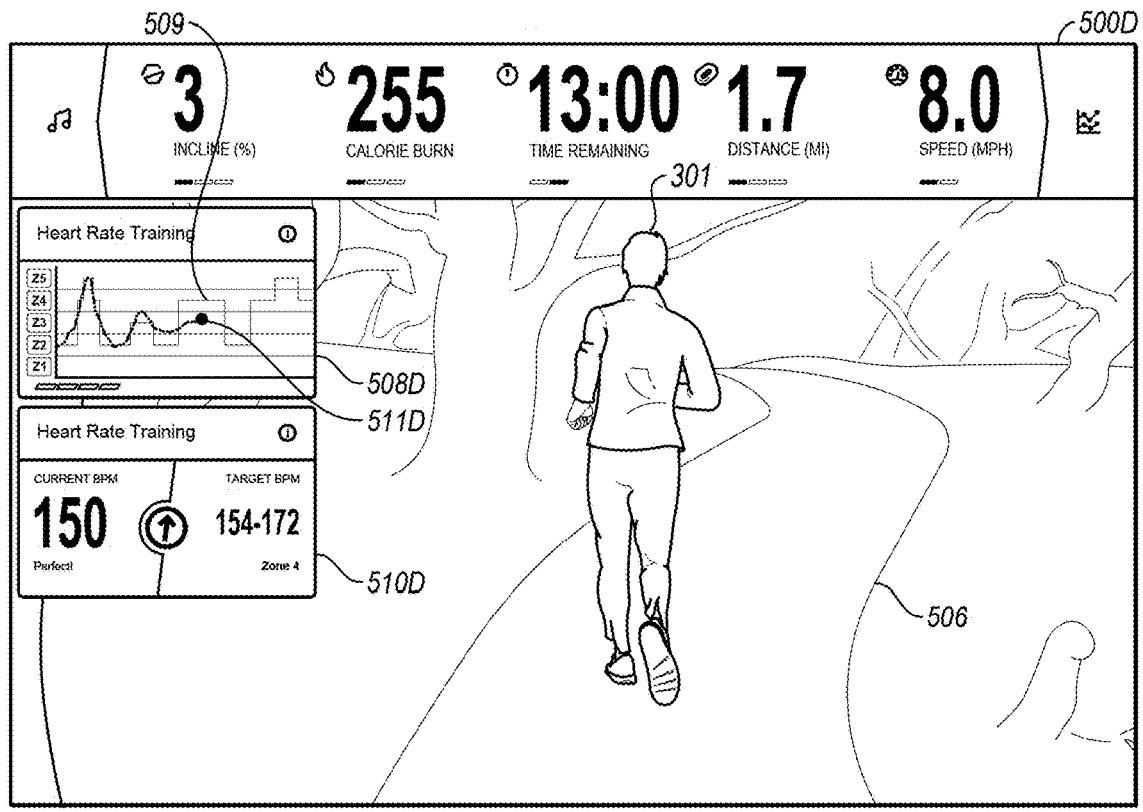

| | |
|---|---|
| Current Programmed Heart Rate Zone | Zone 4 |
| Current Programmed Heart Rate Zone Range | 154-172 BPM |
| Previous Programmed Heart Rate Zone | Zone 2 |
| Time Since Workout Began | 1020 Seconds |
| Time Since Zone Change | 120 Seconds |
| Time Remaining in Current Programmed Heart Rate Zone | 120 Seconds |
| Time Remaining in Workout | 780 Seconds |
| Heart Rate Monitoring Rate | Once Per Second |
| Threshold Heart Rate Trend Rate | +5 Seconds |
| Warmup-Time Threshold | 180 Seconds |
| User's Last Ten Actual Heart Rates (BPM) | 148,147,148,149,149,149,150,150,150,150 |
| Baseline Difficulty Level | $B_0$ |
| Baseline Speed | 8 MPH |
| Current Difficulty Level | $B_0$ |
| Current Speed | 8 MPH |
| User's Actual Heart Rate | 150 BPM |
| User's Actual Heart Rate Zone | Zone 3 |
| User's Actual Heart Rate Zone Range | 135-153 BPM |

*FIG. 5D*

SYNCHRONIZING VIDEO WORKOUT PROGRAMS ACROSS MULTIPLE DEVICES

This application claims the benefit of and priority to U.S. Provisional Patent Application No. 63/229,794 filed Aug. 5, 2021, which application is incorporated herein by reference in its entirety for all that it discloses.

BACKGROUND

Stationary exercise machines have become an increasingly popular way to exercise. To combat the boredom and burnout that is often experienced by users that exercise with these exercise machines, exercise machines are often sold with a number of different pre-programmed workout programs that are saved within the electronics of the exercise machines. For example, these workout programs may include a "fat burn" workout program, a "hills" workout program, a "performance" workout program, and/or other workout programs.

To enable a user to become more immersed in a workout performed on an exercise machine, some exercise machines are capable of executing video workout programs. A video workout program generally includes a video that depicts a trainer performing a workout to allow one or more users to mimic the workout. For example, where a trainer is running at 6 miles per hour in a video of a video workout program, each of the users may control the running belts of their respective treadmills to likewise operate at 6 miles per hour.

The subject matter claimed herein is not limited to embodiments that solve any disadvantages or that operate only in environments such as those described above. Rather, this background is only provided to illustrate one example technology area where some embodiments described herein may be practiced.

SUMMARY

In one aspect of the disclosure, a method to synchronize a video workout program across multiple devices may include communicatively coupling a server in a cloud network to an exercise machine through a first network connection; communicatively coupling the server in the cloud network to a network device through a second network connection; the server providing a video workout program to the exercise machine for execution at the exercise machine to enable a user to perform at least a portion of a workout of the video workout program on the exercise machine; the server keeping state of the video workout program during execution of the video workout program based on inputs from the exercise machine and the network device; the server generating an exercise machine control command based on the state; and the server providing the exercise machine control command over the first network connection to the exercise machine to control an actuator of the exercise machine according to the exercise machine control command.

Another aspect of the disclosure may include any combination of the above-mentioned features and may further include receiving input indicative of the user performing at least a second portion of the workout off of the exercise machine; and updating workout data included in the state to reflect performance of the second portion of the workout off of the exercise machine, where at least some of the updated workout data is displayed on the first display of the exercise machine.

Another aspect of the disclosure may include any combination of the above-mentioned features and may further include the network device is located in proximity to the exercise machine without being directly communicatively coupled to the exercise machine.

Another aspect of the disclosure may include any combination of the above-mentioned features and may further include synchronizing a first display of the exercise machine with a second display of the network device based on the state.

Another aspect of the disclosure may include any combination of the above-mentioned features and may further include the synchronizing based on the state includes distributing workout data of the video workout program that is displayed on the first display of the exercise machine, received from the exercise machine, and updated in the state to the network device for display on the second display of the network device.

Another aspect of the disclosure may include any combination of the above-mentioned features and may further include the synchronizing based on the state includes providing one or more workout controls to the network device for display on the second display; receiving as one or more of the inputs from the network device a manual workout adjustment to adjust a difficulty of the workout entered using the one or more workout controls; generating an exercise machine control command to adjust the difficulty of the workout according to the manual workout adjustment; sending the exercise machine control command to the exercise machine for implementation at the exercise machine; and updating the state to include the adjusted workout difficulty; where the exercise machine displays the adjusted workout difficulty on the first display of the exercise machine.

Another aspect of the disclosure may include any combination of the above-mentioned features and may further include the portion of the workout includes a first portion performable on the exercise machine, the workout further includes a second portion performable off the exercise machine, where the first portion of the workout includes a first exercise modality and the second portion of the workout includes a second exercise modality that is different than the first exercise modality.

Another aspect of the disclosure may include any combination of the above-mentioned features and may further include the second portion of the workout is performable with a second exercise machine; and the method further includes communicatively coupling the server in the cloud network to the second exercise machine through a third network connection; and the server further keeping state of the video workout program during execution of the video workout program based on inputs from the second exercise machine.

Another aspect of the disclosure may include any combination of the above-mentioned features and may further include the server generating a second exercise machine control command based on the state and the server providing the second exercise machine control command over the third network connection to the second exercise machine to control an actuator of the second exercise machine according to the second exercise machine control command.

Another aspect of the disclosure may include any combination of the above-mentioned features and may further include communicatively coupling the server in the cloud network to a heart rate monitor coupled to a user through a third network connection and the server further keeping state of the video workout program during execution of the video workout program based on inputs from the heart rate monitor.

Another aspect of the disclosure may include any combination of the above-mentioned features and may further include adaptively scaling the video workout program on the exercise machine based on the state.

Another aspect of the disclosure may include any combination of the above-mentioned features and may further include a non-transitory computer-readable medium having computer-executable instructions stored thereon that are executable by a processing unit to perform or control performance of any combination of the above-mentioned features.

Another aspect of the disclosure may include any combination of the above-mentioned features and may further include, or may stand alone by including, a method to synchronize a video workout program across multiple devices. The method may include communicatively coupling a server in a cloud network to an exercise machine that includes a first display through a first network connection; communicatively coupling the server in the cloud network to a second display through a second network connection; the server providing a video workout program to the exercise machine for execution at the exercise machine to enable a user to perform at least a portion of a workout of the video workout program on the exercise machine; the server keeping state of the video workout program during execution of the video workout program at the exercise machine based on inputs from the exercise machine; and the server synchronizing the second display with the first display of the exercise machine based on the state.

Another aspect of the disclosure may include any combination of the above-mentioned features and may further include the second display is located in proximity to the exercise machine without being directly communicatively coupled to the exercise machine.

Another aspect of the disclosure may include any combination of the above-mentioned features and may further include the synchronizing based on the state includes distributing workout data of the video workout program that is displayed on the first display of the exercise machine, received from the exercise machine, and updated in the state to the second display for display on the second display.

Another aspect of the disclosure may include any combination of the above-mentioned features and may further include the synchronizing based on the state includes providing one or more workout controls to the second display for display on the second display; receiving as one or more inputs from the second display a manual workout adjustment to adjust a difficulty of the workout entered using the one or more workout controls; generating an exercise machine control command to adjust the difficulty of the workout according to the manual workout adjustment; sending the exercise machine control command to the exercise machine for implementation at the exercise machine; and updating the state to include the adjusted workout difficulty; where the exercise machine displays the adjusted workout difficulty on the first display of the exercise machine.

Another aspect of the disclosure may include any combination of the above-mentioned features and may further include a non-transitory computer-readable medium having computer-executable instructions stored thereon that are executable by a processing unit to perform or control performance of any combination of the above-mentioned features.

Another aspect of the disclosure may include any combination of the above-mentioned features and may further include, or may stand alone by including, a method to keep state of a video workout program. The method may include communicatively coupling a server in a cloud network to an exercise machine through a first network connection; communicatively coupling the server in the cloud network to a heart rate monitor through a second network connection; the server providing a video workout program to the exercise machine for execution at the exercise machine to enable a user to perform at least a portion of a workout of the video workout program on the exercise machine; the server keeping state of the video workout program during execution of the video workout program at the exercise machine based on the inputs from the exercise machine and the heart rate monitor; and the server adaptively scaling the video workout program based on the state.

Another aspect of the disclosure may include any combination of the above-mentioned features and may further include the heart rate monitor is located in proximity to the exercise machine without being directly communicatively coupled to the exercise machine.

Another aspect of the disclosure may include any combination of the above-mentioned features and may further include the inputs from the heart rate monitor include heart rate measurements of the user over time; and the adaptively scaling includes periodically determining from the heart rate measurements at least one of that an actual heart rate zone of the user is not equal to a current programmed heart rate zone; or that the actual heart rate of the user is not trending toward the current programmed heart rate zone; and in response to the periodically determining, adjusting a current difficulty level of the video workout program to adjust the user's actual heart rate zone toward the current programmed heart rate zone.

Another aspect of the disclosure may include any combination of the above-mentioned features and may further include the adjusting includes adjusting the current difficulty level upward if the actual heart rate zone is lower than the current programmed heart rate zone; and downward if the actual heart rate zone is higher than the current programmed heart rate zone.

Another aspect of the disclosure may include any combination of the above-mentioned features and may further include the adaptively scaling further includes the server generating an exercise machine control command to adjust the current difficulty level based on the state; and the adjusting the current difficulty level includes the server providing the exercise machine control command over the first network connection to the exercise machine to control an actuator of the exercise machine according to the exercise machine control command.

Another aspect of the disclosure may include any combination of the above-mentioned features and may further include a non-transitory computer-readable medium having computer-executable instructions stored thereon that are executable by a processing unit to perform or control performance of any combination of the above-mentioned features.

It is to be understood that both the foregoing summary and the following detailed description are explanatory and are not restrictive of the invention as claimed.

BRIEF DESCRIPTION OF THE DRAWINGS

Embodiments will be described and explained with additional specificity and detail through the use of the accompanying drawings in which:

FIGS. 5A-5D illustrate video frames and data charts that may be employed in dynamically scaling a video workout program on an exercise machine based on heart rate monitoring;

Throughout the drawings, identical reference numbers designate similar, but not necessarily identical, elements.

DETAILED DESCRIPTION

Figure 1:
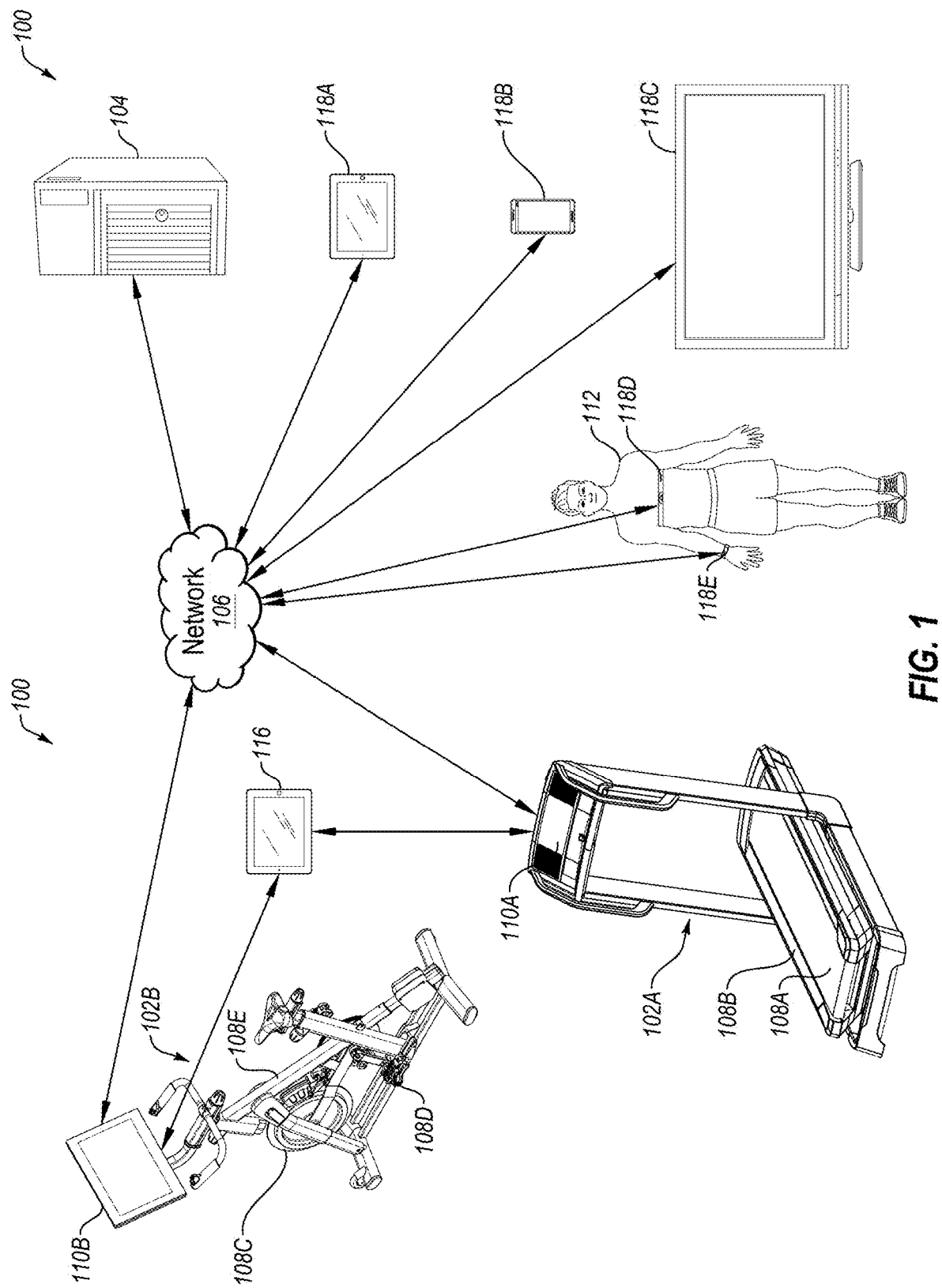
FIG. 1 illustrates an example exercise machine system.

When performing a workout depicted in a video workout program, some users may desire to simultaneously view different views of the video workout program on different display devices. For example, a video workout program may include both a video view of a trainer performing a workout and a statistics view of the user's workout statistics (e.g., elapsed time, distance, current speed, current incline, etc.) or other views where the views may be mutually exclusive (e.g., only one view may be displayed at a time on a given display device). Some users attempt to work around this problem by simultaneously starting the same video workout program on both an exercise machine and another display device so that the video view may be displayed on a console of the exercise machine while the statistics view is displayed on the other display device, or vice versa. However, this solution does not automatically synchronize the video workout program across the exercise machine and the other display device so the user must remember to stop/start the video workout program on both devices at the same time to keep them manually synchronized. Sometimes users in these circumstances may forget to stop/start the video workout program at both devices at the same time, leading to an unsynchronized condition which may be bothersome for the users.

Alternatively or additionally, some workouts may mix modalities, e.g., may include multiple different types of exercises performable on different exercise machines or equipment or without any exercise machine or equipment. For example, a workout may include at least two segments of different exercise modalities, such as at least two of a segment for cycling on a stationary bike, a segment for running on a treadmill, a segment for lifting weights, a segment for performing yoga, and/or other segment(s). Some existing exercise machines are unable to track total workout statistics for mixed modality workouts; for instance, such exercise machines may be unable to track workout statistics for segments of a workout not performed at or with the exercise machine.

Some embodiments herein automatically synchronize video workout programs across multiple devices and/or track total workout statistics for mixed modality workouts (and/or mixed modality video workout programs) by keeping workout state in the cloud. For example, data associated with a video workout program executed at an exercise machine may be collected at a server in the cloud from an exercise machine and/or one or more network devices that are not directly connected to the exercise machine to maintain workout state for the video workout program. Alternatively or additionally, the collected data may be shared with the exercise machine and/or the network devices. According to some embodiments, by maintaining workout state in the cloud, the video workout program or multiple views thereof may be simultaneously displayed on multiple display devices, inputs from one or more of the network devices may be used to set or adjust a difficulty of the video workout program at the exercise machine, and/or workout statistics may be tracked for mixed modality workouts.

Turning now to the drawings, FIG. 1 illustrates an example exercise machine system 100. The exercise machine system 100 may include one or more exercise machines 102A, 102B (hereinafter collectively "exercise machines 102" or generically "exercise machine 102") and a server 104 connected by a network 106.

In some embodiments, the network 106 may be configured to communicatively couple any two devices in the exercise machine system 100 to one another, and/or to other devices. In some embodiments, the network 106 may be any wired or wireless network, or combination of multiple networks, configured to send and receive communications between systems and devices. In some embodiments, the network 106 may include a Personal Area Network (PAN), a Local Area Network (LAN), a Metropolitan Area Network (MAN), a Wide Area Network (WAN), a Storage Area Network (SAN), the Internet, or some combination thereof. In some embodiments, the network 106 may also be coupled to, or may include, portions of a telecommunications network, including telephone lines, for sending data in a variety of different communication protocols, such as a cellular network or a Voice over IP (VoIP) network.

Each of the exercise machines 102 may include one or more moveable members 108A, 108B, 108C, 108D, 108E (hereinafter collectively "moveable members 108" or generically "moveable member 108") and a console 110A, 110B (hereinafter collectively "consoles 110" or generically "console 110"). In general, a user 112 may use the exercise machines 102, including moveable members 108 and/or consoles 110, to perform workouts.

In general, one or more of the moveable members 108 may be moved by or for the user 112 while the user is performing workouts. For example, the exercise machine 102A may be a treadmill 102A and the moveable members 108A and 108B may respectively be a treadmill belt 108A and a treadmill deck 108B; the treadmill belt 108A may rotate around the treadmill deck 108B such that the user 112 may perform a walking or running workout by walking or running on the rotating treadmill belt 108A. As another example, the exercise machine 102B may be a stationary bike 102B and the moveable members 108C, 108D, and 108E may respectively include a flywheel 108C, pedals 108D, and a frame 108E; the user 108 may perform a cycling workout by operating the pedals 108D to turn the flywheel 108C while on the stationary bike 102B.

The consoles 110 may each include one or more input devices for the user 112 to manually control or adjust operating parameters of one or more of the moveable members 108 for workouts. For example, the console 110A may include one or more buttons, a touchscreen interface, or other input device(s) that may be operated by the user 112 to set or adjust a speed of the treadmill belt 108A and/or an incline of the treadmill deck 108B. As another example, the console 110B may include one or more buttons, a touchscreen interface, or other input device(s) that may be operated by the user 112 to set or adjust a rotational resistance of the flywheel 108C (which flywheel 108C may be driven by the pedals 108D) and/or an incline of the frame 108E.

Alternatively or additionally, the server 104 may provide one or more video workout programs to the exercise machines 102 for execution at the exercise machines 102 and/or the consoles 110. Each video workout program may automatically control the one or more moveable members 108 of the exercise machines 102 during execution of the video workout programs. Each video workout program may include one or more of images, video, audio, and/or exercise machine control commands. The images and/or video in some embodiments include images or video of scenery and/or a trainer performing a workout that the exercise machine 102 may simulate. For example, a video workout program for execution at the treadmill 102A may include images or video depicting a trainer performing a running workout along a mountain trail (or other running route), while a video workout program for execution at the stationary bike 102B may include images or video depicting a trainer performing a cycling workout along a coastal highway (or other cycling route). Audio included in such video workout programs may include environmental sounds picked up while filming video included in the video workout programs, spoken instructions or information from the trainer to the user 112 about an upcoming segment of the workout, goals or targets of the workout, objects or points of interest shown in the video, or the like. Exercise machine control commands may include executable commands that control one or more of the moveable members 108 and/or corresponding actuators.

Various methods exist for creating such video workout programs, some examples of which will now be described. For example, a videographer may operate a video camera to capture video for use in a video workout program as described herein. The video camera may include stabilization capabilities to avoid the captured video from being unduly shaky. Some video captured by the videographer may include a trainer performing a workout. In some embodiments, a trainer may perform a workout on location and a videographer may capture video of the trainer as the trainer performs the workout on location. Additional details regarding creating video workout programs that include video of a trainer performing a workout are disclosed in U.S. patent application Ser. No. 16/742,76, filed Jan. 14, 2020, which is incorporated herein by reference in its entirety for all that it discloses.

In some embodiments, a trainer may perform a workout on a set or stage in front of one or more chroma key screens or display panels and the video of the trainer performing the workout may be combined with an image or video of a scene or moving through an environment using chroma keying or other suitable technology. The server 104 or other server may be configured to combine the video of the trainer with the background image or video, to format video according to one or more formats, or perform other methods or operations described herein.

Background images or videos that may be combined with videos of trainers performing workouts may include captured images or video, rendered images or video, or a combination of the two. As used herein, a captured image or video refers to an image or video captured by a video camera filming in the real world. A videographer with a video camera may capture video of the real world while the videographer is static or in motion (e.g., walking, running, biking, rowing). A rendered image or video refers to an image or video generated by a game engine or rendering engine, such as the UNREAL ENGINE game engine, of a virtual world. For example, the exercise machine system 100 may further include a game engine that may be employed to render an image or video that may be used as a background image or video for combination with video of a trainer performing a workout. Additional details regarding combining video of a trainer with a background image or video are disclosed in U.S. Provisional Patent Application Ser. No. 63/156,801, filed Mar. 4, 2021, which is incorporated herein by reference in its entirety for all that it discloses.

In some embodiments, performance parameters of a trainer performing a workout or of a videographer as the videographer captures video (e.g., to be used as background video) may be recorded as the trainer and/or videographer performs the workout. For example, performance parameters may be recorded for trainers as they perform their respective workouts and/or for videographers as they capture video while performing a workout. The performance parameters may include speed, cadence, heart rate, incline, or other performance parameters. Alternatively or additionally, a virtual speed of movement through a virtual environment depicted in a rendered video, an incline of the virtual environment, or other parameters of the rendered video or the virtual environment may be recorded. The performance parameters of the trainer 108 and/or the videographer 110 and/or the parameters of the rendered video or the virtual environment may be used to generate exercise machine control commands, as described in more detail elsewhere herein.

The various videos discussed herein may be formatted in any one of multiple video formats, at least some of which being capable of supporting a subtitle stream. Some example formats may include MPEG-4, Dynamic Adaptive Streaming over HTTP (MPEG-DASH), and HTTP Live Streaming (HLS).

Next, a producer (not shown in FIG. 1) or other user may utilize a computer (not shown in FIG. 1) to input exercise machine control commands for the video or the combined video into a video workout program, which may be encoded into a subtitle stream of the video, or may be encoded separately from the video or the combined video, such as in separate data packets. For example, where the video or the combined video is being produced to be utilized as a live video workout program, the producer may input the exercise machine control commands using the computer synchronously or substantially synchronously with the video camera capturing the video of the trainer performing the workout (e.g., during a live event) and/or with generation of the combined video when one is generated. In this example, the producer may also give corresponding instructions to the trainer, such as through an earpiece worn by the trainer, to help the trainer and the producer be in sync following a common script or plan for the workout. Alternatively, where the video or the combined video is produced to be utilized in a pre-recorded or archived video workout program, the producer may input exercise machine control commands using the computer subsequent to the capture of the video of the trainer performing the workout and/or generation of the combined video, where one is generated (e.g., minutes, hours, or days after the live event). The exercise machine control commands may control operation of exercise machines at which the video workout program is executed.

In some embodiments, the producer may utilize the computer to input environmental control commands into the video workout program, which may be encoded into the subtitle stream of the video or the combined video or may be encoded separately from the video or the combined video, such as in separate data packets. The environmental control commands may be input synchronously or substantially synchronously with the video camera capturing the video of the trainer performing the workout and/or with generation of the combined video when one is generated. The environmental control commands may control operation of one or more environmental control devices integrated with and/or in a vicinity of an exercise machine on which the video workout program is executed so as to control or affect an environment of a user of the exercise machine. Such environmental control devices may include heat lamps, fans, oil diffusers, scent dispensers, lights, humidifiers, mist dispensers, or other environmental control device. The environmental control devices may be smart devices, may be communicatively coupled to a corresponding exercise machine, and/or may be communicatively coupled to the network 106, to receive the environmental control commands in the video workout program.

In some embodiments, the video workout program, including the video or the combined video and the control commands (which may be encoded in the subtitle stream of the video or the combined video, or may be encoded separately from the video or the combined video) may be stored or made accessible at or to the server 104.

To execute a video workout program at the exercise machines 102, the video workout program may be transmitted over the network 106 from the server 104 to be used in connection with the exercise machines 102. For example, the video workout program may be transmitted from the server 104 to the exercise machines 102, to their consoles 110, a touchscreen display, and/or other user interface. Alternatively or additionally, a separate tablet 116 may function as a console, or may function in connection with a console or other user interface, of the exercise machine 102, and may also include a display, such as a touchscreen display. The tablet 116 may communicate with the console 110 and/or with the exercise machine 102 via a network connection, such as a Bluetooth connection. The user 112 may operate the console 110 or tablet 116 to browse available video workout programs and/or select a desired video workout program to be downloaded or streamed to the exercise machine 102 from the server 104.

At the console 110, the tablet 116, or more generally at the exercise machine 102, the video or the combined video and the control commands (which may be encoded in the subtitle stream of the video or the combined video, or may be encoded separately) may be decoded and/or accessed. Then, the console 110, the tablet 116, or more generally the exercise machine 102 may display the video or the combined video from the video workout program (e.g., of the trainer performing the workout) while simultaneously controlling one or more moveable members of the exercise machine 102 using the exercise machine control commands. Additional details regarding controlling an exercise machine or environmental control device using exercise machine control commands or environmental control commands can be found in U.S. patent application Ser. No. 16/742,762, filed Jan. 14, 2020 and U.S. Provisional Patent Application Ser. No. 63/156,801, filed Mar. 4, 2021, each of which is incorporated herein by reference in its entirety for all that it discloses.

Some users may desire to simultaneously view different views of a video workout program on different display devices. For example, a video workout program may include both a video view of a trainer performing a workout and a statistics view of the user's workout statistics (e.g., elapsed time, distance, current speed, current incline, etc.) or other views where the views may be mutually exclusive (e.g., only one view may be displayed at a time on a given display device). Some users attempt to work around this problem by simultaneously starting the same video workout program on the exercise machine 102 and another display device so that the video view may be displayed on the console 110 of the exercise machine 102 while the statistics view is displayed on the other display device, or vice versa. However, this solution does not automatically synchronize the video workout program across the exercise machine and the other display device so the user must remember to stop/start the video workout program on both devices at the same time to keep them manually synchronized. Sometimes users in these circumstances may forget to stop/start the video workout program at both devices at the same time, leading to an unsynchronized condition which may be bothersome for the users.

Alternatively or additionally, some workouts may mix modalities, e.g., may include multiple different types of exercises performable on different exercise machines or equipment or without any exercise machine or equipment. For example, a workout may include at least two segments of different exercise modalities, such as at least two of a segment for cycling on a stationary bike, a segment for running on a treadmill, a segment for lifting weights, a segment for performing yoga, and/or other segment(s). In these and other embodiments, the user 112 may perform a given segment of a workout using the exercise machine 102 at which the video workout program is executed, using a different exercise machine than the one at which the video workout program is executed, using different exercise equipment, and/or using no exercise machine or exercise equipment at all. Some existing exercise machines are unable to track total workout statistics for mixed modality workouts; for instance, such exercise machines may be unable to track workout statistics for segments of a workout not performed at or with the exercise machine.

Some embodiments herein automatically synchronize video workout programs across multiple devices and/or track total workout statistics for mixed modality workouts (and/or mixed modality video workout programs) by keeping workout state in the cloud. For example, data associated with a video workout program executed at any of the exercise machines 102 may be collected from the exercise machine 102 and/or one or more network devices 118A, 118B, 118C, 118D, 118E (hereinafter collectively "network devices 118" or generically "network device 118") at the server 104 or other server in the cloud to maintain workout state for the video workout program and/or may be shared with the exercise machines 102 and/or the network devices 118. According to some embodiments, by maintaining workout state in the cloud, the video workout program or multiple views thereof may be simultaneously displayed on multiple display devices, inputs from one or more of the network devices may be used to set or adjust a difficulty of the video workout program at the exercise machine 102, and/or workout statistics may be tracked for mixed modality workouts.

The network devices 118 may generally include electronic devices capable of connecting to the network 106 and/or to the server 104 through the network 106. One or more of the network devices 118 may be unable to connect directly (e.g., via Bluetooth) to the exercise machine 102 and/or one or more of the network devices 118 may be able to connect directly to the exercise machine 102. In the illustrated embodiment, the network device 118A is a tablet, the network device 118B is a smartphone, the network device 118 is a smart television, and each of the network devices 118D, 118E is a heart rate monitor where the network device 118D is specifically a heart rate strap and the network device 118E is specifically a heart rate watch. One or more of the network devices 118 may be owned by, associated with, and/or in the possession of the user 112. One or more of the network devices 118 may be owned by, associated with, and/or in the possession of individuals/entities other than the user.

According to some embodiments, the exercise machine 102 executes a video workout program and workout state for the video workout program is maintained at the server 104. For example, the exercise machine 102 may periodically send workout data to the server 104 where the server 104 may update workout state accordingly.

In an example, one or more of the network devices 118A, 118B, 118C may be in the possession of the user 112 and may connect to the server 104 through the network 106 to receive workout data of the video workout program executing at the exercise machine 102 based on the workout state at the server 104. Accordingly, keeping workout state at the server 104 may permit one view of the video workout program to be displayed on the console 110 of the exercise machine while one or more of the same or other views of the same video workout program may be simultaneously displayed on one or more of the network devices 118A, 118B, 118C without the user 112 having to manually synchronize multiple instances of the video workout program across two or more different displays.

In another example, one or more of the network devices 118A, 118B, 118C may be in the possession of an individual or entity other than the user 112 and may connect to the server 104 through the network 106 to receive workout data of the video workout program executing at the exercise machine 102 based on the workout state at the server 104. Accordingly, the same or different views of the video workout program may be simultaneously displayed on the console 110 of the exercise machine for the user 112 and on one or more of the network devices 118A, 118B, 118C for the individual or entity other than the user 112. Keeping workout state at the server 104 may thereby permit the user 112 to share their workout progress in real time with other individuals.

In another example, one or more of the network devices 118A, 118B, 118C may be in the possession of the user 112 and may connect to the server 104 through the network 106 to receive workout controls (e.g., a user interface that is operable to control workout parameters) of the video workout program executing at the exercise machine 102 based on the workout state at the server 104. Accordingly, the user 112 may operate the workout controls at the network device 118A, 118B, 118C to provide input to set or adjust workout parameters (e.g., speed, resistance, incline, etc.) of the video workout program. The server 104 may receive the input from the network device 118A, 118B, 118C and update the workout state to reflect the input while also generating exercise machine control commands from the input. The exercise machine control commands may be sent to the exercise machine 102 to implement the settings/adjustments input by the user 112. Accordingly, keeping workout state at the server 104 may permit the user 112 to adjust workout parameters of a video workout program executing at the exercise machine 102 from a network device 118 that is not directly connected to the exercise machine 102.

In another example, one or more of the network devices 118D, 118E may connect to the server 104 through the network 106 and may generate heart rate data of the user 112 during execution of the video workout program at the exercise machine 102. The heart rate data may include continuous or periodic heart rate measurements of the user 112. The heart rate measurements may be received at the server 104 and may influence workout state, such as current operating parameters, of the exercise machine 102. For example, some video workout programs may include target heart rate zones for different segments of the video workout program. If the current heart rate of the user 112 is not in and/or trending toward a current target heart rate zone for a given segment of the workout, the server 104 may generate an exercise machine control command to adjust an operating parameter of the exercise machine 102 to cause the heart rate of the user 112 to move towards and/or reach the current target heart rate zone. As a specific example, if the heart rate of the user 112 is below and/or not trending upwards towards a current target heart rate zone, an operating parameter of the exercise machine 102 such as speed, incline, resistance, or the like may be increased to cause the heart rate of the user 112 to increase towards and/or reach the current target heart rate zone. As another specific example, if the heart rate of the user 112 is above and/or not trending downwards towards a current target heart rate zone, an operating parameter of the exercise machine 102 such as speed, incline, resistance, or the like may be decreased to cause the heart rate of the user 112 to decrease towards and/or reach the current target heart rate zone. Accordingly, keeping workout state at the server 104 may permit operating parameters of the exercise machine 102 to be automatically adjusted based on heart rate measurements from a network device 118 that is not directly connected to the exercise machine 102.

In another example, the video workout program is a mixed modality workout program. The exercise machine 102 that is executing the video workout program continuously and/or periodically reports workout data, e.g., workout statistics, to the server 104 at least for one or more segments of the workout that are performed on or with the exercise machine 102. The server 104 may update workout state based on the workout data from the exercise machine 102. During one or more other segments of the workout that are not performed on or with the exercise machine 102, workout data may be continuously and/or periodically reported by one or more other exercise machines 102 and/or network devices 118. For example, if a segment of the workout is performed on another exercise machine 102, the other exercise machine 102 may report workout data to the server 104 for the segment performed at or with the other exercise machine 102. As another example, if a segment of the workout is performed without any exercise machine, the heart rate monitor network devices 118D, 118E or other network devices 118 (e.g., video cameras, smart weights (e.g., weights with integrated sensors), etc.) may report workout data to the server 104 for the corresponding segment. The server 104 may update workout state based on the workout data from the other exercise machine 102 and/or network devices 118. Accordingly, keeping workout state at the server 104 may permit collection in a single video workout program of workout statistics for mixed modality workouts.

The network devices 118D, 118E implemented as heart rate monitors are examples of sensors that may be used to generate and/or gather biological parameters, performance parameters, or other information of users of the exercise machines 102. Such sensors may more generally include heart rate sensors (such as may be included in the network devices 118D, 118E), VO2 max sensors, brain wave sensors, hydration level sensors, breathing/respiratory rate sensors, blood pressure sensors, current sensors, speed sensors (e.g., tachometers), weight sensors, pressure sensors, gait sensors, fingerprint sensors, biometric sensors (e.g., heart rate sensors, breathing sensors, gait sensors, fingerprint sensors), accelerometers, or other sensors. Such sensors may be integrated with, included in, coupled to, or otherwise associated with one or more of the exercise machines 102, the network devices 118, and/or the users of the exercise machines 102.

In some embodiments in which biological parameters are collected (such as heart rate), a probability that the biological data is accurate may be determined. For example, when gathering heart rate data from a heart-rate strap or heart rate watch (such as the network devices 118D, 118E) worn by the user, it is possible that the heart rate data is inaccurate due to improper positioning of the strap, some debris or other object or material blocking all or part of a sensor of the heart rate watch or strap, poor connectivity with the receiver, etc. To account for this possibility, some embodiments may analyze the probability of the heart rate data being accurate, and where the probability of accuracy is below some threshold may discard, ignore, or otherwise not rely on the heart rate data.

The exercise machine 102A is illustrated in FIG. 1 as a treadmill. The treadmill 102A may include multiple different moveable members, including the treadmill belt 108A and the treadmill deck 108B, which may include one or more operating parameters that are selectively adjustable within a limited range. During performance of a workout using a video workout program on the treadmill 102A, the treadmill belt 108A may rotate and the treadmill deck 108B may incline. One example of an operating parameter on the treadmill 102A is a speed of the treadmill belt 108A. The treadmill belt 108A may rotate at different speeds within a limited range. An actuator (see FIG. 2), for example a belt motor, may selectively adjust the speed at which the treadmill belt 108A rotates within the limited range. Another example of an operating parameter on the treadmill 102A is the inclination of the treadmill deck 108B. The treadmill deck 108B may be selectively inclinable to different angles within a limited range. An actuator, for example an incline motor, may selectively adjust the incline of the treadmill deck 108B within the limited range.

The exercise machine 102B is illustrated in FIG. 1 as a stationary bike. The stationary bike 102B may include multiple different moveable members, including the flywheel 108C, the pedals 108D, and the frame 108E, which include one or more operating parameters that are selectively adjustable within a limited range. During performance of a workout using a video workout program on the stationary bike 102B, movement of the pedals 108D may cause the flywheel 108C to rotate. One example of an operating parameter on the stationary bike 102B is the amount of resistance applied to the flywheel 108C. A differing amount of resistance can be applied to the flywheel 108C to make rotation of the pedals 108D more difficult or less difficult. An actuator, such as a brake, may be used to selectively adjust the amount of resistance that is applied to the flywheel 108C within the limited range. Another example of an operating parameter on the stationary bike 102B is the position of the frame 108E. The frame 108E may tilt forward, backward, or from side to side within a limited range. An actuator, such as a tilt motor, may selectively adjust the position of the frame 108E within the limited range.

Another example of an exercise machine is an elliptical machine. An example elliptical machine may include multiple different moveable members, such as a flywheel, foot rails or pedals, and handles, which include one or more operating parameters that are selectively adjustable within a limited range. During performance of a workout using a video workout program on the elliptical machine, movement of the foot rails or pedals and the handles may cause the flywheel to rotate. One example of an operating parameter on the elliptical machine is the amount of resistance applied to the flywheel. A differing amount of resistance can be applied to the flywheel to make the movement of the foot rails or pedals and the handles more difficult or less difficult. An actuator, such as a brake, may be used to selectively adjust the amount of resistance that is applied to the flywheel. Another example of an operating parameter on the elliptical machine is the inclination of foot rails or pedals. The foot rails or pedals may be inclinable to different angles within a limited range. An actuator, such as an incline motor, may selectively adjust the incline of the foot rails or pedals within the limited range. Yet another example of an operating parameter on exercise machine is the stride length of the foot rails or pedals and/or the handles. The stride length of the foot rails or pedals and/or the handles may be adjustable to different distances within a limited range. An actuator, for example a stride length motor, may selectively adjust the stride length of the foot rails or pedals and/or the handles within the limited range.

Another example of an exercise machine is a rower machine. An example rower machine may include multiple different moveable members, including a flywheel, a rowbar, and a seat, which include one or more operating parameters that are selectively adjustable within a limited range. During performance of a workout using a video workout program on the rower machine, movement of the rowbar may cause the flywheel to rotate. One example of an operating parameter on the rower machine is the amount of resistance applied to the flywheel. A differing amount of resistance can be applied to the flywheel to make pulling on the rowbar more difficult or less difficult. An actuator, such as a brake, may be used to selectively adjust the amount of resistance that is applied to the flywheel within the limited range.

Thus, according to some embodiments, exercise machines 102 and/or network devices 118 may be, in effect, clients of a workout state maintained at the server 104.

Figure 2:
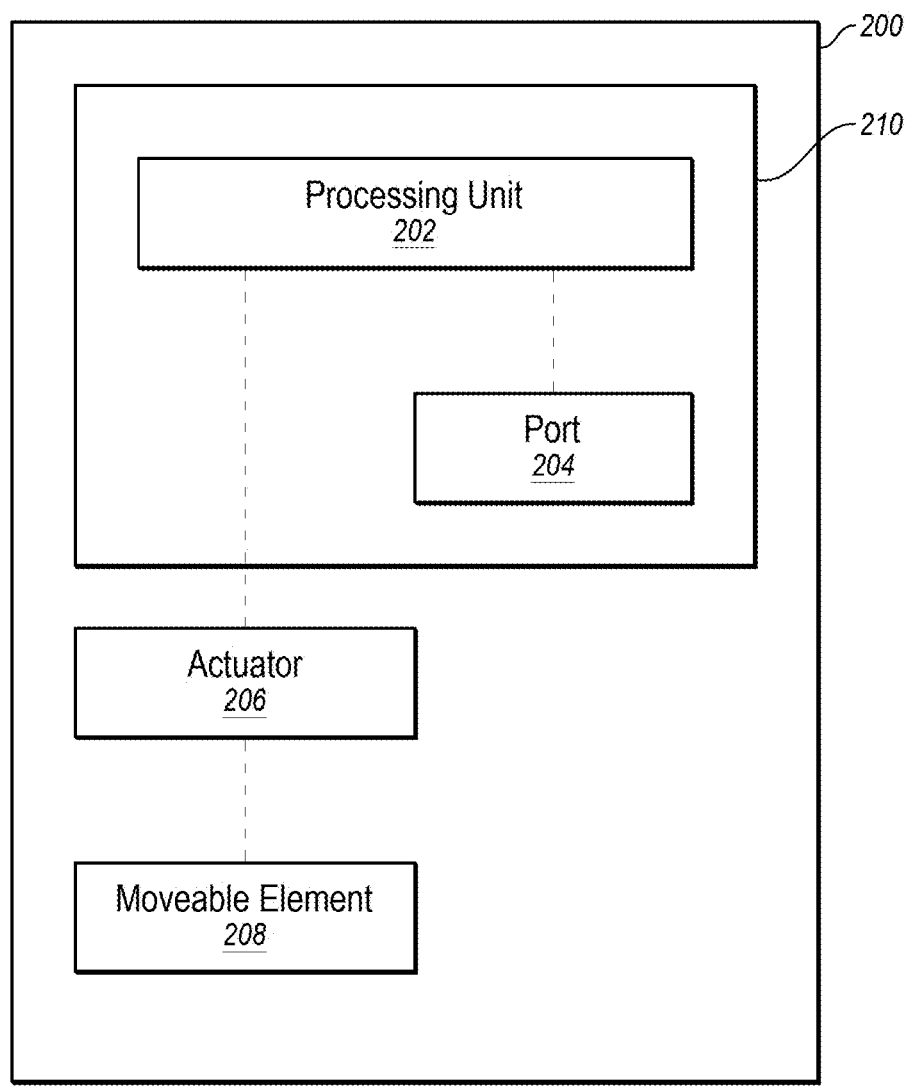
FIG. 2 illustrates a block diagram of an example exercise machine.

FIG. 2 illustrates a block diagram of an example exercise machine 200. The exercise machine 200 of FIG. 2 may represent, and may include similar components to, any of the exercise machines 102 of FIG. 1, for example.

As disclosed in FIG. 2, the exercise machine 200 may include a processing unit 202, a receiving port 204, an actuator 206, and a moveable member 208. The moveable member 208 may be the same as or similar to any of the moveable members 108 of FIG. 1, for example. The processing unit 202 may be communicatively connected to the receiving port 204 and may be included within a console 210, which may be the same as or similar to the console 110 of FIG. 1, for example. The processing unit 202 may also be communicatively connected to the actuator 206. In response to control commands executed by the processing unit 202, the actuator 206 may selectively adjust one or more operating parameters of the moveable member 208 within a limited range.

Data, including data in a video workout program, can be received by the exercise machine 200 through the receiving port 204. As stated previously, a video workout program may include video as well as control commands. Control commands may provide control instructions to an exercise machine (such as a treadmill, an elliptical machine, an exercise bike, or a rower machine) and/or one or more associated output control devices. Control commands may include, for example, control commands for a belt motor, an incline motor, chair recline motor, and/or other actuators. In addition to actuator control commands, control commands may further include distance control commands, time control commands, and/or heart rate zone control commands. These control commands may provide a series of actuator control commands for execution at specific times or at specific distances. For example, a control command for an actuator to be at a certain level for a specific amount of time or for a specific distance. These control commands may also provide a series of actuator control commands for execution at specific times or at specific distances based on a user's monitored heart rate or heart rate trends over time. For example, a control command for an actuator may dictate a certain heart rate zone for a certain amount of time or distance, and a difficulty level of this control command may be dynamically scaled based on a user's monitored heart rate in order to get or keep the user in the certain heart rate zone for the certain amount of time or distance. Additional details regarding dynamically scaling a difficulty level of a control command based on a user's monitored heart rate can be found in U.S. patent application Ser. No. 16/742,762, filed Jan. 14, 2020, which is incorporated herein by reference in its entirety for all that it discloses.

Using a control command, received at the receiving port 204 in a video workout program, such as a control command that is decoded from a subtitle stream of a video of a video workout program for example, the processing unit 202 may control the actuator 206 or output device on or associated with the exercise machine 200 in the sequence and at the times or distances specified by the control command. For example, actuator control commands that provide the processing unit 202 with commands for controlling a belt motor, an incline motor, a flywheel brake, stride length motor, a chair recline motor, or another actuator may be included in the control commands received in a video workout program at the exercise machine 200.

Actuator control commands can be received for different time segments or distance segments of a workout. For example, a ten-minute workout or a ten-minute mindfulness session may have twenty different control commands that provide the processing unit 202 with a different control command for controlling an actuator or output device every thirty seconds. Alternatively, a ten-mile workout may have twenty different control commands that provide a processing unit with a different control command for controlling an actuator or output device every half mile. Workouts may be of any duration or distance and different control commands may be received at any time or distance during the workout. Alternatively, a 5-minute workout may have 300 different control commands that provide the processing unit 202 with a different control command for controlling an actuator or output device once per second.

The control commands received in a video workout program at the exercise machine 200 may be executed by the processing unit 202 in a number of different ways. For example, the control commands may be received and then stored into a read/write memory that is included in or coupled to the processing unit 202. Alternatively, the control commands may be streamed to the exercise machine 200 in real-time. The control commands may also be received and/or executed from a portable memory device, such as a USB memory stick or an SD card.

Video workout programs can improve users' workout experiences. However, video workout programs may involve a significant amount of time and cost to produce, which may limit a total number of video workout programs available to users. Further, some users may be unable or uninterested in doing some of the available video workout programs. In view of the foregoing, the video workout programs users typically use may be limited and/or may grow stale over time, e.g., users may tire of repeating the same video workout programs. Some embodiments herein may expand a number of available video workout programs and/or customize the video workout programs for individual users. In general, for example, each of multiple video workout programs may be divided into segments, segments from two or more of the video workout programs may be selected based on user criteria specific to a given user, and the selected segments may be spliced together or otherwise combined to generate a custom video workout program for the given user.

FIGS. 3A-3D illustrate video frames and charts that may be employed in controlling an exercise machine using exercise machine control commands of a video workout program. The exercise machine control commands may be encoded into a subtitle stream of a video of the video workout program or may be encoded separately from the video. In more detail, FIGS. 3A-3D illustrate frames 300A-300D of video captured by a videographer of a trainer 301 performing a workout, which may include running a marathon along a path 306. Further, FIGS. 3A-3D also illustrate data charts 302A-302D which contain certain relevant data parameters gathered during the workout at the same time that the corresponding frame of video is captured, manually or automatically using one or more sensors, for example. Finally, FIGS. 3A-3D also illustrate comma separated values (CSV) encoding charts 304A-304D showing how the data parameters from the data charts 302A-302D may be translated and encoded into control commands.

The frames 300A-300D of video captured of the trainer 301 running the marathon represent frames of video captured in succession, one second apart. However, other intervening frames of video may also be captured, such as 29 intervening frames of video between each of the successive frames 300A-300D, resulting in a captured video having 30 frames per second. The reason that only one frame per second is illustrated in the frames 300A-300D of video is because the encoding of control commands of a video workout program into a subtitle stream of a video of the video workout program may occur only once per second in the example encoding disclosed in FIGS. 3A-3D. Other encoding rates are also possible, such as encoding twice per second or four times per second, for example. In some embodiments, the encoding rate may be up to as many times per second as there are frames per second (e.g., where the frame rate is 30 frames per second, the encoding rate may up to 30 times per second).

Figure 3A:
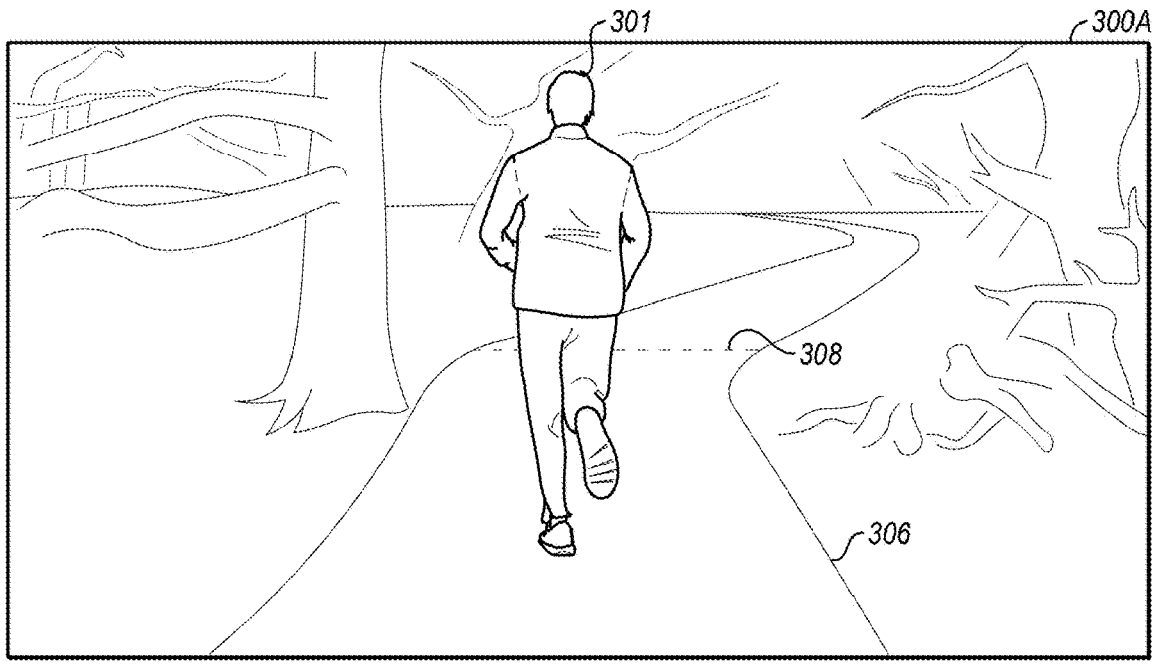
FIGS. 3A-3D illustrate video frames and charts that may be employed in controlling an exercise machine using exercise machine control commands of a video workout program

As disclosed in the frame 300A of FIG. 3A, the trainer 301 may be performing a workout by running a marathon along the path 306. As disclosed in the data chart 302A, at the time that the frame 300A is captured by a video camera, 605 seconds may have transpired since the start of the workout, the trainer 301 may be running at a pace of 6 miles per hour up a 0.5% incline, the trainer 301 may currently be in a heart rate zone 3 with a heart rate of 150 beats per minute, and may be in a workout state of "In Workout" (as opposed to a workout state of "Warmup" or "Cool Down"). As disclosed in the CSV encoding chart 304A, the data parameters from the data chart 302A may be encoded into a CSV encoding 305A in a subtitle stream of a video, which is timed with (e.g., linked or tied to) the frame 300A, as "605,6,0.5,0,0,0,3,150,1", which represents 605 seconds since the start of the workout, a speed of 6 miles per hour, a 0.5% incline, resistance being non-applicable (with N/A being represented by a 0), a target revolutions per minute being non-applicable (with N/A being represented by a 0), a target watts being non-applicable (with N/A being represented by a 0), a target heart rate zone of 3, a target heart rate of 150, and a workout state of 1 (which represents a workout state of "In Workout"). In some embodiments, the CSV encoding 305A may have all values separated by a comma, may have all values be numbers (e.g., number between −99999.0 to 99999.0), may not have spaces between values, may encode values in order (e.g., so that the position of each value can be used to interpret the meaning of each value), and may allow for a new value if the new value is appended at the end of the CSV encoding.

Figure 3B:
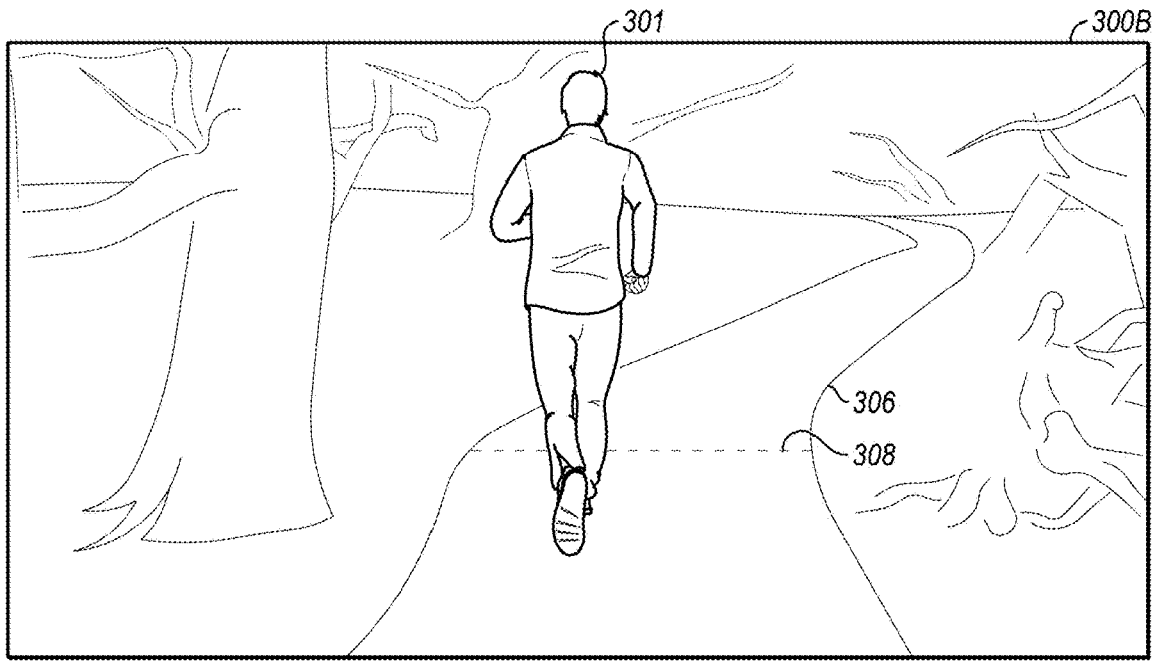

As disclosed in the frame 300B of FIG. 3B, the trainer 301 may continue performing the workout by running the marathon along the path 306. As disclosed in the data chart 302B, at the time that the frame 300B is captured by a video camera, 606 seconds may have transpired since the start of the workout (e.g. one additional second has transpired since the frame 300A was captured), the trainer 301 may still be running at a pace of 6 miles per hour up a 0.5% incline, the trainer 301 may still be in heart rate zone 3 but with an increased heart rate of 152 beats per minute, and may still be in a workout state of "In Workout." As illustrated in frame 300B, the trainer 301 may be approaching a transition 308 in the path 306 where the incline transitions from a relatively gradual 0.5% incline to a relatively steep 4.5% incline. As disclosed in the CSV encoding chart 304B, the data parameters from the data chart 302B may be encoded into a CSV encoding 305B in a subtitle stream of a video, which is timed with frame 300B, as "606,6,0.5,0,0,0,3,152,1".

Figure 3C:
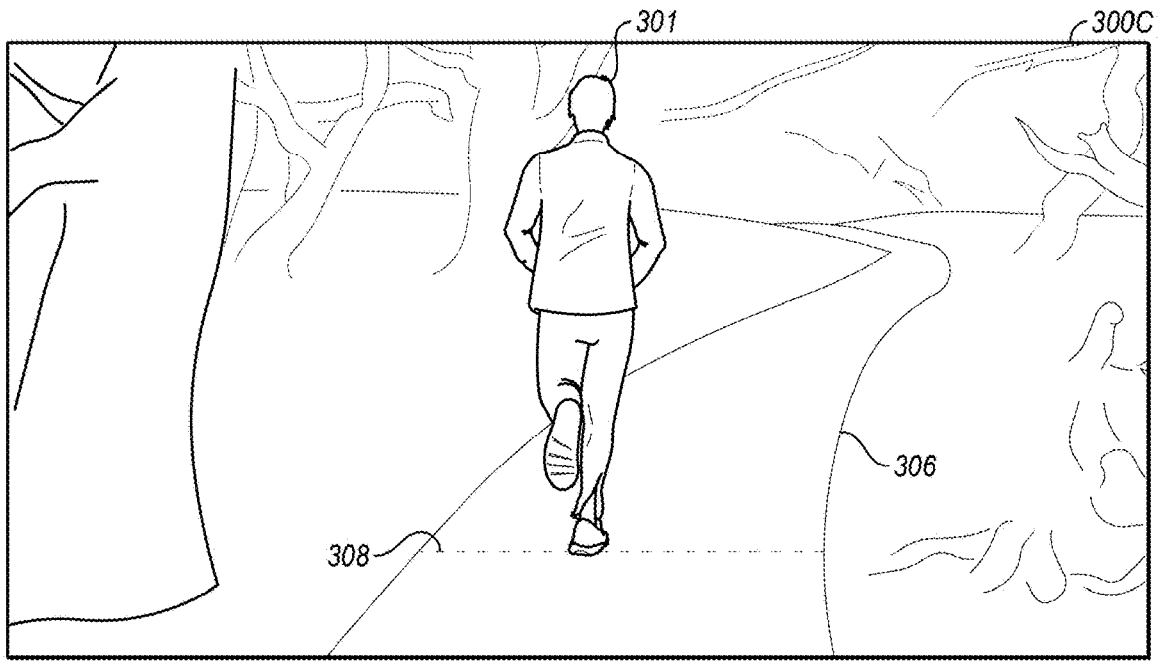

As disclosed in the frame 300C of FIG. 3C, the trainer 301 may continue performing the workout by running the marathon along the path 306. As disclosed in the data chart 302C, at the time that the frame 300C is captured by a video camera, 607 seconds may have transpired since the start of the workout (e.g. one additional second has transpired since the frame 300B was captured, and two additional seconds have transpired since the frame 300A was captured), the trainer 301 may now have slowed to running at a pace of 5 miles per hour up a 4.5% incline, the trainer 301 may still be in heart rate zone 3 but with an increased heart rate of 156 beats per minute, and may still be in a workout state of "In Workout." As illustrated in frame 300C, the trainer 301 may have crossed over the transition 308 in the path 306 where the incline transitions from the relatively gradual 0.5% incline to the relatively steep 4.5% incline, which may account for the slower speed and increased heart rate of the trainer 301. As disclosed in the CSV encoding chart 304C, the data parameters from the data chart 302C may be encoded into a CSV encoding 305C in a subtitle stream of a video, which is timed with the frame 300C, as "607,5,4.5,0,0,0,3,156,1".

Figure 3D:
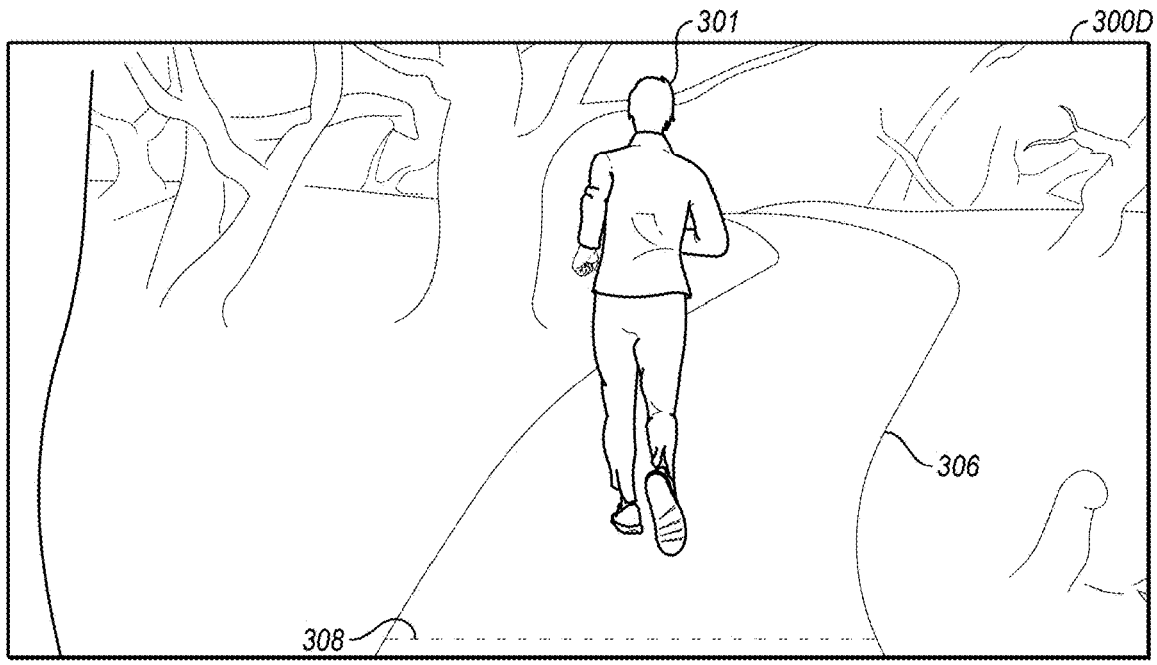

As disclosed in the frame 300D of FIG. 3D, the trainer 301 may continue performing the workout by running the marathon along the path 306. As disclosed in the data chart 302D, at the time that the frame 300D is captured by a video camera, 608 seconds may have transpired since the start of the workout (e.g. one additional second has transpired since the frame 300C was captured, two additional seconds have transpired since the frame 300B was captured, and three additional seconds have transpired since the frame 300A was captured), the trainer 301 may still be running at a pace of 5 miles per hour up a 4.5% incline, the trainer 301 may still be in heart rate zone 3 but with an increased heart rate of 160 beats per minute, and may still be in a workout state of "In Workout." As disclosed in the CSV encoding chart 304D, the data parameters from the data chart 302D may be encoded into a CSV encoding 305D in a subtitle stream of a video, which is timed with the frame 300D, as "608,5,4.5,0,0,0,3,160,1".

In some embodiments, the CSV encodings 305A, 305B, 305C, 305D or one or more of the values therein may be interpreted by the exercise machine that executes the video workout program that includes the video with the CSV encoding 305A, 305B, 305C, 305D as commands to set or maintain one or more operating parameters of the exercise machine. For example, for each CSV encoding 305A, 305B, 305C, 305D, the exercise machine may set or maintain the speed of the exercise machine at the value included in the CSV encoding 305A, 305B, 305C, 305D. As a more particular example, in response to receiving the video frames 300A, 300B with the CSV encodings 305A, 305B, the exercise machine may set or maintain the speed of the exercise machine (e.g., of its treadmill belt) at 6 mph, depending on whether the speed of the treadmill belt is already at 6 mph when the CSV encoding 305A, 305B is received. As another example, in response to receiving the video frame 300C with the CSV encoding 305C, the exercise machine may set the speed of the treadmill belt at 5 mph. As still another example, in response to receiving the video frame 300D with the CSV encoding 305D, the exercise machine may maintain the speed of the treadmill belt at 5 mph.

Due to the fact that, in a video, the frames 300A-300D from the video are timed with frames of the subtitle stream, the encoding of control commands in a subtitle stream, such as in the CSV encodings 305A-305D illustrated in the CSV encoding charts 304A-304D, maintains synchronization of the video of a video workout program and of corresponding control commands of the video workout program. For example, even if the video is buffered or otherwise delayed, the subtitle stream will also be buffered or otherwise delayed by an identical amount, which will maintain synchronization of the video and of corresponding control commands. This synchronization between a video and corresponding control commands in a video workout program can enable a user to become immersed in a workout on the exercise machine, which may help the user to avoid the boredom and burnout that is often experienced by users of exercise machines.

In some exercise machine systems, the video of a video workout program being executed at an exercise machine, such as represented by the frames 300A-300D, may be displayed only at the exercise machine, e.g., at a console of the exercise machine or a separate tablet directly coupled to the exercise machine. According to some embodiments herein, however, workout state may be maintained at the server 104 such that the video may be displayed at other displays that are not directly coupled to the exercise machine, such as at the network devices 118A-118C. In particular, by keeping state of the video workout program at the server 104, the server 104 may track the progress of the video as the video workout program is executed at the exercise machine and may share the video with any of the network devices 118A-118C synchronized to the state. Such a configuration may permit other users (who may be remote from the user) to follow the video progress on one or more of the network devices 118A-118C as the user performs the workout and/or may permit the user to display the video on one or more of the network devices 118A-118C.

Figure 3E:
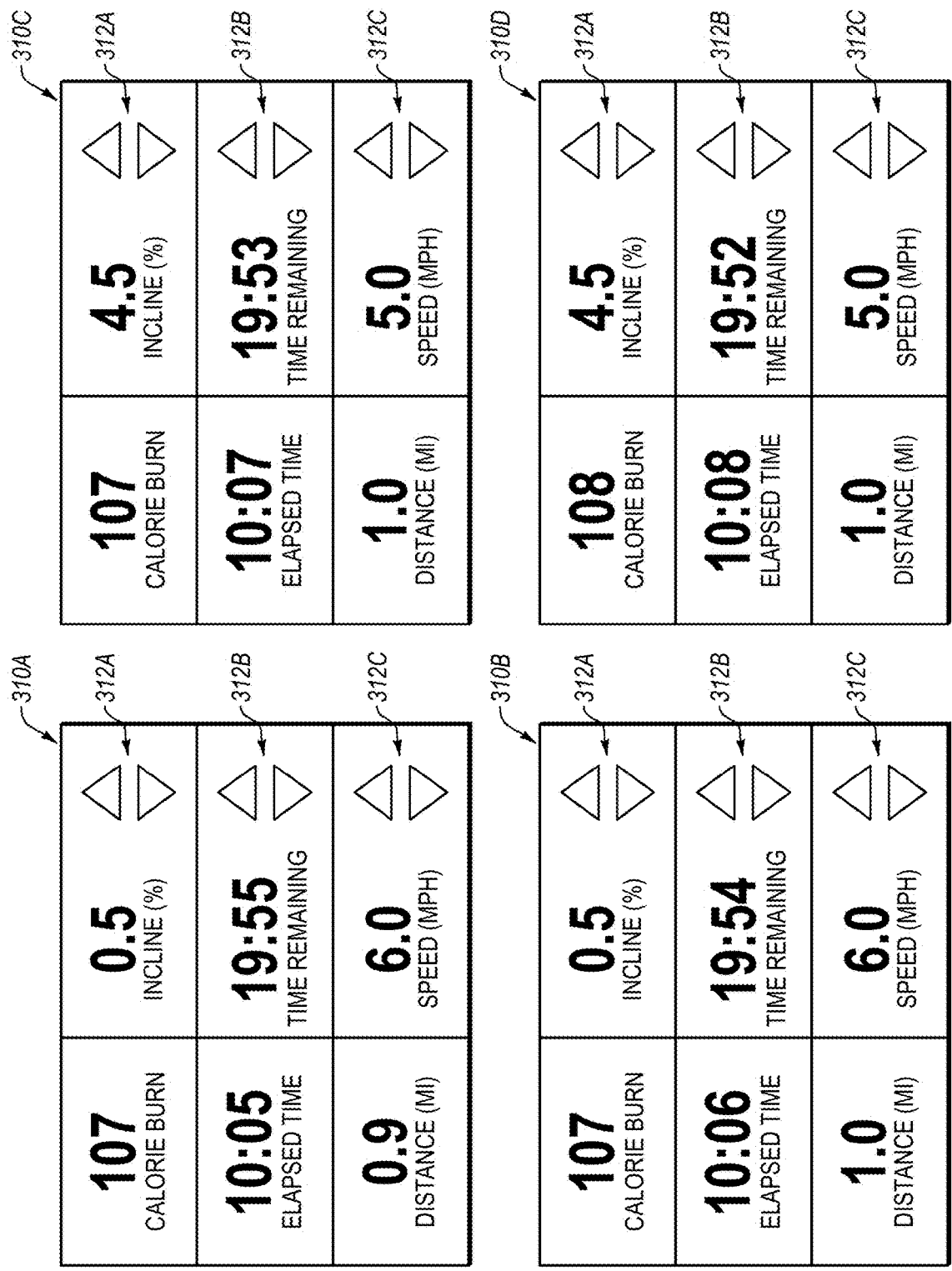
FIG. 3E illustrates frames of statistics views that may be displayed.

The frames 300A-300D are examples of video views of a video workout program that may be displayed, e.g., on the console 110 of the exercise machine 102 that executes the video workout program. FIG. 3E illustrates frames 310A-310D of statistics views that may be displayed, e.g., on the console 110 of the exercise machine 102 that executes the video workout program or other display. In more detail, the frame 310A includes workout statistics of the user performing the workout of the video workout program up to the point in time of the frame 300A of FIG. 3A, the frame 310B includes workout statistics up to the point in time of the frame 300B of FIG. 3B, the frame 310C includes workout statistics up to the point in time of the frame 300C of FIG. 3C, and the frame 310D includes workout statistics up to the point in time of the frame 300D of FIG. 3D. In some exercise machines, the video views represented by the frames 300A-300D of FIGS. 3A-3D and the statistics views represented by the frames 310A-310D of FIG. 3E may be mutually exclusive such that the user may choose to view the video view or the statistic view but not both at the same time. According to some embodiments herein, however, workout state may be maintained at the server 104 such that a video view of the video workout program may be displayed on a first display device (e.g., the console 110 or the network device 118A, 118B, 118C) while a statistics view of the video workout program may be simultaneously displayed on a second display device (e.g., a different one of the console 110 or the network device 118A, 118B, 118C) that is not directly connected to the first display device.

FIG. 3E further illustrates example workout controls 312A, 312B, 312C that may be displayed together with or separately from a statistics view. The workout controls 312A, 312B, 312C may be used to set or adjust one or more operating parameters of the exercise machine 102 that executes the video workout program. For example, the workout controls 312A may be configured to set or adjust the incline of the exercise machine 102 (e.g., of the treadmill deck 108B or the frame 108E). Alternatively or additionally, the workout controls 312B may be used to set or adjust a remaining amount of time in the video workout program. Alternatively or additionally, the workout controls 312C may be configured to set or adjust the speed of the exercise machine 102 (e.g., of the treadmill belt 108A). More generally, the workout controls 312A, 312B, 312C may include one or more workout controls to adjust one or more operating parameters of the exercise machine. Operating parameters of some exercise machines may be controllable only by workout controls on or integrated with the exercise machine (such as on the console 110) or on a directly connected device (such as the tablet 116). According to some embodiments herein, however, workout state may be maintained at the server 104 such that workout controls may be provided to a device that is not integrated with or directly connected to the exercise machine, such as the network devices 118A, 118B, 118C. In an example, the frames 310 may be displayed on a display device or other network device that is not integrated with or directly connected to the exercise machine, the user may operate one or more of the workout controls 312A, 312B, 312C on the display device that is not integrated with or directly connected to the exercise machine to manually adjust one or more operating parameters of the exercise machine, or equivalently a difficulty of the workout, the display device may provide one or more manual workout adjustments as inputs (entered using one or more of the workout controls 312A, 312B, 312C) to the server that maintains the state of the exercise machine, and the server may update the state and generate and send one or more corresponding exercise machine control commands and the adjusted workout difficulty to the exercise machine to adjust the difficulty of the workout according to the one or more manual workout adjustments and to display on the display of the exercise machine the adjusted workout difficulty.

Figure 4A:
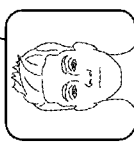
FIG. 4A illustrates a chart of heart rate zones for a user based on a resting heart rate and max heart rate of the user.

FIG. 4A illustrates a chart 400 of heart rate zones for the user 112 based on the resting heart rate and max heart rate of the user 112. The difference between the max heart rate and the resting heart rate of the user 112 is known as a heart rate reserve (HRR). Some embodiments may employ HRR to calculate heart rate zones, rather than using a simple percentage of max heart rate, which may allow for zones to be calculated just on the values that the heart of the user 112 is actual capable of beating at. As disclosed in the chart 400, the user 112 may have a measured or estimated resting heart rate of 65 beats per minute (BPM) as well as a measured or estimated max heart rate of 185 BPM. Based on these two data points, five heart rate zones for the user 112 may be calculated. In particular, as illustrated in the chart 400, each heart rate zone may be associated with a particular range of heart rates, such as 96-114 BPM for heart rate Zone 1, or 173-192 BPM for heart rate Zone 5. In some embodiments, prior to performing a video workout program, the resting heart rate as well as the max heart rate of a user may be obtained in order to calculate heart rate Zone 1 to heart rate Zone 5. Due to the fact that the resting heart rate and the max heart rate may vary from user to user, the calculated heart rate Zone 1 to heart rate Zone 5 may also vary from user to user.

In some embodiments, the resting heart rate and max heart rate in the chart 400 may be measured or estimated. For example, even though resting heart rate and max heart rate may be initially estimated for the user 112, the user 112 may be allowed to override the initial estimated values if the user 112 knows their resting heart rate or max heart rate. Further, instructions may be provided to the user 112 regarding how to properly measure or test their resting heart rate and/or max heart rate. For example, the treadmill 102A of FIG. 1 may be configured to provide a test that can be performed on the treadmill 102A to accurately test the max heart rate of the user 112. This may be a graded test that gets progressively harder until the user 112 hits their max heart rate. The user 112 may perform the test for as long as they can. When the user 112 ends the test, the treadmill 102A may automatically save the max heart rate of the user 112, and then recompute the heart rate zones shown in the chart 400 for the user 112. Similarly, anytime the user 112 adjusts their resting heart rate or max heart rate, the heart rate zones of the user 112 may be automatically shifted to reflect those new values. Also, it is noted that a max heart rate for any given user 112 may be different for different exercise modalities, such as for different exercise machines. For example, a max heart rate for the user 112 may be different on the stationary bike 102B than on the treadmill 102A. Therefore, for any given user 112, a different max heart rate may be used for different exercise modalities.

Figure 4B:
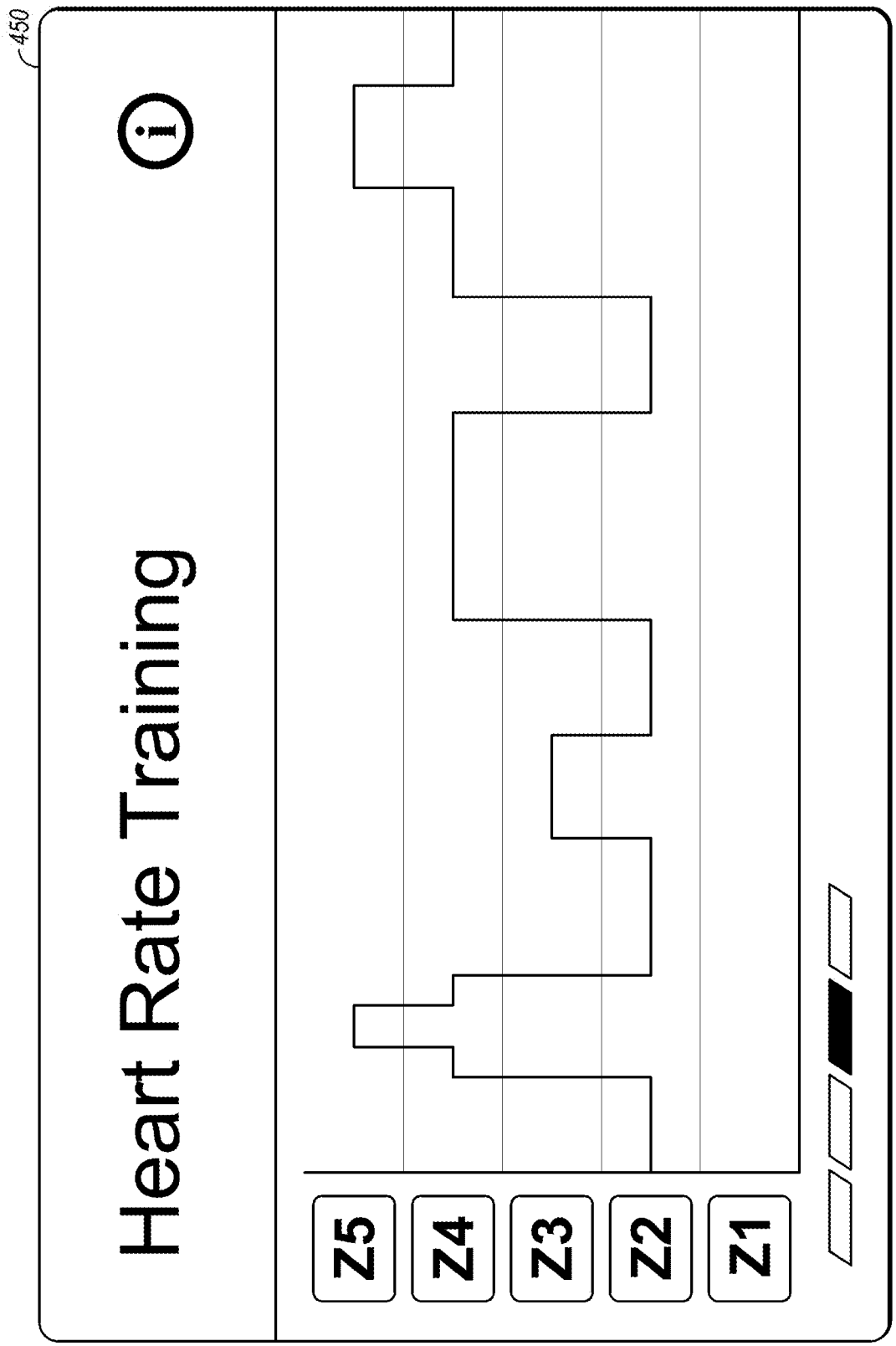
FIG. 4B illustrates a graph display of programmed heart rate zones for a video workout program

FIG. 4B illustrates a chart 450 of programmed heart rate zones for a video workout program. As disclosed in the chart 450, the video workout program may include multiple programmed heart rate zones (i.e., zone 2 to zone 5, or Z2 to Z5) corresponding to the depiction of the trainer in the video. In particular, the programmed heart rate zone transitions from zone 2, to zone 4, to zone 5, to zone 4, to zone 2, to zone 3, to zone 2, to zone 4, to zone 2, to zone 4, to zone 5, and to zone 4. Each of the transitions may occur at a particular time during the video workout program, and may correspond to a commensurate change in the heart rate zone of the trainer shown in the video of the video workout program. To enable the exercise machine to automatically and adaptively scale the current difficulty level of the video workout program so that the user's heart rate zone tracks closely to the programmed heart rate zones, the user's heart rate may be continually monitored. For example, the user's heart rate may be monitored by a heart rate sensor integrated with or communicatively coupled directly to the exercise machine or by a heart rate sensor included in a network device, such as network devices 118D, 118D. Further, the trends of the user's heart rate may also be taken into consideration to avoid the current difficulty level from being changed too often and/or too dramatically.

FIGS. 3A-3D illustrate video frames and charts that may be employed in controlling an exercise machine using exercise machine control commands of a video workout program. The exercise machine control commands may be encoded into a subtitle stream of a video of the video workout program or may be encoded separately from the video. In more detail, FIGS. 3A-3D illustrate frames 300A-300D of video captured by a videographer of a trainer 301 performing a workout, which may include running a marathon along a path 306. Further, FIGS. 3A-3D also illustrate data charts 302A-302D which contain certain relevant data parameters gathered during the workout at the same time that the corresponding frame of video is captured, manually or automatically using one or more sensors, for example. Finally, FIGS. 3A-3D also illustrate comma separated values (CSV) encoding charts 304A-304D showing how the data parameters from the data charts 302A-302D may be translated and encoded into control commands.

FIGS. 5A-5D illustrate video frames and data charts that may be employed in dynamically scaling a video workout program on an exercise machine based on heart rate monitoring. In particular, FIGS. 5A-5D illustrate frames 500A-500D of video captured by a videographer of the trainer 301 performing a workout, which may include running a marathon along a path 506. Further, FIGS. 5A-5D also illustrate data charts 502A-502D which contain certain relevant data parameters. These data parameters may be gathered during the workout at the same time that the corresponding frame of video is captured, or may be gathered at or around the time that the corresponding frame of video is displayed. The data parameters may be gathered manually, by listening to voice commands of the trainer 301 for example. These data parameters may alternatively be gathered automatically, using one or more sensors for example.

Finally, FIGS. 5A-5D also illustrate widgets 508A-508D and 510A-510D which may overlay the frames 500A-500D, respectively, when dynamic scaling based on heart rate monitoring is active during a workout. In some embodiments, the dynamic scaling can be toggled on and off by a user using, for example, a "Smart HR Training" control.

Further, in some embodiments, the chart 400 of FIG. 4A may be displayed when a user selects the header of any of the widgets 508A-508D or 510A-510D.

The frames 500A-500D of a video, which show the trainer 301 running the marathon, represent frames of video captured over time. It is understood, however, that other intervening frames of video may also be captured between each of the frames 500A-500D, resulting in a captured video having additional frames (e.g., with a frame rate of 24, 30, or 60 frames per second).

As disclosed in the frame 500A of FIG. 5A, the trainer 301 may be performing a workout by running a marathon along the path 506. As disclosed in the data chart 502A, at the time that the frame 500A is captured by the video camera, the trainer 301 may be performing, and/or may direct that a user perform, the workout at a current programmed heart rate zone of zone 2, which for the user 112 of FIG. 4A corresponds to a personalized current programmed heart rate zone range of 115-134 BPM. As illustrated in the heart rate training widget 508A and in the data chart 502A, the previous programmed heart rate zone was zone 4, the time since the workout began is 450 seconds, the time since the most recent zone change is 70 seconds, the time remaining in the current programmed heart rate zone is 50 seconds, and the time remaining in the workout is 1350 seconds. As disclosed in the data chart 502A, the heart rate monitoring rate is once per second, the threshold heart rate trend rate is −5 seconds, the warmup time threshold is 180 seconds, and the user's last ten actual heart rates (in BPM) are 122, 122, 123, 123, 124, 124, 125, 124, 125, and 125. Also disclosed in the data chart 502A, the baseline difficulty level is $B_0$ with a baseline speed of 4 MPH, while the current difficulty level is $B_2$ with a current speed of 4.3 MPH. Finally, the data chart 502A also discloses that the user's actual heart rate is 125 BPM, which corresponds to the user's actual heart rate zone of zone 2, and the user's actual heart rate zone range of 115-134 BPM. Some or all of the data in data chart 502A may be employed to determine that the current difficulty level of the video workout program, of which the frame 500A is a part, should not be dynamically scaled because the user is already performing in the proper zone (i.e., zone 2).

As disclosed in the frame 500B and data chart 502B of FIG. 5B, the trainer 301 may be performing, and/or may direct that a user perform, the workout at a current programmed heart rate zone of zone 3, which for the user 112 of FIG. 4A corresponds to a personalized current programmed heart rate zone range of 135-153 BPM. As illustrated in the heart rate training widget 508B and in the data chart 502B, the previous programmed heart rate zone was zone 2, the time since the workout began is 675 seconds, the time since the most recent zone change is 60 seconds, the time remaining in the current programmed heart rate zone is 60 seconds, and the time remaining in the workout is 1125 seconds. As disclosed in the data chart 502B, the heart rate monitoring rate is once per second, the threshold heart rate trend rate is +4 seconds, the warmup time threshold is 180 seconds, and the user's last ten actual heart rates (in BPM) are 152, 152, 153, 153, 154, 154, 155, 155, 155, and 155. Also disclosed in the data chart 502B, the baseline difficulty level is $B_0$ with a baseline speed of 6 MPH, while the current difficulty level is $B_2$ with a current speed of 6.7 MPH. Finally, the data chart 502B also discloses that the user's actual heart rate is 155 BPM, which corresponds to the user's actual heart rate zone of zone 4, and the user's actual heart rate zone range of 154-172 BPM. Some or all of the data in data chart 502B may be employed to determine that the current difficulty level of the video workout program, of which the frame 500B is a part, should be dynamically scaled downward to move the user into the proper zone (i.e., from heart rate zone 4 to heart rate zone 3).

As disclosed in the frame 500C and data chart 502C of FIG. 5C, the trainer 301 may be performing, and/or may direct that a user perform, the workout at a current programmed heart rate zone of zone 2, which for the user 112 of FIG. 4A corresponds to a personalized current programmed heart rate zone range of 115-134 BPM. As illustrated in the heart rate training widget 508C and in the data chart 502C, the previous programmed heart rate zone was zone 3, the time since the workout began is 810 seconds, the time since the most recent zone change is 50 seconds, the time remaining in the current programmed heart rate zone is 70 seconds, and the time remaining in the workout is 990 seconds. As disclosed in the data chart 502C, the heart rate monitoring rate is once per second, the threshold heart rate trend rate is −4 seconds, the warmup time threshold is 180 seconds, and the user's last ten actual heart rates (in BPM) are 131, 131, 132, 133, 133, 134, 135, 136, 136, and 137. Also disclosed in the data chart 502C, the baseline difficulty level is $B_0$ with a baseline speed of 4 MPH, while the current difficulty level is $B_1$ with a current speed of 4.2 MPH. Finally, the data chart 502c also discloses that the user's actual heart rate is 137 BPM, which corresponds to the user's actual heart rate zone of zone 3 and the user's actual heart rate zone range of 135-153 BPM. Some of all of the data in data chart 502C may be employed to determine that the current difficulty level of the video workout program, of which the frame 500C is a part, should be dynamically scaled downward to move the user into the proper zone (i.e., from heart rate zone 3 to heart rate zone 2).

As disclosed in the frame 500D and data chart 502D of FIG. 4D, the trainer 301 may be performing, and/or may direct that a user perform, the workout at a current programmed heart rate zone of zone 4, which for the user 112 of FIG. 4A corresponds to a personalized current programmed heart rate zone range of 154-172 BPM. As illustrated in the heart rate training widget 508D and in the data chart 502D, the previous programmed heart rate zone was zone 2, the time since the workout began is 1020 seconds, the time since the most recent zone change is 120 seconds, the time remaining in the current programmed heart rate zone is 120 seconds, and the time remaining in the workout is 780 seconds. As disclosed in the data chart 502D, the heart rate monitoring rate is once per second, the threshold heart rate trend rate is +5 seconds, the warmup time threshold is 180 seconds, and the user's last ten actual heart rates (in BPM) are 148, 147, 148, 149, 149, 149, 150, 150, 150, and 150. Also disclosed in the data chart 502D, the baseline difficulty level is $B_0$ with a baseline speed of 8 MPH, and the current difficulty level is also $B_0$ with a current speed of 8 MPH. Finally, the data chart 502D also discloses that the user's actual heart rate is 150 BPM, which corresponds to the user's actual heart rate zone of zone 3, and the user's actual heart rate zone range of 135-153 BPM. Some or all of the data in data chart 502D may be employed to determine that the current difficulty level of the video workout program, of which the frame 500B is a part, should be dynamically scaled upward to move the user into the proper zone (i.e., from heart rate zone 3 to heart rate zone 4).

During the video workout program in which the heart rate training widget 508A-508D are displayed to the user 112, two states are displayed, namely, (1) a programmed state 509 which displays the programmed heart rate zone for the entire video workout program, and (2) a historical state 511A-511D which shows the historical heart rate zone (and/or the corresponding heart rate) of the user from the beginning of the video workout program to the current point in time in the video workout program. These two displayed states enable the user to track their actual heart rate performance (using the historical state 511A-511D) against the programmed heart rate performance (using the programmed state 509) for the video workout program.

During the video workout program in which the frames 500A-500D from the video are displayed to the user 112, the current difficulty level may be dynamically scaled based on the monitored heart rate of the user 112 of FIG. 4A. However, due to the fact that the direction and speed at which the heart rate of the user 112 is trending is also being continually monitored, the video workout program may avoid changing the current difficulty level too often and/or too dramatically. Thus, the enjoyment of the user 112 may be increased, the inadvertent operation of the exercise machine (e.g., the treadmill 102A of FIG. 1) at a difficulty level that is not optimal for the fitness level of the user 112 may be avoided, and the integrity between the workout of the trainer 301 shown in the frames 500A-500D from the video and the actual workout performed by the user 112 can be maintained, thus increasing the ability of the user 112 to become more immersed in the workout on the exercise machine.

Figure 6:
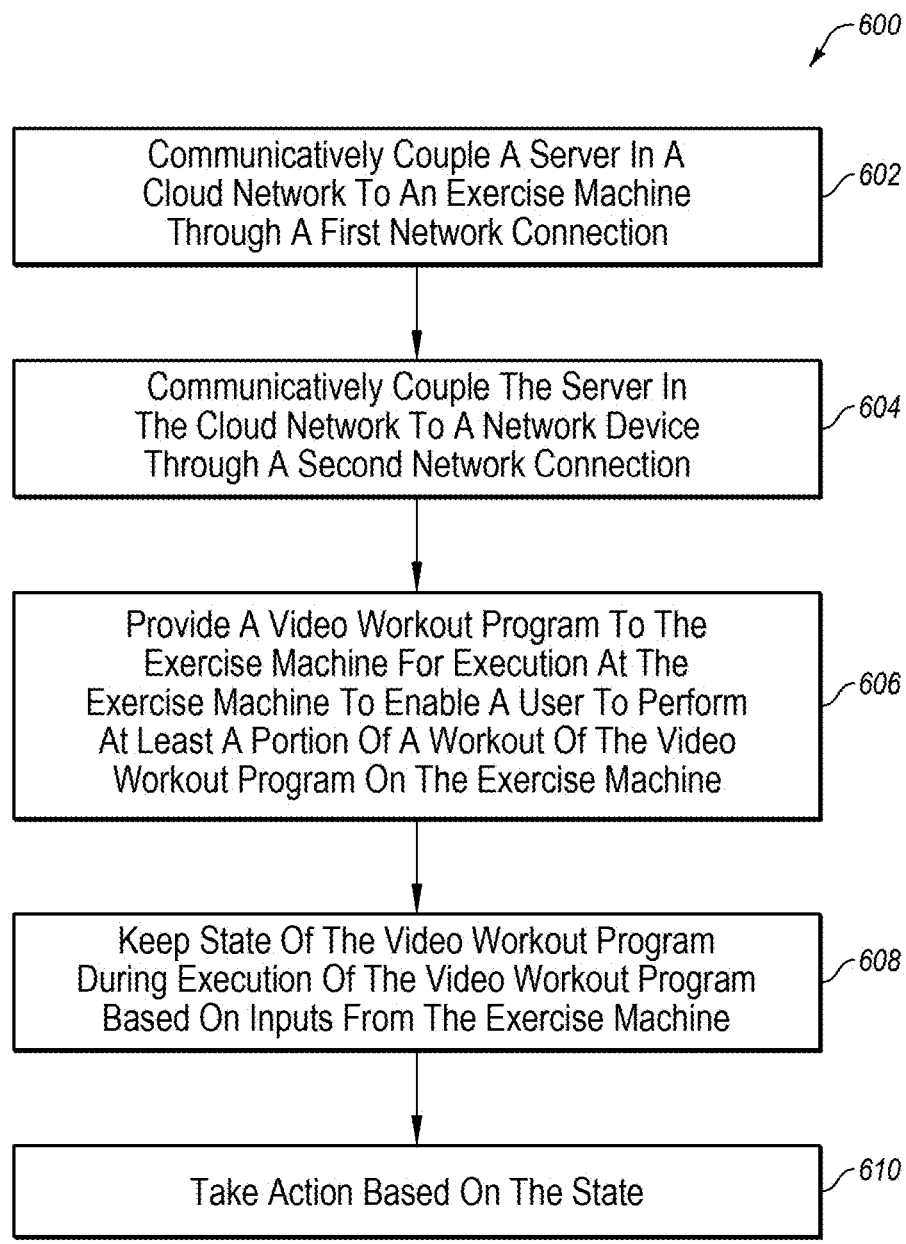
FIG. 6 illustrates a flowchart of an example method that involves keeping state of a video workout program.

FIG. 6 illustrates a flowchart of an example method 600 that involves keeping state of a video workout program. The method 600 may be performed, in some embodiments, by one or more applications, devices, or systems, such as by the server 104, the exercise machine 102, the tablet 116, the network device 118, or some combination thereof, and/or other applications, devices, or systems herein. In these and other embodiments, the method 600 may be performed by one or more processors based on one or more computer-readable instructions stored on one or more non-transitory computer-readable media. The method 600 will now be described in connection with FIGS. 1-5D.

The method 600 may include, at action 602, communicatively coupling a server in a cloud network to an exercise machine through a first network connection. For example, action 602 may include communicatively coupling the server 104 in a cloud network to the exercise machine 102 through a first network connection. The first network connection may include any suitable network connection that allows the server 104 and the exercise machine 102 to exchange data. Communicatively coupling the server to the exercise machine may involve or implement any suitable network protocol and may include one or more steps performed by the server in establishing the first network connection. In some implementations, the exercise machine to which the server is connected may include a display, such as the display that may be integrated or included in the console 110 of the exercise machine 102.

The method 600 may include, at action 604, communicatively coupling the server in the cloud network to a network device through a second network connection. For example, action 604 may include communicatively coupling the server 104 in the cloud network to the one (or more) of the network devices 118. The second network connection may include any suitable network connection that allows the server 104 and the network device 118 to exchange data. Communicatively coupling the server to the network device may involve or implement any suitable network protocol and may include one or more steps performed by the server in establishing the second network connection. The network device to which the server is communicatively coupled through the second network connection may include a second display, a heart rate monitor, or other network device. More specifically, action 604 may include communicatively coupling the server in the cloud network to a second display such as may be implemented as or included in any of the network devices 118A-118C. Alternatively or additionally, action 604 may specifically include communicatively coupling the server in the cloud network to a heart rate monitor such as may be implemented as or included in the network devices 118D, 118E. In some embodiments, the network device may be located in proximity to the exercise machine without being directly communicatively coupled to the exercise machine.

The method 600 may include, at action 606, the server providing a video workout program to the exercise machine for execution at the exercise machine to enable a user to perform at least a portion of a workout of the video workout program on the exercise machine. For example, the server 104 may provide a saved or live video workout program to the exercise machine 102 for execution at the exercise machine 102 to enable the user 112 to perform at least a portion of a workout of the video workout program on the exercise machine 102.

The method 600 may include, at action 608, the server keeping state of the video workout program during execution of the video workout program based on inputs from at least the exercise machine. Alternatively or additionally, the server may keep state further based on inputs from the network device and/or multiple network devices. For example, the server 104 may keep state of the video workout program during execution of the video workout program based on inputs from the exercise machine 102 and/or the network device 118.

The method 600 may include, at action 610, taking action based on the state. For example, action 610 may include the server generating an exercise machine control command based on the state and the server providing the exercise machine control command over the first network connection to the exercise machine to control an actuator of the exercise machine according to the exercise machine control command.

The method 600 may further include receiving input indicative of the user performing at least a second portion of the workout off of the exercise machine and updating workout data included in the state to reflect performance of the second portion of the workout off of the exercise machine, wherein at least some of the updated workout data is displayed on the first display of the exercise machine. For example, the workout may include a first portion (e.g., a first exercise modality) that takes place on the exercise machine (e.g., a treadmill) and a second portion (e.g., a different exercise modality) that takes place off of the exercise machine on a different exercise machine (e.g., a stationary bike), with different equipment (e.g., weights), and/or no equipment at all (e.g., yoga). Performance of the second portion of the workout may be tracked by the network device, the exercise machine itself (e.g., by a camera or other sensor of the exercise machine), another exercise machine, or other device and provided to the server to update workout data of the state. The updated workout data/state may be shared by the server with the exercise machine, the network device, or other device.

In some embodiments, the method 600 may further include synchronizing a first display of the exercise machine with a second display of the network device based on the state. For instance, a display of the console 110 of the exercise machine 102 may be synchronized with a display of one or more of the network devices 118A-118C. The synchronizing based on the state may include distributing workout data of the video workout program that is displayed on the first display of the exercise machine, received from the exercise machine, and updated in the state to the network device for display on the second display of the network device. Alternatively or additionally, the synchronizing based on the state may include providing one or more workout controls (such as network controls 312 of FIG. 3E) to the network device for display on the second display; receiving as one or more of the inputs from the network device a manual workout adjustment to adjust a difficulty of the workout entered using the one or more workout controls; generating an exercise machine control command to adjust the difficulty of the workout according to the manual workout adjustment; sending the exercise machine control command to the exercise machine for implementation at the exercise machine; updating the state to include the adjusted workout difficulty; and sending the adjusted workout difficulty to the exercise machine for display on the first display of the exercise machine.

Alternatively or additionally, the portion of the workout may be a first portion performable on the exercise machine and the workout may further include a second portion performable off the exercise machine (e.g., on a different machine, with different equipment, and/or without any exercise machine or equipment at all). The first portion of the workout may include a first exercise modality and the second portion of the workout may include a second exercise modality that is different than the first exercise modality. In some embodiments, the second portion of the workout is performable with a second exercise machine and the method further includes communicatively coupling the server in the cloud network to the second exercise machine through a third network connection and the server further keeping state of the video workout program during execution of the video workout program based on inputs from the second exercise machine.

The method 600 may further include the server generating a second exercise machine control command based on the state and the server providing the second exercise machine control command over the third network connection to the second exercise machine to control an actuator of the second exercise machine according to the second exercise machine control command.

In some embodiments, the method 600 may further include communicatively coupling the server in the cloud network to a heart rate monitor coupled to a user through a third network connection and the server further keeping state of the video workout program during execution of the video workout program based on inputs from the heart rate monitor. For example, in addition to the server 104 being communicatively coupled to one or more of the network devices 118A-118C through the second network connection, the server 104 may be communicatively coupled to one or more of the heart rate monitors 118D, 118E through the third network connection. In this and other embodiments, the method 600 further include adaptively scaling the video workout program on the exercise machine based on the state. In particular, the heart rate monitor may report heart rate measurements to the server and the server may adaptively scale the workout based on the reported heart rate, including generating exercise machine control commands to send to the exercise machine to adjust a difficulty of the workout at the exercise machine based on the heart rate measurements, e.g., as generally described with respect to FIGS. 4A-5D.

Referring again to FIG. 6, in some embodiments of the method 600, the exercise machine includes the first display, the server is communicatively coupled to the second display, and the action 510 may include the server synchronizing the second display with the first display of the exercise machine based on the state.

In some embodiments, the second display may be located in proximity to the exercise machine without being directly communicatively coupled to the exercise machine.

In some embodiments, the synchronizing based on the state includes distributing workout data of the video workout program that is displayed on the first display of the exercise machine, received from the exercise machine, and updated in the state to the second display for display on the second display.

In some embodiments, the synchronizing based on the state includes providing one or more workout controls to the second display for display on the second display; receiving from the second display a manual workout adjustment to adjust a difficulty of the workout entered using the one or more workout controls, where the server generates and sends to the exercise machine an exercise machine control command to adjust the difficulty of the workout according to the manual workout adjustment; updating the state to include the adjusted workout difficulty; and sending the adjusted workout difficulty to the exercise machine for display on the first display of the exercise machine.

Referring again to FIG. 6, in some embodiments of the method 600, the network device includes a heart rate monitor, such as one of the heart rate monitors 118D, 118E and action 510 may include the server adaptively scaling the video workout program based on the state.

In some embodiments, the heart rate monitor may be located in proximity to the exercise machine without being directly communicatively coupled to the exercise machine.

In some embodiments, the inputs from the heart rate monitor include heart rate measurements of the user over time and the adaptively scaling may include periodically determining from the heart rate measurements at least one of: that an actual heart rate zone of the user is not equal to a current programmed heart rate zone; or that the actual heart rate of the user is not trending toward the current programmed heart rate zone; and in response to the periodically determining, adjusting a current difficulty level of the video workout program to adjust the user's actual heart rate zone toward the current programmed heart rate zone. The adjusting may include adjusting the current difficulty level upward if the actual heart rate zone is lower than the current programmed heart rate zone and downward if the actual heart rate zone is higher than the current programmed heart rate zone.

Alternatively or additionally, the adaptively scaling may further include the server generating an exercise machine control command to adjust the current difficulty level based on the state and the adjusting the current difficulty level may include the server providing the exercise machine control command over the first network connection to the exercise machine to control an actuator of the exercise machine according to the exercise machine control command.

Figure 7:
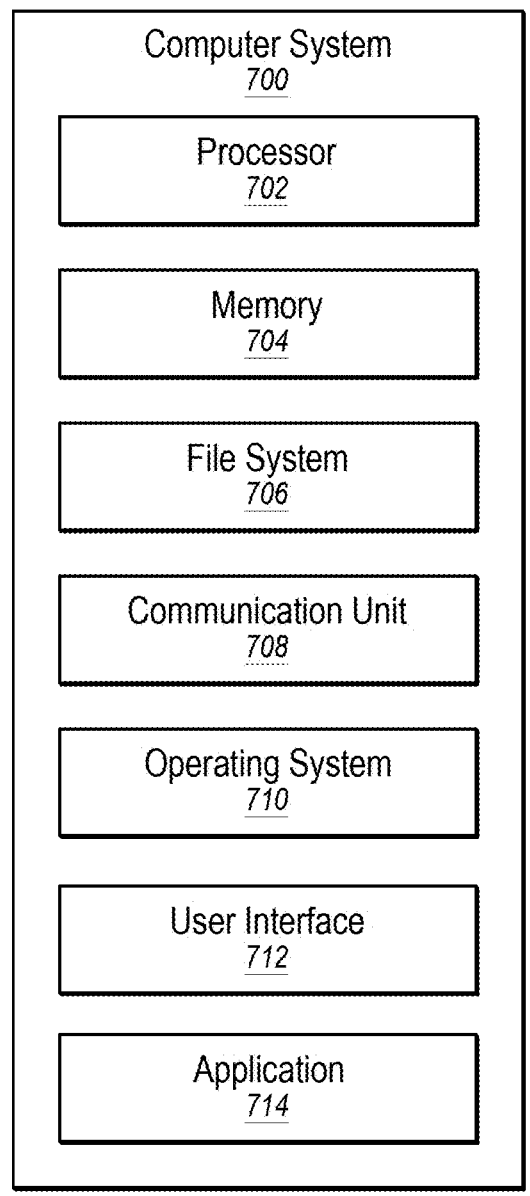
FIG. 7 illustrates an example computer system that may be employed in keeping state of a video workout program.

FIG. 7 illustrates an example computer system 700 that may be employed in keeping state of a video workout program. Alternatively or additionally, the computer system 700 may be employed in controlling an exercise machine using a video workout program, and/or in other methods or systems described herein. In some embodiments, the computer system 700 may be part of any of the systems or devices described in this disclosure. For example, the computer system 700 may be part of any of the server 104, the exercise machine 102, the console 110, the tablet 116, or the network device 118 of FIG. 1.

The computer system 700 may include a processor 702, a memory 704, a file system 706, a communication unit 708, an operating system 710, a user interface 712, and an application 714, which all may be communicatively coupled. In some embodiments, the computer system may be, for example, a desktop computer, a client computer, a server computer, a mobile phone, a laptop computer, a smartphone, a smartwatch, a tablet computer, a portable music player, an exercise machine console, a video camera, or any other computer system.

Generally, the processor 702 may include any suitable special-purpose or general-purpose computer, computing entity, or processing device including various computer hardware or software applications and may be configured to execute instructions stored on any applicable computer-readable storage media. For example, the processor 702 may include a microprocessor, a microcontroller, a digital signal processor (DSP), an application-specific integrated circuit (ASIC), a Field-Programmable Gate Array (FPGA), or any other digital or analog circuitry configured to interpret and/or to execute program instructions and/or to process data, or any combination thereof. In some embodiments, the processor 702 may interpret and/or execute program instructions and/or process data stored in the memory 704 and/or the file system 706. In some embodiments, the processor 702 may fetch program instructions from the file system 706 and load the program instructions into the memory 704. After the program instructions are loaded into the memory 704, the processor 702 may execute the program instructions. In some embodiments, the instructions may include the processor 702 performing or controlling performance of one or more actions of the method 600 of FIG. 6.

The memory 704 and the file system 706 may include computer-readable storage media for carrying or having stored thereon computer-executable instructions or data structures. Such computer-readable storage media may be any available non-transitory media that may be accessed by a general-purpose or special-purpose computer, such as the processor 702. By way of example, and not limitation, such computer-readable storage media may include non-transitory computer-readable storage media including Read-Only Memory (ROM), Electrically Erasable Programmable Read-Only Memory (EEPROM), Compact Disc Read-Only Memory (CD-ROM) or other optical disk storage, magnetic disk storage or other magnetic storage devices, flash memory devices (e.g., solid state memory devices), or any other storage media which may be used to carry or store desired program code in the form of computer-executable instructions or data structures and which may be accessed by a general-purpose or special-purpose computer. Combinations of the above may also be included within the scope of computer-readable storage media. Computer-executable instructions may include, for example, instructions and data configured to cause the processor 702 to perform a certain operation or group of operations, such as one or more actions of the method 600 of FIG. 6. These computer-executable instructions may be included, for example, in the operating system 710, in one or more applications, or in some combination thereof.

The communication unit 708 may include any component, device, system, or combination thereof configured to transmit or receive information over a network, such as the network 106 of FIG. 1. In some embodiments, the communication unit 708 may communicate with other devices at other locations, the same location, or even other components within the same system. For example, the communication unit 708 may include a modem, a network card (wireless or wired), an infrared communication device, a wireless communication device (such as an antenna), and/or chipset (such as a Bluetooth device, an 802.6 device (e.g., Metropolitan Area Network (MAN)), a WiFi device, a WiMax device, a cellular communication device, etc.), and/or the like. The communication unit 708 may permit data to be exchanged with a network and/or any other devices or systems, such as those described in the present disclosure.

The operating system 710 may be configured to manage hardware and software resources of the computer system 700 and configured to provide common services for the computer system 700.

The user interface 712 may include any device configured to allow a user to interface with the computer system 700. For example, the user interface 712 may include a display, such as an LCD, LED, or other display, that is configured to present video, text, application user interfaces, and other data as directed by the processor 702. The user interface 712 may further include a mouse, a track pad, a keyboard, a touchscreen, volume controls, other buttons, a speaker, a microphone, a camera, any peripheral device, or other input or output device. The user interface 712 may receive input from a user and provide the input to the processor 702. Similarly, the user interface 712 may present output to a user.

The application 714 may be one or more computer-readable instructions stored on one or more non-transitory computer-readable media, such as the memory 704 or the file system 706, that, when executed by the processor 702, is configured to perform one or more actions of the method 600 of FIG. 6. In some embodiments, the application 714 may be part of the operating system 710 or may be part of an application of the computer system 700, or may be some combination thereof.

Figure 8:
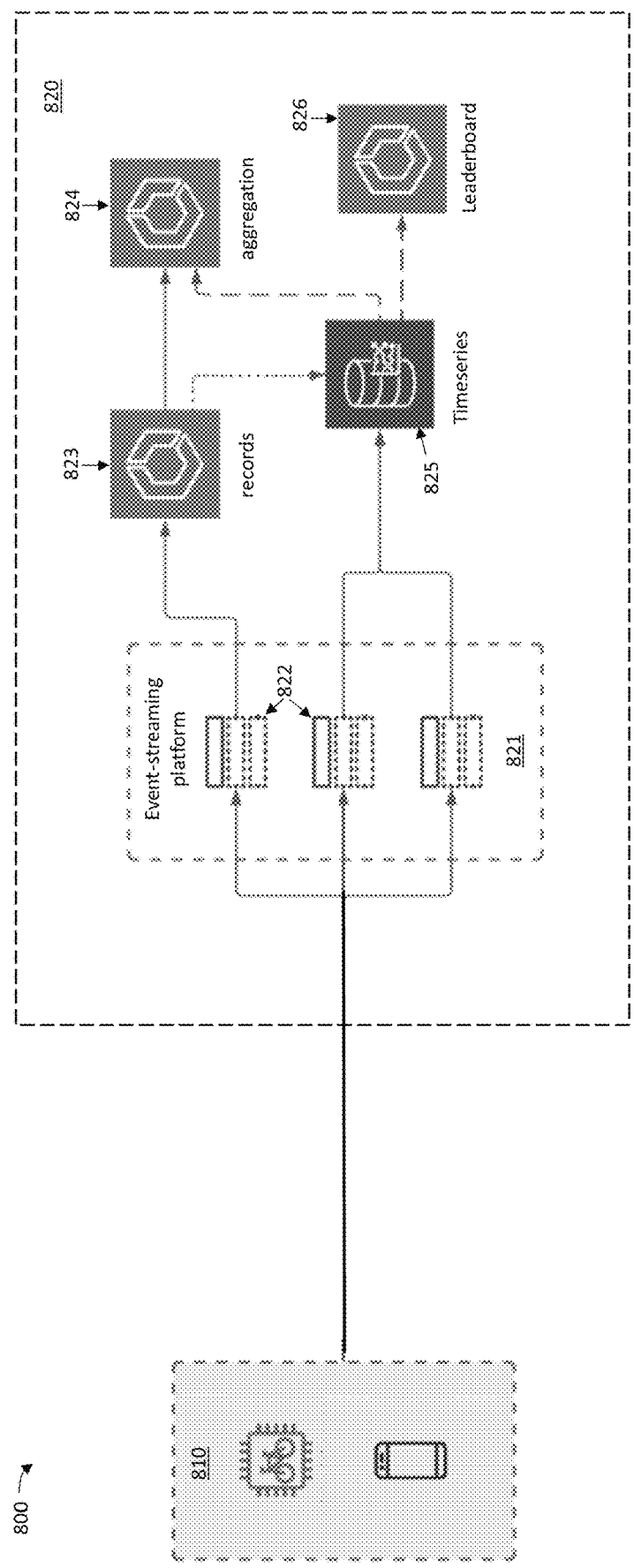
FIG. 8 illustrates another example exercise machine system including server elements.

FIG. 8 illustrates another example exercise machine system 800 including server elements. The exercise machine system 800 may include devices 810 and a server 820. The devices 810 may be similar to the exercise machines 102 and network devices 118 of FIG. 1. The server 820 may be similar to the server 104 of FIG. 1.

The devices 810 may include exercise machines, devices capable of streaming a video workout program, and/or devices configured to capture performance metrics. Exercise machines may include exercise bikes, treadmills, ellipticals, stair-steppers, rowers, and other exercise machines. The devices 810 may receive a video workout program from the server 820 The devices 810 may display a video of the video workout program on displays of the devices 810. The devices 810 may control moveable or moving members of the devices according to exercise machine control commands included in the video workout program, as discussed herein. The devices 810 may synchronize changes in parameters of the devices 810 with changes in the video of the video workout program. The devices 810 may capture performance metrics of a user performing a workout of the video workout program using one or more sensors. The performance metrics may include a speed, resistance, incline, cadence, workout duration, and other performance metrics. The devices 810 may transmit a stream of performance metrics to the server 820.

The server 820 may receive the stream of performance metrics from the devices 810. The server 820 may include an event-streaming platform 821 which receives the stream of performance metrics from the devices 810. An event-streaming platform is a software program for rapidly processing events. An event may be a datum which needs to be processed. Event-streaming platforms may include instructions for how the event is processed, by which processors of the server 820 the event is processed, and in what order the processors process the event. Event-streaming platforms may separate events into topics based upon type of event. A topic is a log of events. For example, a speed of a treadmill belt of 5 mph at 3:26 into a workout may be an event which is sent from the devices 810 to the event-streaming platform 821. The event-streaming platform 821 may assign the event to a speed topic. The event-streaming platform 821 may direct the speed of the treadmill belt with its associated time to be processed by one or more processors of the server 820. The event-streaming platform 821 may direct all events in the speed topic to be processed by the same one or more processors of the server 820. An example of an event-streaming platform is KAFKA.

In some embodiments, the server 820 may be multiple different servers. The event-streaming platform 821 may run on the multiple different servers. The multiple different servers may provide redundancy to prevent data loss. The event-streaming platform 821 may run across the multiple different servers so that the computing and memory resources of the multiple different servers are available to the event-streaming platform 821.

The event-streaming platform 821 may include topics 822 which receive portions of the stream of performance metrics. In some embodiments, the portions of the stream of performance metrics include tags which determine which topic of the topics 822 each portion of the stream of performance metrics is received by. In other embodiments, the devices 810 publish different portions of the stream of performance metrics to different topics 822 of the event-streaming platform.

The event-streaming platform 821 may send the portions of the stream of performance metrics to various modules running on the server. Modules are programs, services, agents, or a combination of multiple programs, services, and agents running on the server 820. The modules discussed herein may exist as non-transitory computer-readable instructions stored on the server 820. In some embodiments, the modules discussed herein are separate programs, services, or agents. In other embodiments, the modules are portions of a single program configured to process workout data.

The records module 823 may receive a portion of the stream of performance records from the event-streaming platform. The records module 823 may compile a record of the workout performed by the user based on the received portion of the stream of performance metrics. The records module may transmit the record of the workout performed to an aggregation module 824. In some embodiments, the aggregation module 824 may combine records of a plurality of users to compile a general record of the video workout program. In other embodiments, the aggregation module 824 may combine the records of the plurality of users to determine aggregate statistics for the video workout program.

The timeseries module 825 may generate a timeseries database of the performance metrics based on the received portion of the stream of performance metrics. The timeseries database may associate the performance metrics with time values. The timeseries module 825 may add the values of the performance metrics to the timeseries database as the portions of the stream of performance metrics are received. The timeseries module 825 may continuously update the timeseries database. The timeseries module 825 may continuously transmit the timeseries database to the aggregation module 824. The aggregation modules 824 may use the timeseries database in calculating updated aggregate statistics for the video workout program.

The timeseries module 825 may transmit the timeseries database to a leaderboard module 826. The leaderboard module 826 may, using the timeseries database, compare performance metrics of different users to dynamically rank the different users relative to each other in real time. The leaderboard module 826 may generate a real-time visual representation of the dynamic ranking of the users and transmit the visual representation to the devices 810. The visual representation may be a leaderboard graphical user interface. The records module 823 may transmit completed records of user performance of users who previously performed the video workout program to the timeseries module 825. The timeseries module 825 may generate the timeseries database using the completed records and transmit the timeseries database including the completed records to the leaderboard module 826. The leaderboard module 826 may compare the real-time performance metrics of current users performing the workout to performance metrics from the completed records of previous users who previously performed the workout to dynamically rank the current users and the previous users. The leaderboard module 826 may generate the visual representation of the dynamic ranking of the current users and the previous users and transmit the visual representation to the devices 810. The visual representation may be a leaderboard showing previous users and current users.

The technical advantage of using completed records from the records module 823 in generating the time series database is that the leaderboard module 826 may generate a leaderboard from a single, unified time series database. The leaderboard module 826 may compare user performance at any moment with the performance of the current users and the previous users due to the timeseries database being generated using completed records. A practical application of these technical improvements is a workout class which may be taken by different exercisers at different times. Using the technical improvements discussed herein, an exerciser can compete against all other exercisers taking the workout class at the time the exerciser is taking the class and against all exercisers who have previously taken the class.

Figure 9:
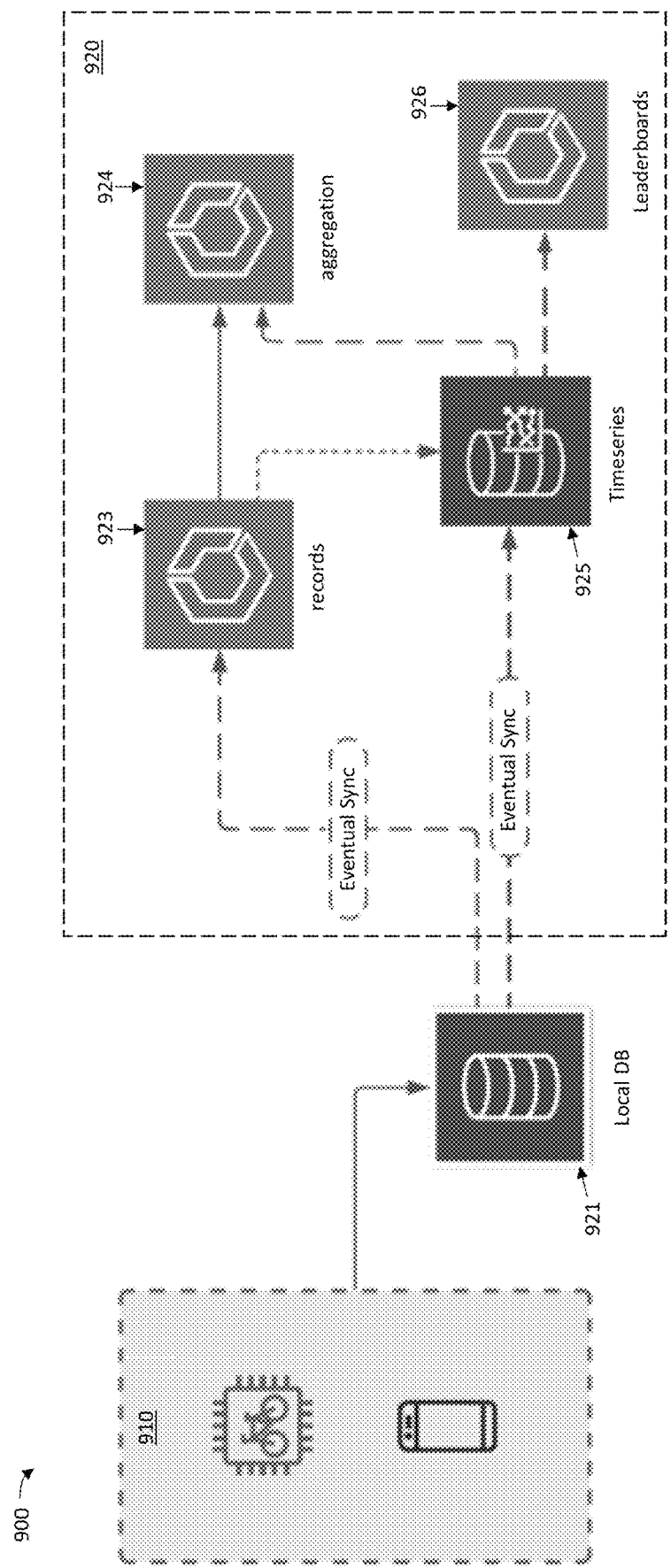
FIG. 9 illustrates another example exercise machine system including server elements.

FIG. 9 illustrates another example exercise machine system 900 including server elements. The exercise machine system 900 may include devices 910 and a server 920. The devices 910 may be similar to the devices 810 of FIG. 8. The server 920 may be similar to the server 820 of FIG. 8.

The exercise machine system 900 may include a local database 921. The devices 910 may be connected via a local connection. The local connection may be a wired or wireless connection, such as Bluetooth. The devices 910 may each store a copy of the local database 921 on a memory of each device. The local database 921 may be synchronized between the devices 910 using the local connection. The local database 921 may store performance metrics of a user performing a video workout program. The user may perform the video workout program using the devices 910. For example, the user may perform a first portion of the video workout program on a treadmill and a second portion of the video workout program on an exercise bike. In another example, the user may perform a first portion of the video workout program on a rower and a second portion of the video workout program on a mat with the video of the video workout program displayed on a smartphone.

A state of the workout may be kept on the local database 921 such that the video workout program is synchronized between the devices 910. For example, the video workout program may be displayed on a display of a treadmill and on a display of an exercise bike, with the video, exercise machine control commands, and audio of the video workout program synchronized on the devices. The devices 910 may capture performance metrics of the user as the user performs the video workout program.

The devices 910 may synchronize the local database 921 with the server 920 to update the state of the workout on the server 920. The devices 910 may query a network connection with the server 920 and synchronize the local database 921 with the server 920 when a network connection exists between the devices 910 and the server 920. The local database 921 may synchronize with one or more databases on the server such as a timeseries database of a timeseries module 925 and a records database of a records module 923.

Maintaining the local database 921 on the devices 910 solves the technical problem of delays in the video workout program due to network connection issues between the devices 910 and the server 920 by offering the technical improvement of executing the video workout program locally on the devices 910 while synchronizing the state of the video workout program with the server 920. Synchronizing the local database 921 between the devices 910 solves the technical problem of maintaining the state of the video workout program between multiple devices by offering the technical improvement of multiple synchronized copies of the local database 921 which each represent the state of the video workout program. The synchronization of the local database 921 and the server 920 when a network connection exists between the devices 910 and the server 920 solves the technical problem of keeping the state of the workout between devices of multiple users for purposes of dynamic ranking and aggregate statistics by offering continuous comparison of performance metrics of a local user when a network connection exists and allowing the local user, when a network connection does not exist, to perform the workout and generate performance statistics for comparison once a network connection is reestablished. A practical application of these technical improvements is a workout class which is performed on multiple exercise machines and which compares the performance of participants in the workout class. An exerciser may transition seamlessly between the multiple exercise machines, with the exerciser's performance metrics on each machine being recorded and combined in a unified record for comparison against the performance metrics of other exercisers. Even if the multiple exercise machines lose a network connection to the server, the unified record of the exerciser is still updated and can be sent to the server for comparison against the performance metrics of other exercisers once the network connection is restored.

In some embodiments, a first copy of the local database 921 is designated as a master copy. Conflicts between copies of the local database 921 on the devices 910 are resolved in favor of the master copy. Synchronization between the local database 921 and the server 920 is performed using the master copy. In some embodiments, the master copy is a copy of the local database 921 on a particular device of the devices 910. In other embodiments, the master copy is a copy of the local database 921 on a current device which is currently capturing performance metrics of the user. Designating the copy of the local database 921 on the current device as the master copy allows for updates to the local database 921 to be controlled by whichever device of the devices 910 is currently capturing performance metrics. For example, a copy of the local database 921 on a treadmill may be designated as the master copy while the user is using the treadmill and a copy of the local database 921 on an exercise bike may be designated as the master copy while the user is using the exercise bike.

Designating the exercise machine which is currently capturing performance metrics offers the technical improvement of more reliable capture of performance metrics and reduced use of computational resources in resolving conflicts between copies of the local database.

Figure 10:
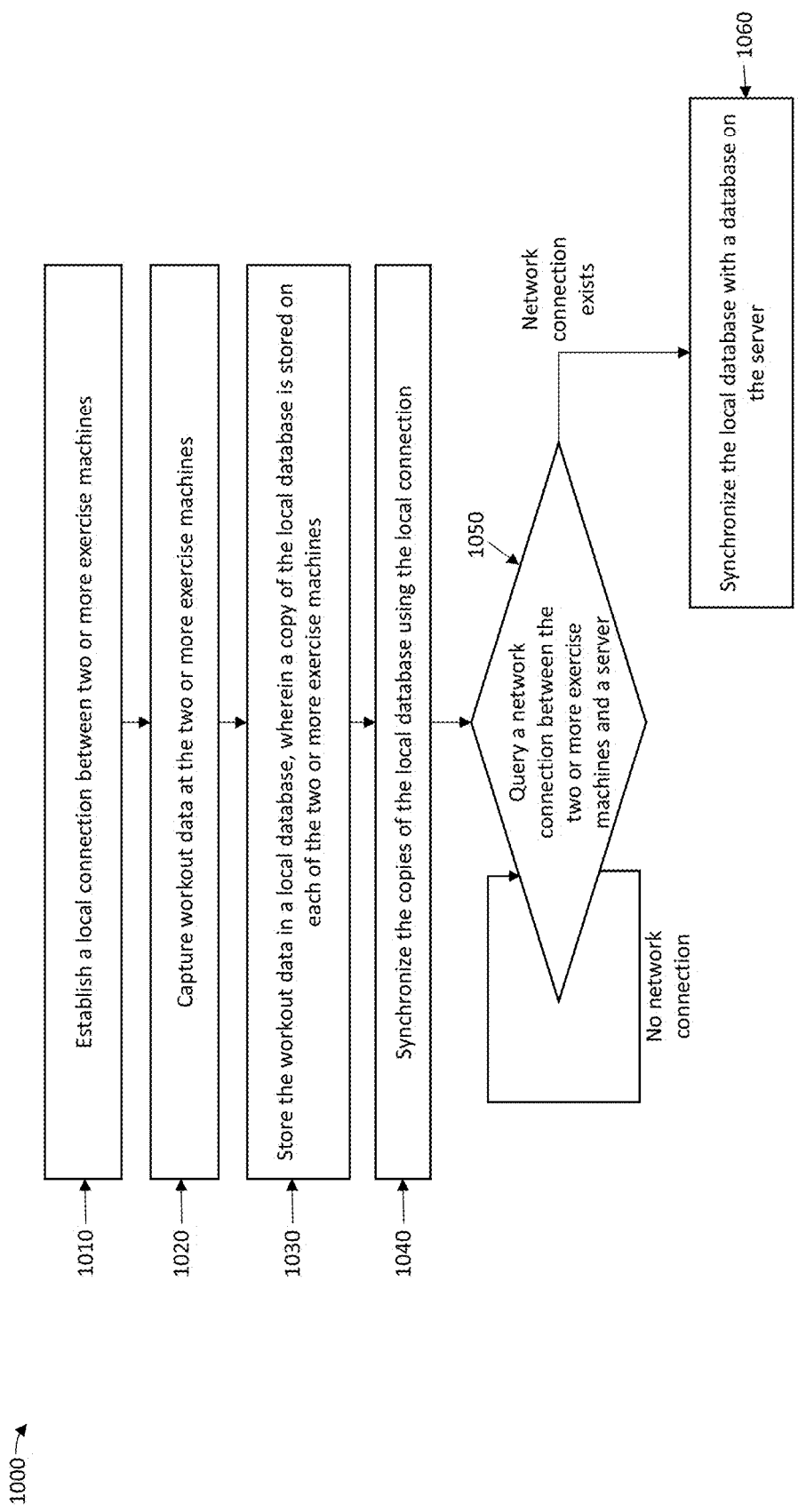
FIG. 10 illustrates an example flow chart illustrating operations for keeping a workout state in a local database synchronized with a server database.

FIG. 10 illustrates an example flow chart 1000 illustrating operations for keeping a workout state in a local database synchronized with a server database. Additional, fewer, or different operations may be performed in the method, depending on the embodiment. Further, the operations may be performed in the order shown, concurrently, or in a different order.

At 1010, a local connection is established between two or more exercise machines. The local connection may be a wired connection or a wireless connection. In some embodiments, the local connection is a Bluetooth connection. Establishing the local connection may require a first exercise machine of the two or more exercise machines to send a signal to a second exercise machine of the two or more exercise machines identifying the first exercise machine.

At 1020, the two or more exercise machines capture workout data. The two or more exercise machines may capture the workout data using one or more sensors of the two or more exercise machines. For example, a first exercise machine of the two or more exercise machines may be a treadmill and a second exercise machine of the two or more exercise machines may be an exercise bike. The first exercise machine may capture a speed and incline of a belt and the second exercise machine may capture a resistance and a cadence of pedaling.

At 1030, the workout data is stored in a local database, wherein a copy of the local database is stored on each of the two or more exercise machines. The local database may include workout data from each of the two or more workout devices. The local database may be continuously updated as workout data is captured. Workout data may be captured on a first exercise machine of the two more exercise machines during a first portion of the video workout program. Workout data may be captured on a second exercise machine of the two more exercise machines during a second portion of the video workout program. The local database may be updated with workout data from the first exercise machine during the first portion. The local database may be updated with workout data from the second exercise machine during the second portion.

At 1040, the copies of the local database are synchronized using the local connection. The copies of the local database may be synchronized so that each copy is the same. This means that each copy of the local database contains the same data as the other copies. Synchronizing the copies of the local database ensures that the copies of the local database are true copies of one another. The copies of the local database may be continuously synchronized to keep state of the workout on the two or more exercise machines.

At 1050, the two or more exercise machines may query a network connection between the two or more exercise machines and a server. The network connection may be over a network, such as the internet. The server may be remote from the two or more exercise machines. If a network connection between the two or more exercise machines and the server does not exist or does not meet or exceed a threshold connectivity, the two more exercise machines may continue to query the network connection. If a network connection between the two or more exercise machines and the server exists or meets or exceeds a threshold connectivity, the two more exercise machines may synchronize the local database with a database on the server at 1060. Synchronizing the local database with a server database may update the state of the workout on the server. The sever database may receive workout data from the local database during the synchronization of the local database with the server database. The server database may be updated to include workout data captured and stored in the local database since a most recent synchronization with the local database.

Maintaining the local database on the two or more exercise machines solves the technical problem of delays in the video workout program due to network connection issues between the two or more exercise machines and the server by offering the technical improvement of executing the video workout program locally on the two or more exercise machines while synchronizing the state of the video workout program with the server. The local execution of the video workout program ensures that there are no delays in the video workout program due to network connection interruptions. Synchronizing the local database 921 between the two or more exercise machines solves the technical problem of maintaining the state of the video workout program between multiple devices by offering the technical improvement of multiple synchronized copies of the local database 921 which each represent the state of the video workout program. Synchronizing the copies of the local database ensures that each device of the multiple devices maintains the state of the workout. The synchronization of the local database 921 and the server 920 when a network connection exists between the two or more exercise machines and the server 920 solves the technical problem of keeping the state of the workout between devices of multiple users for purposes of dynamic ranking and aggregate statistics by offering continuous comparison of performance metrics of a local user when a network connection exists and allowing the local user, when a network connection does not exist, to perform the workout and generate performance statistics for comparison once a network connection is reestablished.

A practical application of these technical improvements is a workout class which is performed on multiple exercise machines and which compares the performance of participants in the workout class. An exerciser may transition seamlessly between the multiple exercise machines, with the exerciser's performance metrics on each machine being recorded and combined in a unified record for comparison against the performance metrics of other exercisers. Even if the multiple exercise machines lose a network connection to the server, the unified record of the exerciser is still updated and can be sent to the server for comparison against the performance metrics of other exercisers once the network connection is restored.

INDUSTRIAL APPLICABILITY

Various modifications to the embodiments illustrated in the drawings will now be disclosed.

Some example methods disclosed herein synchronize a video workout program across multiple devices. A server in a cloud network may be communicatively coupled to an exercise machine through a first network connection and to a network device through a second network connection. The server may provide a video workout program to the exercise machine for execution at the exercise machine to enable a user to perform at least a portion of a workout of the video workout program on the exercise machine. The server may keep state of the video workout program during execution of the video workout program based on inputs from the exercise machine and the network device that is not directly communicatively coupled to the exercise machine. The state may include workout parameters of the user, operating parameters of the exercise machine, or the like. The server may take some action based on the state. For example, the server may generate an exercise machine control command based on the state and may provide the exercise machine control command to the exercise machine to control an actuator of the exercise machine according to the exercise machine control command. Alternatively or additionally, the server may synchronize a display of a network device that is not directly communicatively coupled to the exercise machine with a display of the exercise machine based on the state. Alternatively or additionally, the server may adaptively scale the video workout program based on the state.

According to some embodiments, by maintaining workout state in the cloud, the video workout program or multiple views thereof may be simultaneously displayed on multiple display devices at least some of which are not directly communicatively coupled to the exercise machine, inputs from one or more network devices may be used to set or adjust a difficulty of the video workout program at the exercise machine, and/or workout statistics may be tracked for mixed modality workouts that are not performed exclusively on or with the exercise machine.

For example, keeping state at the server may permit a first display of the exercise machine to be synchronized with a second display of the network device based on the state. Synchronizing based on the state may include distributing workout data of the video workout program that is displayed on the first display of the exercise machine, received from the exercise machine, and updated in the state to the network device for display on the second display of the network device. Thus, the workout data may be simultaneously, or substantially simultaneously, displayed on both the first display of the exercise machine and the second display of the network device. The user may have possession of and/or access to the network device such that the user may simultaneously see multiple views of the video workout program, e.g., on two different display devices. Alternatively or additionally, another individual may have possession of and/or access to the network device to, e.g., follow progress of the user as the user performs the workout. In a similar manner, a video of the video workout program may be displayed on multiple displays simultaneously and/or on one or more displays that are not directly communicatively coupled to the exercise machine. For example, the server may track a progress of the video or the video workout program while the video workout program is executed at the exercise machine, keeping video progress as part of the state. The server may stream or otherwise provide the video of the video workout program to the network device synchronized to the progress of the video or the video workout program where the video may be displayed on the network device. If the user has possession of and/or access to the network device, the user may view the video on the second display of the network device synchronized to the progress of the video workout program while simultaneously viewing another view, e.g., a workout statistics view, on the first display of the exercise machine.

Alternatively or additionally, the synchronizing based on the state may include providing one or more workout controls to the network device for display on the second display of the network device. The workout controls may include actuable icons, such as up/down arrows or other icons, displayable on and actuable from a touchscreen display, or other workout controls actuable in some other manner (e.g., mouse input). The server may receive as input from the network device a manual workout adjustment to adjust a difficulty of the workout entered using the one or more workout controls. For example, the manual workout adjustment may increase or decrease treadmill belt speed, treadmill deck angle, stationary bike resistance, stationary bike frame angle, and/or other operating parameter of the corresponding exercise machine that may affect workout difficulty. The server may generate an exercise machine control command to adjust the difficulty of the workout according to the manual workout adjustment and may send the exercise machine control command to the exercise machine for implementation at the exercise machine. The server may also update the state to include the adjusted workout difficulty. The state may be updated after the server receives the input from the network device, after the server generates the exercise machine control command, after the server sends the exercise machine control command to the exercise machine, and/or after receiving confirmation from the exercise machine that the exercise machine control command has been executed at the exercise machine. Confirmation from the exercise machine may include explicit confirmation (e.g., a message confirming the exercise machine control command has been executed) or implicit confirmation (e.g., a periodic report (e.g., once every second or more or less frequently) of the current operating parameters of the exercise machine which may reflect execution of the exercise machine control command). The server may also send the adjusted workout difficulty (e.g., an adjusted exercise machine operating parameter) to the exercise machine for display on the first display of the exercise machine. Alternatively, the exercise machine itself may update the workout difficulty displayed on the first display in response to executing the exercise machine control command and without receiving and/or without the server ever sending the adjusted workout difficulty to the exercise machine.

Keeping state of a video workout program as described herein may allow workout statistics to be tracked for mixed modality workouts that are not performed exclusively on or with a single exercise machine. For example, the workout of a video workout program may include multiple portions, such as first and second portions, where the first portion is performable on the exercise machine and the second portion is performable off the exercise machine, optionally on another exercise machine or with other equipment or no equipment at all. The first portion may include a first exercise modality and the second portion may include a different second exercise modality. The server may receive input indicative of the user performing at least the second portion of the workout off of the exercise machine and updating workout data included in the state to reflect performance of the second portion of the workout off of the exercise machine. At least some of the updated workout data may be displayed on the first display of the exercise machine. In some embodiments, the input indicative of the user performing the second portion of the workout off of the exercise machine may be received from the network device (e.g., a heart rate monitor) or other device not in direct communication with the exercise machine and the method may further include distributing at least some of the updated workout data to the exercise machine for display on the first display of the exercise machine. Alternatively or additionally, the input indicative of the user performing the second portion of the workout off of the exercise machine may be received from the exercise machine, e.g., from a video camera or other sensor of the exercise machine that captures data indicative of the user performing the second portion of the workout off of the exercise machine. Alternatively or additionally, the input indicative of the user performing the second portion of the workout off of the exercise machine may be received from a second exercise machine or other exercise equipment, such as smart weights. For example, the server may track which exercise machine the user is using at any given time to switch between exercise machines for different portions of a workout. As an example, each exercise machine may identify the user (or collect enough data to identify the user) when the user begins using the exercise machine or at other time(s) and report the user's identity (or the data to identify the user) to the server so the server can both know which exercise machine the user is using (and control it accordingly) and update workout state of the workout that includes multiple exercise modalities. The exercise machines may identify the user in any of a variety of ways, such as scanning the user (e.g., the user's irises, fingerprints, or the like) or a device associated with the user (e.g., a smartphone of the user, an RFID tag, an NFC tag, a heart rate monitor or other sensor worn by the user), requiring a user login, or other method. Alternatively or additionally, the user may identify which exercise machines the user is using at any given time by logging in to each exercise machine when beginning use, by scanning a QR code or other identifier of the exercise machine with the user's phone (which may then report the identity of the exercise machine to the server), or the like. In some implementations, each user may be associated with one or more device IDs or UIDs of sensors of the user. Thus, an exercise machine may pair to or communicate with one or more sensors in proximity to the exercise machine to determine a corresponding device ID or UID and report the device ID or UID to the server. The server may maintain a table or other data structure that associates device IDs or UIDs with users and may search the table or other data structure for the received device ID or UID. When the device ID or UID is found in the table or other data structure, the corresponding user associated with the device ID or UID may be determined from the table or other data structure.

In embodiments in which the second portion of the workout is performable on the second exercise machine, the server may be communicatively coupled to the second exercise machine through a third network connection and may further keep state of the video workout program during execution of the video workout program based on inputs from the second exercise machine. The server may generate exercise machine control commands to control the first exercise machine, the second exercise machine, or both, based on the state and may provide the corresponding exercise machine control commands to the corresponding exercise machines for execution thereat. For example, if the state indicates the user has moved on from the first portion of the workout performable on the first exercise machine to the second portion of the workout performable on the second exercise machine, the server may generate a first exercise machine control command to, e.g., pause the treadmill belt of the first exercise machine if it's a treadmill, and a second exercise machine control command to, e.g., set a workout difficulty of the second portion of the workout on the second exercise machine to a given difficulty level. As another example, if the state indicates the user has moved on from the second portion of the workout performable on the second exercise machine to a third portion of the workout performable on the first exercise machine, the server may generate a third exercise machine control command to, e.g., pause or terminate operation of the second exercise machine, and a fourth exercise machine control command to, e.g., resume operation of the first exercise machine.

In embodiments in which the network device is a heart rate monitor or in which the server is further communicatively coupled to a heart rate monitor, the server may keep (or further keep) state of the video workout program during execution of the video workout program based on inputs from the heart rate monitor. For example, the state may be updated based on ongoing measurements or other data from the heart rate monitor. In particular, the state may be updated based on, e.g., heart rate measurements, to reflect current measurements of the user's actual heart rate and/or heart rate zone, which may be used as described with respect to, e.g., FIGS. 4A-5D, to adaptively scale the video workout program at the exercise machine. Further, the adaptively scaling may be performed without the heart rate monitor being directly communicatively coupled to the exercise machine.

The heart rate measurements may be received at the server periodically (e.g., once every second), over time, or the like. Adaptively scaling may include periodically determining from the heart rate measurements at least one of: that an actual heart rate zone of the user is not equal to a current programmed heart rate zone; or that the actual heart rate of the user is not trending toward the current programmed heart rate zone. In response to the periodically determining, the server may adjust a current difficulty level of the video workout program to adjust the user's actual heart rate zone toward the current programmed heart rate zone. For example, the adjusting may include adjusting the current difficulty level upward if the actual heart rate zone is lower than the current programmed heart rate zone and downward if the actual heart rate zone is higher than the current programmed heart rate zone.

In some embodiments, the server may be communicatively coupled to multiple network devices over different network connections. The server may update state based on inputs from one or more of the network devices. Alternatively or additionally, outputs on one or more of the network devices may be synchronized to the state kept at the server. For example, workout data accumulated in the state may be distributed to one or more of the network devices for display thereat.

Unless specific arrangements described herein are mutually exclusive with one another, the various implementations described herein can be combined to enhance system functionality or to produce complementary functions. Likewise, aspects of the implementations may be implemented in standalone arrangements. Thus, the above description has been given by way of example only and modification in detail may be made within the scope of the present invention.

In accordance with common practice, the various features illustrated in the drawings may not be drawn to scale. The illustrations presented in the present disclosure are not meant to be actual views of any particular apparatus (e.g., device, system, etc.) or method, but are merely example representations that are employed to describe various embodiments of the disclosure. Accordingly, the dimensions of the various features may be arbitrarily expanded or reduced for clarity. In addition, some of the drawings may be simplified for clarity. Thus, the drawings may not depict all of the components of a given apparatus (e.g., device) or all operations of a particular method.

Terms used herein and especially in the appended claims (e.g., bodies of the appended claims) are generally intended as "open" terms (e.g., the term "including" should be interpreted as "including, but not limited to," the term "having" should be interpreted as "having at least," the term "includes" should be interpreted as "includes, but is not limited to," etc.).

Additionally, if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations.

In addition, even if a specific number of an introduced claim recitation is explicitly recited, it is understood that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." or "one or more of A, B, and C, etc." is used, in general such a construction is intended to include A alone, B alone, C alone, A and B together, A and C together, B and C together, or A, B, and C together, etc. For example, the use of the term "and/or" is intended to be construed in this manner.

Further, any disjunctive word or phrase presenting two or more alternative terms, whether in the summary, detailed description, claims, or drawings, should be understood to contemplate the possibilities of including one of the terms, either of the terms, or both terms. For example, the phrase "A or B" should be understood to include the possibilities of "A" or "B" or "A and B."

Additionally, the use of the terms "first," "second," "third," etc., are not necessarily used herein to connote a specific order or number of elements. Generally, the terms "first," "second," "third," etc., are used to distinguish between different elements as generic identifiers. Absence a showing that the terms "first," "second," "third," etc., connote a specific order, these terms should not be understood to connote a specific order. Furthermore, absence a showing that the terms "first," "second," "third," etc., connote a specific number of elements, these terms should not be understood to connote a specific number of elements. For example, a first widget may be described as having a first side and a second widget may be described as having a second side. The use of the term "second side" with respect to the second widget may be to distinguish such side of the second widget from the "first side" of the first widget and not to connote that the second widget has two sides.

The foregoing description, for purpose of explanation, has been described with reference to specific embodiments. However, the illustrative discussions above are not intended to be exhaustive or to limit the invention as claimed to the precise forms disclosed. Many modifications and variations are possible in view of the above teachings. The embodiments were chosen and described to explain practical applications, to thereby enable others skilled in the art to utilize the invention as claimed and various embodiments with various modifications as may be suited to the particular use contemplated.

A. A method to synchronize a video workout program across multiple devices, the method comprising:
- communicatively coupling a server in a cloud network to an exercise machine through a first network connection;
- communicatively coupling the server in the cloud network to a network device through a second network connection;
- the server providing a video workout program to the exercise machine for execution at the exercise machine to enable a user to perform at least a portion of a workout of the video workout program on the exercise machine;
- the server keeping state of the video workout program during execution of the video workout program based on inputs from the exercise machine and the network device;
- the server generating an exercise machine control command based on the state; and
- the server providing the exercise machine control command over the first network connection to the exercise machine to control an actuator of the exercise machine according to the exercise machine control command.

B. The method of section A, further comprising:
- receiving input indicative of the user performing at least a second portion of the workout off of the exercise machine; and
- updating workout data included in the state to reflect performance of the second portion of the workout off of the exercise machine, wherein at least some of the updated workout data is displayed on the first display of the exercise machine.

C. The method of section B, wherein:
- the input indicative of the user performing the second portion of the workout off of the exercise machine is received from the network device or other device not in direct communication with the exercise machine; and
- the method further comprises distributing the at least some of the updated workout data to the exercise machine for display on the first display of the exercise machine.

D. The method of section B, wherein the input indicative of the user performing the second portion of the workout off of the exercise machine is received from the exercise machine.

E. The method of any one of sections A-D, wherein the network device is located in proximity to the exercise machine without being directly communicatively coupled to the exercise machine.

F. The method of any one of sections A-E, further comprising synchronizing a first display of the exercise machine with a second display of the network device based on the state.

G. The method of section F, wherein the synchronizing based on the state comprises distributing workout data of the video workout program that is displayed on the first display of the exercise machine, received from the exercise machine, and updated in the state to the network device for display on the second display of the network device.

H. The method of section F, wherein the synchronizing based on the state comprises:

providing one or more workout controls to the network device for display on the second display;
receiving as one or more of the inputs from the network device a manual workout adjustment to adjust a difficulty of the workout entered using the one or more workout controls;
generating an exercise machine control command to adjust the difficulty of the workout according to the manual workout adjustment;
sending the exercise machine control command to the exercise machine for implementation at the exercise machine; and
updating the state to include the adjusted workout difficulty;
wherein the exercise machine displays the adjusted workout difficulty on the first display of the exercise machine.

I. The method of any one of sections A-H, wherein the portion of the workout comprises a first portion performable on the exercise machine, the workout further comprising a second portion performable off the exercise machine, wherein the first portion of the workout comprises a first exercise modality and the second portion of the workout comprises a second exercise modality that is different than the first exercise modality.

J. The method of section I, wherein:
the second portion of the workout is performable with a second exercise machine; and
the method further comprises:
communicatively coupling the server in the cloud network to the second exercise machine through a third network connection; and
the server further keeping state of the video workout program during execution of the video workout program based on inputs from the second exercise machine.

K. The method of section J, further comprising:
the server generating a second exercise machine control command based on the state; and
the server providing the second exercise machine control command over the third network connection to the second exercise machine to control an actuator of the second exercise machine according to the second exercise machine control command.

L. The method of any one of sections A-K, further comprising:
communicatively coupling the server in the cloud network to a heart rate monitor coupled to a user through a third network connection; and
the server further keeping state of the video workout program during execution of the video workout program based on inputs from the heart rate monitor.

M. The method of section L, further comprising adaptively scaling the video workout program on the exercise machine based on the state.

N. The method of section M, wherein:
the inputs from the heart rate monitor include heart rate measurements of the user over time; and
the adaptively scaling comprises:
periodically determining from the heart rate measurements at least one of:
that an actual heart rate zone of the user is not equal to a current programmed heart rate zone; or
that the actual heart rate of the user is not trending toward the current programmed heart rate zone; and
in response to the periodically determining, adjusting a current difficulty level of the video workout program to adjust the user's actual heart rate zone toward the current programmed heart rate zone.

O. The method of section N, wherein the adjusting comprises adjusting the current difficulty level:
upward if the actual heart rate zone is lower than the current programmed heart rate zone; and
downward if the actual heart rate zone is higher than the current programmed heart rate zone.

P. A non-transitory computer-readable medium having computer-executable instructions stored thereon that are executable by a processing unit to perform or control performance of the method of any one of sections A-O.

Q. A method to synchronize a video workout program across multiple devices, the method comprising:
communicatively coupling a server in a cloud network to an exercise machine that includes a first display through a first network connection;
communicatively coupling the server in the cloud network to a second display through a second network connection;
the server providing a video workout program to the exercise machine for execution at the exercise machine to enable a user to perform at least a portion of a workout of the video workout program on the exercise machine;
the server keeping state of the video workout program during execution of the video workout program at the exercise machine based on inputs from the exercise machine; and
the server synchronizing the second display with the first display of the exercise machine based on the state.

R. The method of section Q, further comprising:
receiving input indicative of the user performing at least a second portion of the workout off of the exercise machine; and
updating workout data included in the state to reflect performance of the second portion of the workout off of the exercise machine, wherein at least some of the updated workout data is displayed on the first display of the exercise machine.

S. The method of section R, wherein:
the input indicative of the user performing the second portion of the workout off of the exercise machine is received from a device not in direct communication with the exercise machine; and
the method further comprises distributing the at least some of the updated workout data to the exercise machine for display on the first display of the exercise machine.

T. The method of section R, wherein the input indicative of the user performing the second portion of the workout off of the exercise machine is received from the exercise machine.

U. The method of any one of sections Q-T, wherein the portion of the workout comprises a first portion performable on the exercise machine, the workout further comprising a second portion performable off the exercise machine, wherein the first portion of the workout comprises a first exercise modality and the second portion of the workout comprises a second exercise modality that is different than the first exercise modality.

V. The method of section U, wherein:
the second portion of the workout is performable with a second exercise machine; and
the method further comprises:

communicatively coupling the server in the cloud network to the second exercise machine through a third network connection; and the server further keeping state of the video workout program during execution of the video workout program based on inputs from the second exercise machine.

W. The method of section V, further comprising:

the server generating a second exercise machine control command based on the state; and the server providing the second exercise machine control command over the third network connection to the second exercise machine to control an actuator of the second exercise machine according to the second exercise machine control command.

X. The method of any one of sections Q-W, further comprising:

communicatively coupling the server in the cloud network to a heart rate monitor coupled to a user through a third network connection; and the server further keeping state of the video workout program during execution of the video workout program based on inputs from the heart rate monitor.

Y. The method of section X, further comprising adaptively scaling the video workout program on the exercise machine based on the state.

Z. The method of any one of sections Q-Y, wherein the second display is located in proximity to the exercise machine without being directly communicatively coupled to the exercise machine.

AA. The method of any one of sections Q-Z, wherein the synchronizing based on the state comprises distributing workout data of the video workout program that is displayed on the first display of the exercise machine, received from the exercise machine, and updated in the state to the second display for display on the second display.

BB. The method of any one of sections Q-Z, wherein the synchronizing based on the state comprises:

providing one or more workout controls to the second display for display on the second display;

receiving as one or more inputs from the second display a manual workout adjustment to adjust a difficulty of the workout entered using the one or more workout controls;

generating an exercise machine control command to adjust the difficulty of the workout according to the manual workout adjustment;

sending the exercise machine control command to the exercise machine for implementation at the exercise machine; and updating the state to include the adjusted workout difficulty;

wherein the exercise machine displays the adjusted workout difficulty on the first display of the exercise machine.

CC. A non-transitory computer-readable medium having computer-executable instructions stored thereon that are executable by a processing unit to perform or control performance of the method of any one of sections Q-BB.

DD. A method to keep state of a video workout program, the method comprising:

communicatively coupling a server in a cloud network to an exercise machine through a first network connection;

communicatively coupling the server in the cloud network to a heart rate monitor through a second network connection;

the server providing a video workout program to the exercise machine for execution at the exercise machine to enable a user to perform at least a portion of a workout of the video workout program on the exercise machine;

the server keeping state of the video workout program during execution of the video workout program at the exercise machine based on inputs from the exercise machine and the heart rate monitor; and the server adaptively scaling the video workout program based on the state.

EE. The method of section DD, further comprising:

receiving input indicative of the user performing at least a second portion of the workout off of the exercise machine; and updating workout data included in the state to reflect performance of the second portion of the workout off of the exercise machine, wherein at least some of the updated workout data is displayed on a display of the exercise machine.

FF. The method of section EE, wherein:

the input indicative of the user performing the second portion of the workout off of the exercise machine is received from a device not in direct communication with the exercise machine; and the method further comprises distributing the at least some of the updated workout data to the exercise machine for display on the display of the exercise machine.

GG. The method of section EE, wherein the input indicative of the user performing the second portion of the workout off of the exercise machine is received from the exercise machine.

HH. The method of any one of sections DD-GG, further comprising synchronizing a first display of the exercise machine with a second display not directly communicatively coupled to the exercise machine based on the state.

II. The method of section HH, wherein the synchronizing based on the state comprises distributing workout data of the video workout program that is displayed on the first display of the exercise machine, received from the exercise machine, and updated in the state to the second display for display on the second display.

JJ. The method of section HH, wherein the synchronizing based on the state comprises:

providing one or more workout controls to the second display for display on the second display;

receiving as one or more inputs from the second display a manual workout adjustment to adjust a difficulty of the workout entered using the one or more workout controls;

generating an exercise machine control command to adjust the difficulty of the workout according to the manual workout adjustment;

sending the exercise machine control command to the exercise machine for implementation at the exercise machine; and updating the state to include the adjusted workout difficulty;

wherein the exercise machine displays the adjusted workout difficulty on the first display of the exercise machine.

KK. The method of any one of sections DD-JJ, wherein the portion of the workout comprises a first portion performable on the exercise machine, the workout further comprising a second portion performable off the exercise machine, wherein the first portion of the workout comprises a first exercise modality and the second portion of the workout comprises a second exercise modality that is different than the first exercise modality.

LL. The method of section KK, wherein:
the second portion of the workout is performable with a second exercise machine; and
the method further comprises:
communicatively coupling the server in the cloud network to the second exercise machine through a third network connection; and
the server further keeping state of the video workout program during execution of the video workout program based on inputs from the second exercise machine.

MM. The method of section LL, further comprising:
the server generating a second exercise machine control command based on the state; and
the server providing the second exercise machine control command over the third network connection to the second exercise machine to control an actuator of the second exercise machine according to the second exercise machine control command.

NN. The method of any one of sections DD-MM, wherein the heart rate monitor is located in proximity to the exercise machine without being directly communicatively coupled to the exercise machine.

OO. The method of any one of sections DD-NN, wherein:
the inputs from the heart rate monitor include heart rate measurements of the user over time; and
the adaptively scaling comprises:
periodically determining from the heart rate measurements at least one of:
that an actual heart rate zone of the user is not equal to a current programmed heart rate zone; or
that the actual heart rate of the user is not trending toward the current programmed heart rate zone; and
in response to the periodically determining, adjusting a current difficulty level of the video workout program to adjust the user's actual heart rate zone toward the current programmed heart rate zone.

PP. The method of section OO, wherein the adjusting comprises adjusting the current difficulty level:
upward if the actual heart rate zone is lower than the current programmed heart rate zone; and
downward if the actual heart rate zone is higher than the current programmed heart rate zone.

QQ. The method of any one of sections OO-PP, wherein:
the adaptively scaling further comprises the server generating an exercise machine control command to adjust the current difficulty level based on the state; and
the adjusting the current difficulty level comprises the server providing the exercise machine control command over the first network connection to the exercise machine to control an actuator of the exercise machine according to the exercise machine control command.

RR. A non-transitory computer-readable medium having computer-executable instructions stored thereon that are executable by a processing unit to perform or control performance of the method of any one of sections DD-RR.

SS. A method comprising:
establishing a local connection between two or more exercise machines;
capturing a stream of performance metrics at the two or more exercise machines;
storing the performance metrics in a local database, wherein a copy of the local database is stored on each of the two or more exercise machines;
synchronizing the copies of the local database using the local connection;
querying a network connection between the two or more exercise machines and a server; and
in response to the network connection existing between the two or more exercise machines and the server, synchronizing the local database with a server database.

TT. The method of section SS, wherein the local connection comprises a Bluetooth, or wired connection.

UU. The method of sections SS or TT, wherein the stream of performance metrics is associated with a video workout program streamed to the two or more exercise machines.

VV. The method of section UU, wherein the video workout program includes a video including instructions for performing a workout.

WW. The method of section VV, wherein the video workout program includes exercise control commands configured to control one or more moveable or moving members of the two or more exercise machines.

XX. The method of section WW, wherein the exercise control commands are synchronized with the instruction for performing the workout, such that changes in the video are synchronized with changes in the control of the one or more moveable or moving members of the two or more exercise machines.

YY. The method of any of sections VV-XX, wherein the video is displayed synchronously on displays of the two or more exercise machines.

ZZ. The method of any of sections SS-YY, wherein the local database is updated continuously as performance metrics is collected at the two or more exercise machines, and wherein the copies of the local database are continuously synchronized using the local connection, such that each of the copies of the local database include all of the performance metrics captured at the two or more exercise machines.

AAA. The method of any of sections SS-ZZ, wherein a first exercise machine of the two or more exercise machines is a stationary bike and a second exercise machine of the two or more exercise machines is a treadmill, wherein a user performs a first portion of a workout on the first exercise machine as the first portion of the workout is displayed on a display of the first exercise machine, wherein the user performs a second portion of the workout on the second exercise machine as the second portion of the workout is displayed on a display of the second exercise machine, and wherein a state of the workout is kept in the local database as maintained using the local connection and the state of the workout is kept on the server by synchronizing the local database with the server database.

BBB. The method of any of sections SS-AAA, wherein the two or more exercise machines query a network connection between the two or more exercise machines and the server and synchronize the local database with the server database when a network connection exists between the two or more exercise machines and the server.

CCC. The method of any of sections SS-BBB, wherein the server generates a leaderboard using the performance metrics on the server database.

DDD. The method of any of sections SS-CCC, wherein the server adds metadata associated with the workout to the performance metrics on the server database.

EEE. The method of any of sections SS-DDD, wherein the metadata includes one or more of workout name, workout type, instructor, location, workout duration, user parameters, user goals, user workout records, and date and time.

FFF. The method of any of sections SS-EEE, wherein the performance metrics and added metadata are stored in a memory of the server for one or more of user access, generation of user exercise statistics, generation of performance statistics of the workout, and generation of a leaderboard.

GGG. The method of any of sections SS-EEE, wherein a copy of the local database is designated as the master copy, wherein conflicts between copies of the local database are resolved in favor of the master copy.

HHH. The method of any of sections SS-GGG, wherein synchronizing the local database with the server comprises synchronizing the master copy of the local database with the server.

III. The method of any of sections SS-HHH, wherein a copy of the local database on an exercise machine currently capturing performance metrics is designated as the master copy.

JJJ. The method of any of any of sections SS-III, wherein a first exercise machine captures workout metrics during a first portion of the video workout program and a second exercise machine captures workout metrics during a second portion of the video workout program, wherein a first copy of the local database on the first exercise machine is designated as the master copy during the first portion and a second copy of the local database on the second exercise machine is designated as the master copy during the second portion.

The invention claimed is:

1. A method to synchronize a video workout program across multiple devices, the method comprising:
communicatively coupling a server in a cloud network to an exercise machine through a first network connection;
communicatively coupling the server in the cloud network to a network device through a second network connection;
the server providing the video workout program to the exercise machine for execution at the exercise machine to enable a user to perform at least a portion of a workout of the video workout program on the exercise machine;
the server keeping a state of the video workout program during the execution of the video workout program based on inputs from the exercise machine and the network device;
the server generating an exercise machine control command based on the state;
the server providing the exercise machine control command over the first network connection to the exercise machine to control an actuator of the exercise machine according to the exercise machine control command;
receiving input indicative of the user performing at least a second portion of the workout off of the exercise machine; and
updating workout data included in the state to reflect performance of the second portion of the workout off of the exercise machine, wherein at least some of the workout data is displayed on a first display of the exercise machine.

2. The method of claim 1, wherein the network device is located in proximity to the exercise machine without being directly communicatively coupled to the exercise machine.

3. The method of claim 1, further comprising:
synchronizing the first display of the exercise machine with a second display of the network device based on the state.

4. The method of claim 3, wherein the synchronizing based on the state comprises:
distributing workout data of the video workout program that is displayed on the first display of the exercise machine, received from the exercise machine, and updated in the state of the network device for display on the second display of the network device.

5. The method of claim 3, wherein the synchronizing based on the state comprises:
providing one or more workout controls to the network device for display on the second display;
receiving as one or more of the inputs from the network device a manual workout adjustment to adjust a difficulty of the workout entered using the one or more workout controls;
generating a second exercise machine control command to adjust the difficulty of the workout according to the manual workout adjustment;
sending the exercise machine control command to the exercise machine for implementation at the exercise machine; and
updating the state to include the difficulty adjusted according to the manual workout adjustment, wherein the exercise machine displays the difficulty on the first display of the exercise machine.

6. The method of claim 1, wherein the portion of the workout comprises a first portion performable on the exercise machine, and wherein the first portion of the workout comprises a first exercise modality and the second portion of the workout comprises a second exercise modality that is different than the first exercise modality.

7. The method of claim 6, wherein the second portion of the workout is performable with a second exercise machine, the method further comprising:
communicatively coupling the server in the cloud network to the second exercise machine through a third network connection; and
the server further keeping the state of the video workout program during the execution of the video workout program based on inputs from the second exercise machine.

8. The method of claim 7, further comprising:
the server generating a second exercise machine control command based on the state; and
the server providing the second exercise machine control command over the third network connection to the second exercise machine to control a second actuator of the second exercise machine according to the second exercise machine control command.

9. The method of claim 1, further comprising;
communicatively coupling the server in the cloud network to a heart rate monitor coupled to the user through a third network connection; and
the server further keeping the state of the video workout program during the execution of the video workout program based on inputs from the heart rate monitor.

10. The method of claim 9, further comprising:
adaptively scaling the video workout program on the exercise machine based on the state.

11. A method to synchronize a video workout program across multiple devices, the method comprising:
- communicatively coupling a server in a cloud network to an exercise machine that includes a first display through a first network connection;
- communicatively coupling the server in the cloud network to a second display through a second network connection;
- the server providing the video workout program to the exercise machine for execution at the exercise machine to enable a user to perform at least a portion of a workout of the video workout program on the exercise machine;
- the server keeping a state of the video workout program during the execution of the video workout program at the exercise machine based on inputs from the exercise machine;
- the server synchronizing the second display with the first display of the exercise machine based on the state;
- receiving input indicative of the user performing at least a second portion of the workout off of the exercise machine; and
- updating workout data included in the state to reflect performance of the second portion of the workout off of the exercise machine, wherein at least some of the workout data is displayed on the first display of the exercise machine.

12. The method of claim 11, wherein the second display is located in proximity to the exercise machine without being directly communicatively coupled to the exercise machine.

13. The method of claim 11, wherein the synchronizing based on the state comprises:
- distributing workout data of the video workout program that is displayed on the first display of the exercise machine, received from the exercise machine, and updated in the state to the second display for display on the second display.

14. The method of claim 11, wherein the synchronizing based on the state comprises:
- providing one or more workout controls to the second display for display on the second display;
- receiving as one or more inputs from the second display a manual workout adjustment to adjust a difficulty of the workout entered using the one or more workout controls;
- generating an exercise machine control command to adjust the difficulty of the workout according to the manual workout adjustment;
- sending the exercise machine control command to the exercise machine for implementation at the exercise machine; and
- updating the state to include the difficulty adjusted according to the manual workout adjustment, wherein the exercise machine displays the difficulty on the first display of the exercise machine.

15. A method to keep state of a video workout program, the method comprising:
- communicatively coupling a server in a cloud network to an exercise machine through a first network connection;
- communicatively coupling the server in the cloud network to a heart rate monitor through a second network connection;
- the server providing the video workout program to the exercise machine for execution at the exercise machine to enable a user to perform at least a portion of a workout of the video workout program on the exercise machine;
- the server keeping a state of the video workout program during the execution of the video workout program at the exercise machine based on inputs from the exercise machine and the heart rate monitor;
- the server adaptively scaling the video workout program based on the state;
- receiving input indicative of the user performing at least a second portion of the workout off of the exercise machine; and
- updating workout data included in the state to reflect performance of the second portion of the workout off of the exercise machine, wherein at least some of the workout data is displayed on a display of the exercise machine.

16. The method of claim 15, wherein the heart rate monitor is located in proximity to the exercise machine without being directly communicatively coupled to the exercise machine.

17. The method of claim 15, wherein the inputs from the heart rate monitor include heart rate measurements of the user over time, and wherein the adaptively scaling comprises:
- periodically determining from the heart rate measurements at least one of:
  - that an actual heart rate zone of the user is not equal to a current programmed heart rate zone; or
  - that the actual heart rate zone of the user is not trending toward the current programmed heart rate zone; and
- in response to the periodically determining, adjusting a current difficulty level of the video workout program to adjust the actual heart rate zone of the user toward the current programmed heart rate zone.

18. The method of claim 17, wherein the adjusting comprises:
- adjusting the current difficulty level upward if the actual heart rate zone is lower than the current programmed heart rate zone; and
- adjusting the current difficulty level downward if the actual heart rate zone is higher than the current programmed heart rate zone.

19. The method of claim 17, wherein:
- the adaptively scaling further comprises the server generating an exercise machine control command to adjust the current difficulty level based on the state; and
- the adjusting further comprises the server providing the exercise machine control command over the first network connection to the exercise machine to control an actuator of the exercise machine according to the exercise machine control command.

* * * * *